United States Patent
Wrobleski et al.

(10) Patent No.: US 8,404,689 B2
(45) Date of Patent: *Mar. 26, 2013

(54) HETEROCYCLIC AMIDE COMPOUNDS USEFUL AS KINASE INHIBITORS

(75) Inventors: Stephen T. Wrobleski, Whitehouse Station, NJ (US); Jagabandhu Das, Mercerville, NJ (US); T. G. Murali Dhar, Newtown, PA (US); Alaric J. Dyckman, Lawrenceville, NJ (US); John Hynes, Washington Crossing, PA (US); Katerina Leftheris, Skillman, NJ (US); James Lin, Lawrenceville, NJ (US); Shuqun Lin, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/038,488

(22) Filed: Mar. 2, 2011

(65) Prior Publication Data

US 2011/0160207 A1      Jun. 30, 2011

Related U.S. Application Data

(62) Division of application No. 11/923,760, filed on Oct. 25, 2007, now Pat. No. 7,935,696.

(60) Provisional application No. 60/854,908, filed on Oct. 27, 2006.

(51) Int. Cl.
| | |
|---|---|
| A61K 31/495 | (2006.01) |
| A61K 31/445 | (2006.01) |
| A61K 31/404 | (2006.01) |
| C07D 209/04 | (2006.01) |
| C07D 211/06 | (2006.01) |
| C07D 241/04 | (2006.01) |

(52) U.S. Cl. ............. 514/252.12; 544/358; 544/386; 546/184; 546/245; 548/469; 548/492; 514/255.01; 514/315; 514/419

(58) Field of Classification Search ............ 548/469, 548/492; 514/415, 419, 252.12, 255.01, 514/315; 544/358, 386; 546/184, 245
See application file for complete search history.

(56) References Cited

U.S. PATENT DOCUMENTS

| | | | |
|---|---|---|---|
| 4,200,750 A | 4/1980 | Warner, Jr. et al. | |
| 5,658,903 A | 8/1997 | Adams et al. | |
| 5,932,576 A | 8/1999 | Anantanarayan et al. | |
| 5,945,418 A | 8/1999 | Bemis et al. | |
| 5,977,103 A | 11/1999 | Adams et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,251,914 B1 | 6/2001 | Adams et al. | |
| 6,277,989 B1 | 8/2001 | Chakravarty et al. | |
| 7,414,056 B2 * | 8/2008 | Dyckman et al. | 514/252.01 |
| 7,592,338 B2 * | 9/2009 | Dyckman et al. | 514/236.5 |
| 7,935,696 B2 * | 5/2011 | Wrobleski et al. | 514/231.5 |
| 7,943,658 B2 * | 5/2011 | Liu et al. | 514/419 |

FOREIGN PATENT DOCUMENTS

| | | |
|---|---|---|
| EP | 1 714 958 | 10/2006 |
| EP | 1 911 751 | 4/2008 |
| WO | WO 00/07980 | 2/2000 |
| WO | WO00/12074 | 3/2000 |
| WO | WO00/12497 | 3/2000 |
| WO | WO 00/55120 | 9/2000 |
| WO | WO00/56738 | 9/2000 |
| WO | WO01/27089 | 4/2001 |
| WO | WO01/34605 | 5/2001 |
| WO | WO02/14308 | 2/2002 |
| WO | WO 03/032970 | 4/2003 |
| WO | WO 03/032986 | 4/2003 |
| WO | WO2004/071440 | 8/2004 |
| WO | WO2004/089929 | 10/2004 |
| WO | WO 2004/099156 | 11/2004 |
| WO | WO 2005/061465 | 7/2005 |
| WO | WO2005/100338 | 10/2005 |
| WO | WO 2005/115374 | 12/2005 |
| WO | WO2005/115374 | 12/2005 |
| WO | WO 2006/067445 | 6/2006 |
| WO | WO2006/067446 | 6/2006 |
| WO | WO2006/094236 | 9/2006 |
| WO | WO2006/137376 | 12/2006 |

OTHER PUBLICATIONS

Das et al (2005): STN International HCAPLUS database, (Columbus, Ohio), Accession No. 2005:409524.*
Brown et al (2005): STN International HCAPLUS database, (Columbus, Ohio), Accession No. 2005:588911.*
Bundgaard, H., Design of Prodrugs, 1985 Elsevier.
Bundgaard, H., "Means to Enhance Penetration, Prodrugs as a means to improve the delivery of peptide drugs", Advanced Drug Delivery Reviews, vol. 8, pp. 1-38 (1992).
Carman, R.M. et al., "Conversion of Sucrose into a Carboxylic Acid", Journal of Chemical Education, vol. 46(12), pp. 847-848 (1969).

(Continued)

Primary Examiner — Golam M M Shameem
(74) Attorney, Agent, or Firm — Laurelee A. Duncan; Pamela A. Mingo; Gary A. Greenblatt

(57) ABSTRACT

A compound of Formula I

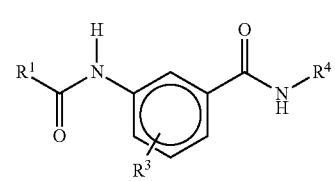

and enantiomers, diastereomers and pharmaceutically-acceptable salts thereof. Also disclosed are pharmaceutical compositions containing compounds of Formula I, and methods of treating conditions associated with the activity of p38 kinase.

15 Claims, No Drawings

OTHER PUBLICATIONS

Corwin, A. et al., "The Condensation of Pyrroles with Bromine. A Self-Oxidation and a New Type of Displacement Reaction", Journal of American Chemical Society, vol. 66, pp. 1137 (1944).
Greene, T. et al., Protective Groups in Organic Synthesis, Wiley & Sons (1991).
Henry, J. et al., "p38 mitogen-activated protein kinase as a target for drug discovery", Drugs of the Future, vol. 24(12), pp. 1345-1354 (1999).
Katritzky, A. et al., Comprehensive Heterocyclic Chemistry II, The Structure, Reactions, Synthesis, and Users of Heterocyclic Compounds, vol. 5, pp. 91-133 (1996).
Krogsgaard-Larsen, P. et al., "Design and Application of Prodrugs", A Textbook of Drug Design and Development, pp. 113-191 (1991).
Larock, R., Comprehensive Organic Transformations. A Guide to Functional Group Preparation, VCH Publishers Inc., pp. 385-439 (1989).
Lisowski, V. et al., "Design, Synthesis, and Evaluation of Novel Thienopyrrolizinones as Antitubulin Agents", J. Med. Chem., vol. 47, pp. 1448-1464 (2004).
Moreland, L. et al., "Etanercept Therapy in Rheumatoid Arthritis", Ann. Inter Med., vol. 130, pp. 478-486 (1999).
Notari, R., "Theory and Practice of Prodrug Kinetics", Methods in Enzymology, vol. 112, pp. 309-323 (1985).
Raingeaud, J. et al, "MKK3- and MKK6-Regulated Gene Expression is Mediated by the p38 Mitogen-Activated Protein Kinase Signal Transduction Pathway", Molecular and Cellular Biology, vol. 16(3), pp. 1247-1255 (1996).
Rankin, E. et al., "The Therapeutic Effects of an Engineered Human Anti-Tumour Necrosis Factor Alpha Antibody (CDP571) in Rheumatoid Arthritis", British Journal of Rheumatology, vol. 34, pp. 334-342 (1995).
Salituro, F. et al., "Inhibitors of p38 MAP Kinase: Therapeutic Intervention in Cytokine-Mediated Diseases", Current Medicinal Chemistry, vol. 6, pp. 807-823 (1999).
European Search Report application 12156082.5, dated May 29, 2012.

* cited by examiner

HETEROCYCLIC AMIDE COMPOUNDS USEFUL AS KINASE INHIBITORS

This application is a Divisional of U.S. Ser. No. 11/923,760, filed Oct. 25, 2007 which claims priority to U.S. Provisional Patent Application Ser. No. 60/854,908, filed Oct. 27, 2006, which is hereby incorporated by reference in its entirety.

FIELD OF THE INVENTION

This invention relates to heterocyclic amide compounds useful for treating p38 kinase-associated conditions. The invention further pertains to pharmaceutical compositions containing at least one compound according to the invention useful for treating kinase-associated conditions, such as p38 kinase-associated conditions, and methods of inhibiting the activity of kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., Drugs Fut., 24:1345-1354 (1999); Salituro et al., Curr. Med. Chem., 6:807-823 (1999)]. Evidence in human patients indicates that protein antagonists of cytokines are effective in treating chronic inflammatory diseases, such as, for example, monoclonal antibody to TNF-α (Enbrel) [Rankin et al., Br. J. Rheumatol., 34:334-342 (1995)], and soluble TNF-α receptor-Fc fusion protein (Etanercept) [Moreland et al., Ann. Intern. Med., 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including, but not limited to, proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. While the inhibition of p38α and β enzymes as both forms is noted, it is also of interest to obtain compounds whose inhibition of the p38α form is proportionally higher than the β form.

Compounds that reportedly inhibit p38 kinase and cytokines, such as IL-1 and TNF-α for use in treating inflammatory diseases, are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G.D. Searle & Co.; PCT publication numbers WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain heterocyclic amide compounds useful as kinase inhibitors, particularly kinases p38α and β, with a subgroup selective for p38α. Each of the patent applications, patents, and publications referred to herein is incorporated herein by reference.

SUMMARY OF THE INVENTION

The instant invention generally pertains to compounds of Formula I,

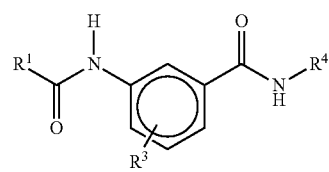

and enantiomers, diastereomers and pharmaceutically-acceptable salts thereof (particularly pharmaceutically-acceptable salts), wherein:

$R^1$ is an optionally substituted alkyl, optionally substituted cycloalkyl, optionally substituted aryl, optionally substituted heterocyclo or optionally substituted heteroaryl;

$R^3$ is hydrogen, $C_1$-$C_4$ alkyl or halogen; and $R^4$ is hydrogen, optionally substituted carboxyl, optionally substituted alkyl, optionally substituted alkoxy, optionally substituted cycloalkyl, optionally substituted aryl, optionally substituted heterocyclo or optionally substituted heteroaryl;

with the provisos that:

(a) $R^1$ is not an optionally substituted pyrazolyl, optionally substituted thiazolyl or optionally substituted aminothiazolyl; and (b) $R^4$ is not an optionally substituted pyrazolyl.

Listed below are definitions of various terms used to describe this invention. These definitions apply to the terms as they are used throughout this specification, unless otherwise limited in specific instances, either individually or as part of a larger group.

The terms "alkyl" and "alk" refers to a straight or branched chain alkane (hydrocarbon) radical containing from 1 to 12 carbon atoms, preferably 1 to 6 carbon atoms. Exemplary groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like.

"Substituted alkyl" refers to an alkyl group substituted with one or more substituents, preferably 1 to 4 substituents, at any available point of attachment on the alkyl straight or branched chain. Exemplary substituents include one or more of the following groups: halo (e.g., a single halo substituent or multiple halo substituents forming, in the latter case, groups such as a perfluoroalkyl group or an alkyl group bearing $Cl_3$ or $CF_3$), nitro, cyano, hydroxy, alkoxy, haloalkoxy (e.g., trifluoromethoxy), —O-aryl, —O-heterocyclo, —O-alkylene-aryl, —O-haloalkyl, alkylthio, carboxy (i.e., —COOH), alkoxycarbonyl, alkylcarbonyloxy, carbamoyl, substituted carbamoyl, carbamate, substituted carbamate, urea, substituted urea, amidinyl, substituted amidinyl, aryl, heterocycle, cycloalkyl, —NR$^c$R$^d$, —OC(=O)NR$^c$R$^d$, —C(=O)NR$^c$R$^d$, —NR$^e$C(=O)NR$^c$R$^d$, —NR$^e$C(O)$^2$—NR$^c$R$^d$, —N(R$^e$)S(O)$_2$NR$^c$R$^d$, —N(R$^e$)P(O)$_2$NR$^c$R$^d$, (wherein each of R$^c$ and R$^d$ is independently selected from the group consisting of hydrogen, alkyl, aryl, and heterocyclo and R$^e$ is hydrogen, alkyl, or phenyl), —SR$^f$, —S(=O)R$^g$, —S(O)$_2$R$^g$, —NR$^e$S(O)$_2$—R$^g$, —P(O)$_2$—R$^g$, —NR$^e$P(O)$_2$—R$^g$, —NR$^e$C(=O)R$^f$, —NR$^e$C(O)$_2$R$^f$, —OC(=O)R$^f$, —OC(=O)OR$^f$, —C(=O)OR$^f$ and —C(=O)R$^f$ (wherein R$^e$ is defined as immediately above, R$^f$ is hydrogen, alkyl, aryl or heterocyclo, and R$^g$ is alkyl, aryl, or heterocyclo). In the aforementioned substituents, in each instance, the alkyl, aryl, heterocyclo or cycloalkyl groups (R$^c$, R$^d$, R$^e$, R$^f$, and R$^g$) in turn can be optionally substituted with one to four, preferably one to three further groups, selected from the group consisting of R$^k$, —O—R$^k$, cyano, nitro, haloalkyl, haloalkoxy, halo, —NR$^k$R$^m$, —OC(=O)NR$^k$R$^m$, —C(=O)NR$^k$R$^m$, —NR$^k$C(=O)R$^m$, —SR$^k$, —S(=O)R$^n$, —S(O)$_2$R$^n$, —OC(=O)R$^k$, —C(=O)OR$^k$, —C(=O)R$^k$, phenyl, benzyl, phenyloxy, or benzyloxy, and a lower alkyl substituted with one to two of —O—R$^k$, cyano, nitro, haloalkyl, haloalkoxy, halo, —NR$^k$R$^m$, —OC(=O)NR$^k$R$^m$, —C(=O)NR$^k$R$^m$, —NR$^k$C(=O)R$^m$, —SR$^k$, —S(=O)R$^n$, —S(O)$_2$R$^n$, —OC(=O)R$^k$, —C(=O)OR$^k$, —C(=O)R$^k$, phenyl, benzyl, phenyloxy, or benzyloxy, wherein R$^k$ and R$^m$ are selected from the group consisting of hydrogen, lower alkyl, hydroxy(lower alkyl), halo(lower alkyl), cyano(lower alkyl), and amino(lower alkyl), and R$^n$ is lower alkyl.

As used herein, "alkylene" refers to a bivalent alkyl radical having the general formula —(CH$_2$)$_n$—, where n is 1 to 10 (particularly 1-6 and, more particularly, 1-4). Non-limiting examples include methylene, dimethylene, trimethylene, tetramethylene, pentamethylene, and hexamethylene. The term "lower alkylene" herein refers to those alkylene groups having from about 1 to about 6 carbon atoms and, more particularly, 1-4. "Substituted alkylene" refers to an alkylene group substituted with one or more substituents, preferably 1 to 4 substituents, at any available point of attachment. Exemplary substituents include, but are not limited to alkyl, substituted alkyl, and those groups recited above as exemplary alkyl substituents.

When the term alkyl is used as a subscript following another particularly-named group, as in "arylalkyl," "substituted arylalkyl," "cycloalkylalkyl," etc., or as in hydroxy (lower alkyl), this refers to an alkyl group having one or two (preferably one) substituents selected from the other, particularly-named group. Thus, for example, arylalkyl includes benzyl, biphenyl and phenylethyl. A "substituted arylalkyl" will be substituted on the alkyl portion of the radical with one or more groups selected from those recited above for alkyl, and/or will be substituted on the aryl portion of the radical with one or more groups selected from those recited below for substituted aryl.

The term "alkenyl" refers to a straight or branched chain hydrocarbon radical containing from 2 to 12 carbon atoms and at least one carbon-carbon double bond. Exemplary groups include ethenyl or allyl. "Substituted alkenyl" refers to an alkenyl group substituted with one or more substituents, preferably 1 to 4 substituents, at any available point of attachment. Exemplary substituents on the alkenyl include, but are not limited to, alkyl, substituted alkyl, and those groups recited above as exemplary alkyl substituents. Particular examples of substituents for alkenyls are those selected from the group consisting of 2-6 carbons.

The term "alkenylene" refers to a straight or branched chain bivalent hydrocarbon radical containing from 2 to 12 carbon atoms and at least one carbon-carbon double bond. Exemplary groups include ethenylene or allylene. "Substituted alkenylene" refers to an alkenylene group substituted with one or more substituents, preferably 1 to 4 substituents, at any available point of attachment. Exemplary substituents include, but are not limited to, alkyl, substituted alkyl, and those groups recited above as exemplary alkyl substituents. Particular examples of substituents for alkenylenes are those selected from the group consisting of 2-6 carbons.

The term "alkynyl" refers to a straight or branched chain hydrocarbon radical containing from 2 to 12 carbon atoms and at least one carbon to carbon triple bond. Exemplary groups include ethynyl. "Substituted alkynyl" refers to an alkynyl group substituted with one or more substituents, preferably 1 to 4 substituents, at any available point of attachment. Exemplary substituents include, but are not limited to, alkyl, substituted alkyl, and those groups recited above as exemplary alkyl substituents. Particular examples of substituents for alkynyls are those selected from the group consisting of 2-6 carbons.

The term "alkynylene" refers to a straight or branched chain bivalent hydrocarbon radical containing from 2 to 12 carbon atoms and at least one carbon to carbon triple bond. Exemplary groups include ethynylene. "Substituted alkynylene" refers to an alkynylene group substituted with one or more substituents, preferably 1 to 4 substituents, at any available point of attachment. Exemplary substituents include, but are not limited to, alkyl, substituted alkyl, and those groups recited above as exemplary alkyl substituents. Particular examples of substituents for alkynylenes are those selected from the group consisting of 2-6 carbons.

The term "cycloalkyl" refers to a fully saturated cyclic hydrocarbon group containing from 1 to 3 rings and 3 to 8 carbons per ring. Exemplary groups include cyclopropyl, cyclobutyl, cyclopentyl, and cyclohexyl with a particular value being cyclopropyl. The term "cycloalkyl" also includes groups having a carbon-carbon bridge of one to two bridgehead carbon atoms, and bicyclic and tricyclic groups in which at least one of the rings is a saturated, carbon-containing ring, in which case the second or third ring may be carbocyclic or heterocyclic, provided that the point of attachment is to the cycloalkyl group. The further rings may be attached to the saturated, carbon-containing ring in a spiro or fused fashion. "Substituted cycloalkyl" refers to a cycloalkyl group substituted with one or more substituents, preferably 1 to 4 substituents, at any available point of attachment. Exemplary substituents include, but are not limited to, alkyl, substituted alkyl, oxo(=O), and those groups recited above as exemplary alkyl substituents.

The term "cycloalkylene" refers to a bivalent cycloalkyl group as defined above. Exemplary groups include cyclopropylene, cyclobutylene, cyclopentylene and cyclohexylene. "Substituted cycloalkylene" refers to a cycloalkylene group substituted with one or more substituents, preferably 1 to 4 substituents, at any available point of attachment selected from those recited for substituted cycloalkyl.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group. "Substituted cycloalkenyl" refers to a cycloalkenyl group substituted with one or more substituents, preferably 1 to 4 substituents, at any available point of attachment selected from those recited above for cycloalkyl groups.

The term "cycloalkenylene" refers to a bivalent cycloalkenyl group, as defined above. Exemplary groups include cyclobutenylene, cyclopentenylene, and cyclohexenylene. "Substituted cycloalkenylene" refers to a cycloalkenylene group substituted with one or more substituents, preferably 1 to 4 substituents, at any available point of attachment, selected from those recited for substituted cycloalkyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively.

The term "thiol" refers to —SH.

The term "alkoxycarbonyl" refers to an alkoxy group bonded through a carbonyl group (i.e., —C(=O)—O-alkyl).

The term "alkylcarbonyl" refers to an alkyl group bonded through a carbonyl group (i.e., —C(=O)alkyl).

The term "alkylcarbonyloxy" refers to an alkylcarbonyl group bonded through an oxygen linkage (i.e., —O—C(=O)-alkyl).

The term "amido" refers to the group —NHC(=O)H, and amidinyl refers to the group —C(=NH)(NH$_2$). A "substituted amido" refers to the group —NR$^p$C(=O)R$^q$, and a "substituted amidinyl" refers to the group —C(=NR$^p$)(NR$^q$R$^r$), wherein R$^p$, R$^q$, and R$^r$ are selected from hydrogen, alkyl, substituted alkyl, cycloalkyl, substituted cycloalkyl, aryl, substituted aryl, heterocyclo, and substituted heterocyclo, provided that at least one of R$^p$, R$^q$, and R$^r$ is other than hydrogen. A more particular value for R$^p$ is selected from the group consisting of. A more particular value for R$^q$ is selected from the group consisting of. A more particular value for R$^r$ is selected from the group consisting of.

The term "aryl" encompasses monocyclic and polycyclic aryl groups which contain only carbons on the first ring. The term "monocyclic aryl" refers to phenyl (where the ring only contains carbons), and the term "polycyclic aryl" refers to napthyl and anthracenyl, to phenyl rings having at least a second ring fused thereto, and to napthyl rings having a third ring fused thereto. In the case of a polycyclic aryl consisting of a phenyl ring having a second or third ring fused thereto, or a napthyl ring having a third ring fused thereto, the additional rings may be aromatic or non-aromatic carbocyclic or heterocyclic rings, provided that in such cases the point of attachment will be to the carbocyclic aromatic ring. For example, a subset of this aryl group is a polycyclic aryl group wherein the second ring is a "heteroaryl" which contains carbon atoms and at least one heteroatom selected from the group consisting of O, N, and S (provided that O and S cannot be adjacent to each other in the same ring). Alternatively, a ring carbon atom of the second and/or third further rings may be replaced with a carbonyl [—C(=O)group] (e.g., when such rings are non-aromatic). "Substituted aryl" refers to an aryl group substituted by one or more substituents, preferably 1 to 4 substituents (more preferably 1 or 2), at any point of attachment of any ring, selected from alkyl, substituted alkyl, and the substituents recited above for substituted alkyl groups.

Accordingly, examples of aryl groups that are of interest in forming compounds of the invention include:

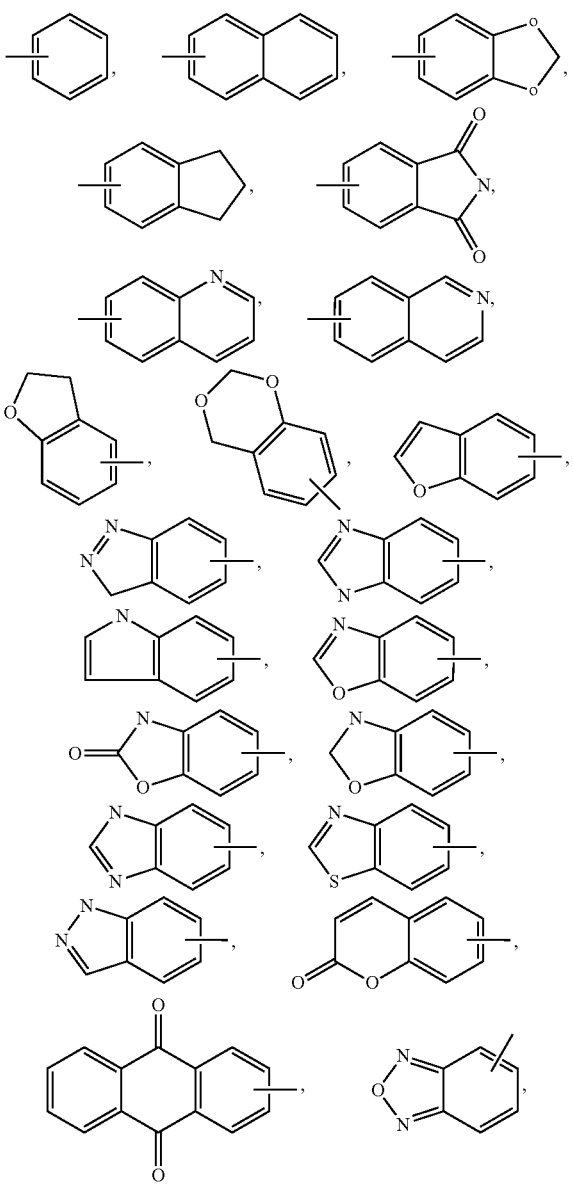

and, additionally, similar structures.

The term "arylene" refers to bivalent aryl groups as defined above.

"Carbamoyl" refers to the group —C(=O)—NR$^h$R$^i$, wherein R$^h$ and R$^i$ are selected from hydrogen, alkyl, cycloalkyl, aryl, and heterocyclo.

"Carbamate" refers to the group —O—C(=O)—NR$^h$R$^i$, and "urea" refers to the groups NH—C(=O)—NR$^h$R$^i$ and N(alkyl)-C(=O)—NR$^h$R$^i$, wherein R$^h$ and R$^i$ are selected from the same groups recited for carbamoyl.

"Substituted carbamoyl", "substituted carbamate", and "substituted urea" refer to the groups —C(=O)—NR$^h$R$^i$, —O—C(=O)—NR$^h$R$^i$, and —N(R$^j$)—C(=O)—NR$^h$R$^i$, respectively, wherein R$^h$, R$^i$, and R$^j$ are selected from hydrogen, alkyl, substituted alkyl, cycloalkyl, substituted cycloalkyl, aryl, substituted aryl, heterocyclo, and substituted heterocyclo, provided that at least one of R$^h$, R$^i$, and R$^j$ is substituted alkyl, substituted cycloalkyl, substituted aryl, or substituted heterocyclo.

The terms "heterocycle", "heterocyclic" and "heterocyclo" refer to fully saturated, partially unsaturated, or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Thus, the term "heteroaryl" is a subset of heterocyclo groups. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized, provided sulfur and oxygen are not adjacent to each other in the ring. (The term "heteroarylium" refers to a heteroaryl group bearing a quaternary nitrogen atom and thus a positive charge.) Additionally, one or more (preferably one) carbon ring atoms of the heterocyclo ring may, as valence allows, be replaced with carbonyl group, i.e., —C(=O)—. The heterocyclic group may be attached to the remainder of the molecule at any heteroatom or carbon atom of the ring or ring system.

Exemplary monocyclic heterocyclic groups include those selected from the group consisting of ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include those selected from the group consisting of indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrollinyl, dibenzofuranyl, acridinyl, phenanthridinyl, xanthenyl and the like.

The term "heterocyclene" refers to bivalent heterocycle groups as defined above.

"Substituted heterocycle", "substituted heterocyclic" and "substituted heterocyclo" (such as "substituted heteroaryl") refer to heterocycle, heterocyclic or heterocyclo groups substituted with one or more substituents, preferably 1 to 4 substituents, at any available point of attachment, wherein the substituents are selected from those recited above for substituted cycloalkyl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The term "heteroaryl" refers to five and six membered monocyclic aromatic heterocyclo groups, as well as bicyclic and tricyclic heterocyclic ring systems in which the point of attachment of the ring system to another group is via a five or six membered aromatic ring of the ring system. Thus, for example, the term heteroaryl includes groups such as five or six membered heteroaryl groups, such as thienyl, pyrrolyl, oxazolyl, pyridyl, pyrazinyl, and the like, wherein fused rings completing bicyclic and tricyclic groups may contain only carbon atoms and may be saturated, partially saturated, or unsaturated. Heteroaryl groups which are bicyclic or tricyclic must include at least one fully aromatic ring but the other fused ring or rings may be aromatic or non-aromatic.

The term "substituted heteroaryl" refers to five and six membered monocyclic aromatic heterocyclo groups substituted with one or more substituents, such as 1 to 4 substituents (more particularly 1-3 substituents and, even more particularly, 1-2 substituents), at any available point of attachment, wherein the substituents are selected from those recited above for substituted cycloalkyl groups.

Exemplary monocyclic heteroaryl groups include those selected from the group consisting of pyrrolyl, pyrazolyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, and the like.

Exemplary bicyclic heteroaryl groups include those selected from the group consisting of indolyl, benzothiazolyl, benzodioxolyl, benzoxazolyl, benzothienyl, quinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, and the like.

Exemplary tricyclic heteroaryl groups include carbazolyl, benzidolyl, phenanthrollinyl, acridinyl, phenanthridinyl, xanthenyl and the like.

The terms "hydroxylamine" and "hydroxylamide" refer to the groups —NH—OH and —C(=O)—NH—OH, respectively.

Unless otherwise indicated, the term "substituted amino" as employed herein alone or as part of another group refers to amino substituted with one or two substituents, which may be the same or different, such as alkyl, aryl, arylalkyl, heterocyclo, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, —C(O)R$^t$, —C(=O)OR$^t$, —C(=O)NR$^t$R$^u$, —S(O)$_2$R$^t$, —S(O)$_2$OR$^t$, or —S(O)$_2$NR$^t$R$^u$, wherein R$^t$ and R$^u$ are each independently selected from the group consisting of hydrogen, alkyl, substituted alkyl, aryl, substituted aryl or heterocyclo. These substituents may be further substituted with a carboxylic acid and/or any of the substituents for alkyl as set out above.

Also, R$^t$ and R$^u$ may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, aryl, heterocyclo, alkoxy, alkylthio, halo, trifluoromethyl, hydroxy, amino, —C(O)R$^f$, —C(=O)OR$^f$, —C(=O)NR$^f$R$^g$, —S(O)$_2$R$^f$, —S(O)$_2$OR$^f$, or —S(O)$_2$NR$^f$R$^g$, wherein R$^f$ and R$^g$ can be hydrogen, alkyl, substituted alkyl, aryl, substituted aryl or heterocyclo.

The term "heteroatoms" shall include oxygen, sulfur and nitrogen.

The terms "halogen" or "halo" refer to chlorine, bromine, fluorine or iodine.

The term "haloalkyl" means an alkyl having one or more halo substituents, particularly when the alkyl portion is selected from the group consisting of $C_1$-$C_3$. For example, haloalkyl can be $CF_3$.

The term "haloalkoxy" means an alkoxy group having one or more halo substituents particularly when the alkoxy portion comprises $C_1$-$C_3$. For example, "haloalkoxy" includes —$OCF_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted, in which case the substituents are selected from those recited above for cycloalkyl and aryl groups.

When the term "unsaturated" is used herein to refer to a ring or group, the ring or group may be fully unsaturated or partially unsaturated.

When it is stated that a group may be "optionally substituted," this is intended to include unsubstituted groups and substituted groups wherein the substituents are selected from those recited above for the particularly named group. Thus, when reference is made to an optionally substituted aryl, it is intended to refer to unsubstituted aryl groups, such as phenyl or naphthyl, and such groups having one or more (preferably 1 to 4, and more preferably 1 or 2) substituents selected from alkyl, substituted alkyl, and those substituents recited for substituted alkyl groups. When the term "optionally substituted" precedes a Markush group, the term "optionally substituted" is intended to modify each one of the species recited in the Markush group. Thus, for example, the phrase "optionally substituted aryl, cycloalkyl, or heterocycle" includes aryl, substituted aryl, cycloalkyl, substituted cycloalkyl, heterocycle, and substituted heterocycle.

Among the compounds of the invention, in the case of a compound which has a sulfide, the sulfur atom may be converted into oxido at an appropriate oxidation state, and all of these oxido derivatives are included herein.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

"Solvate" refers to a molecular or ionic complex of molecules or ions of solvent with molecules or ions of solute. It should further be understood that solvates (e.g., hydrates) of the compounds of Formula I or Formula II are also within the scope of the present invention. Methods of solvation are generally known in the art.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991), incorporated by reference as to the listing of such protective groups.

Unless otherwise indicated, any heteroatom with unsatisfied valences is assumed to have hydrogen atoms sufficient to satisfy the valences.

Carboxylate anion refers to a negatively charged group —COO.

The compounds of the present invention may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of the present invention may form salts with alkali metals such as sodium, potassium, and lithium; with alkaline earth metals such as calcium and magnesium; and with organic bases such as dicyclohexylamine, tributylamine, pyridine, and amino acids such as arginine, lysine, and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid, and various others (e.g., nitrates, phosphates, borates, tartrates, citrates, succinates, benzoates, ascorbates, salicylates, and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures; it also embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

Compounds of the present invention may also have prodrug forms. Any compound that will be converted in vivo to provide the bioactive agent (i.e., the compound for Formula I or Formula II) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder et al. (Academic Press, 1985);

b) H. Bundgaard, Chapter 5: "Design and Application of Prodrugs", *A Textbook of Drug Design and Development*, Harwood Academic Publishers, publ., Krogsgaard-Larsen, P. et al., eds., pp. 113-191 (1991); and c) H. Bundgaard, *Advanced Drug Delivery Reviews*, 8:1-38 (1992), each of which is incorporated herein by reference.

DETAILED DESCRIPTION OF THE INVENTION

One embodiment of the present invention relates to a compound of Formula I

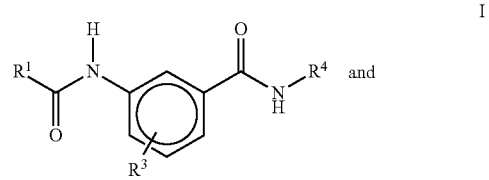

enantiomers, diastereomers and pharmaceutically-acceptable salts thereof, wherein:

R[1] is optionally substituted alkyl, optionally substituted cycloalkyl, optionally substituted aryl, optionally substituted heterocyclo or optionally substituted heteroaryl (with particular values being described below);

R[3] is hydrogen, $C_1$-$C_4$ alkyl or halogen (particularly H, Cl, F, or $CH_3$); and R[4] is hydrogen, optionally substituted carboxyl, optionally substituted alkyl, optionally substituted alkoxy, optionally substituted cycloalkyl, optionally substituted aryl, optionally substituted heterocyclo or optionally substituted heteroaryl. A more particular value for R[4] is selected from the group consisting of $C_1$-$C_5$ alkyl (including methyl, ethyl, and branched and unbranched $C_3$-$C_5$ alkyls), $C_3$-$C_6$ cycloalkyl (for example, cyclopropyl), wherein the alkyls and cycloalkyls are optionally substituted with 1-4 members selected from the group consisting of $C_1$-$C_5$ alkyls and $C_1$-$C_5$ alkoxy groups (including methyl, ethyl, and branched and unbranched $C_3$-$C_5$ alkyls and alkoxys);

with the provisos that:
(a) R[1] is not optionally substituted pyrazolyl, optionally substituted thiazolyl or optionally substituted aminothiazolyl; and
(b) R[4] is not optionally substituted pyrazolyl.

In another particular embodiment, R[1] is selected from the group consisting of optionally substituted $C_1$-$C_4$ alkyls, optionally substituted $C_3$-$C_6$ cycloalkyls, optionally substituted $C_2$-$C_4$ alkenyls, optionally substituted 3-6 membered heterocycles, optionally substituted $C_5$-$C_6$ aryls and optionally substituted heteroaryls (with more particular groups as defined below), wherein:
(a) the unsubstituted and substituted heteroaryls have a ring size of 5-10 members and 1-3 hetero atoms selected from the group consisting of N, S and O, provided that O and S are not adjacent to each other, O and O are not adjacent to each other and S and S are not adjacent to each other; and
(b) the substitutions themselves may be further substituted (for example, with 1-3 members).

In yet another particular embodiment, R[1] is selected from the group consisting of optionally substituted $C_1$-$C_4$ alkyl, optionally substituted $C_1$-$C_6$ cycloalkyl, optionally substituted $C_1$-$C_4$ alkenyl, optionally substituted 3-6 membered heterocyclo, optionally substituted $C_5$-$C_6$ aryl or optionally substituted 5-6 membered heteroaryl wherein the heteroaryl has 1-2 heteroatoms selected from N, O and S (provided that O and S are not adjacent to each other, O and O are not adjacent to each other and S and S are not adjacent to each other), and the rest of the heteroaryl is carbon atoms.

More particular values for R[1] are phenyl and heteroaryls selected from the group consisting of unsubstituted or substituted heteroaryls having a ring size of 5-10 members, wherein 1-3 members are selected from the group consisting of N, S and O, provided that O and S are not adjacent to each other, O and O are not adjacent to each other and S and S are not adjacent to each other.

A yet more particular value for R[1] is selected from the group consisting of phenyl, thiophene, pyrrole, indole and indazole.

A still more particular value for R[1] is selected from the group consisting of thiophene, pyrrole, indole and indazole.

Particular examples of substitutions for the substituted aryl and heteroaryl groups may be selected from the group consisting of phenyl, —$CH_2$-phenyl, pyridinyl, and $CH_2$-benzimidazolyl.

The substitutions on the aryl and heteroaryl groups may themselves be substituted, for example, by 1 to 3 members (substituents) selected from the group consisting of aryls and heteroaryls (for example $C_5$-$C_6$ membered aryls having 1-2 heteroatoms selected from the group consisting of N, S and O provided that O and S are not adjacent to each other, O and O are not adjacent to each other and S and S are not adjacent to each other), $C_1$-$C_3$ alkyls (for example, methyl, ethyl and propyl (including n-propyl and isopropyl as —$CH(CH_3)_2$), $CH_2OH$, haloalkyls (for example, $CF_3$), alkoxys (for example, methoxy), halogens, (for example, Cl and F), —$NH_2$, $N(CH_3)_2$, $C(O)NH_2$, —$NHSO_2CH_3$, —$SO_2NH_2$, —$CH_2N(CH_3)_2$, —$C(O)NHCH_3$, —$C(O)N(CH_3)_2$, —$C(O)NHCH(CH_3)_2$, —$C(O)NHCH_2CH_3$, —O—$CH_2CH(OH)CH_2OH$; $CO_2$—$CH_2CH_3$, —$C(O)OC(CH_3)_3$; —CN, —OH (or $O^{-1}$ as attached to an $N^{+1}$ on a heteroaryl ring), heterocycles, optionally with alkyl or carbonyl links (for example

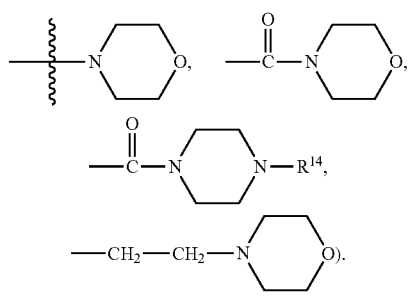

Even more particular values of R[1] are found in the compositions listed in the tables. For example, the group consisting of the following members is of special interest in making compounds with alpha selectivity, for example, with alpha selectivity of at least 50 fold as described below:

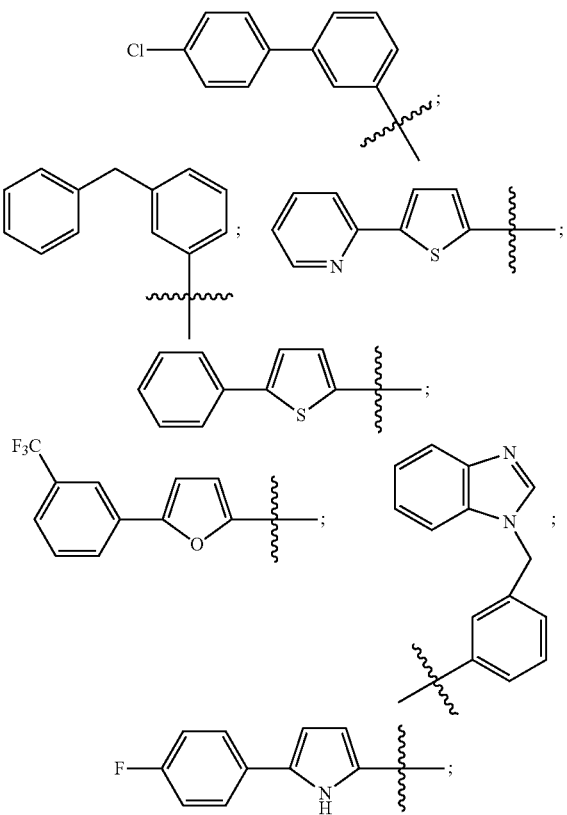

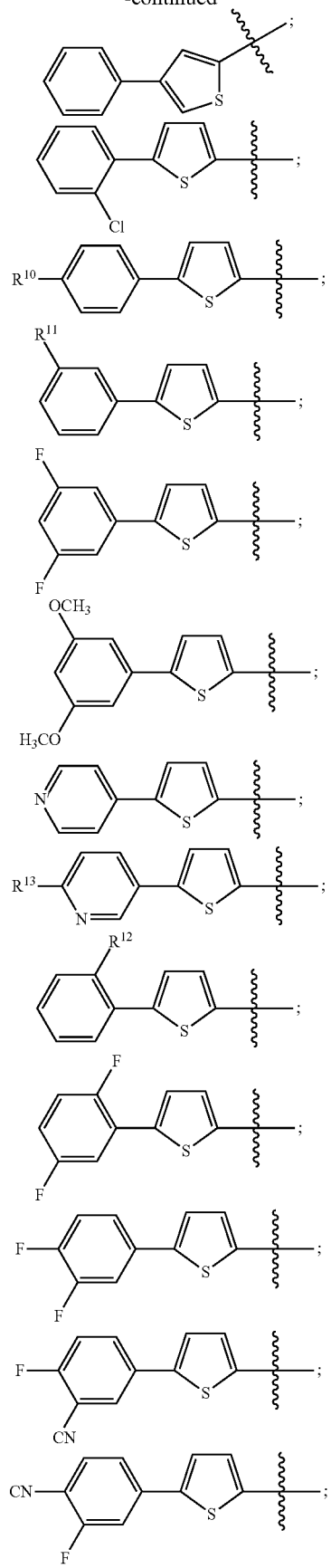
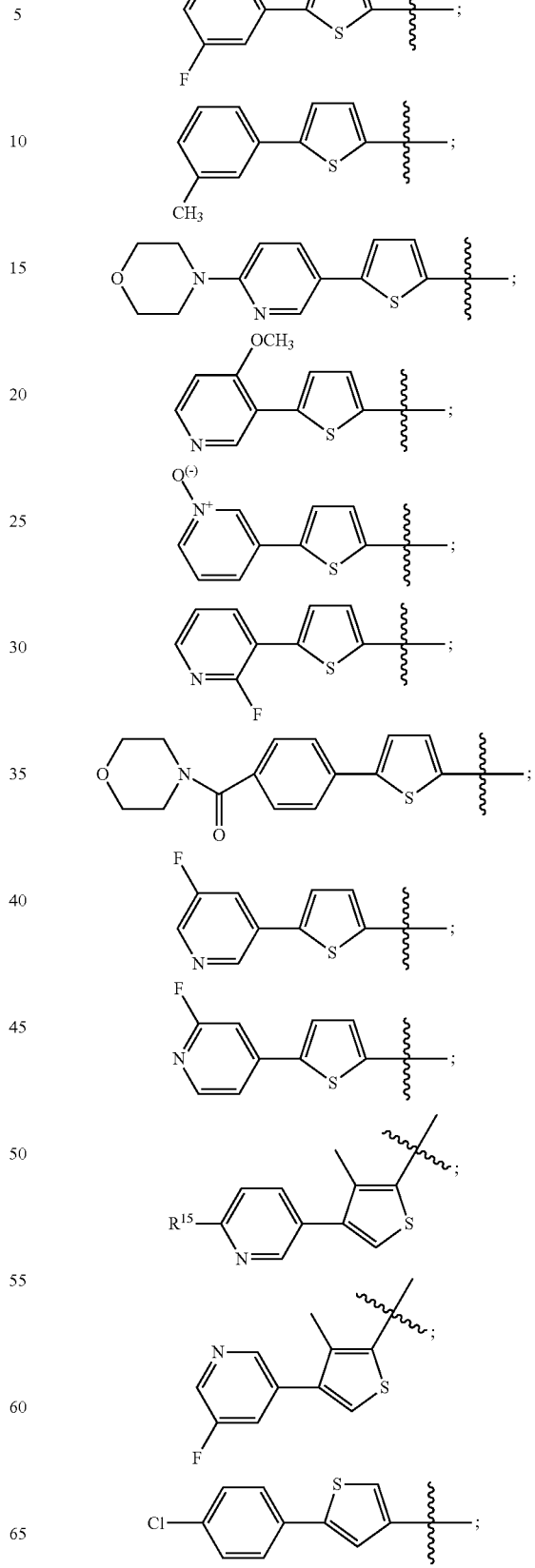

-continued

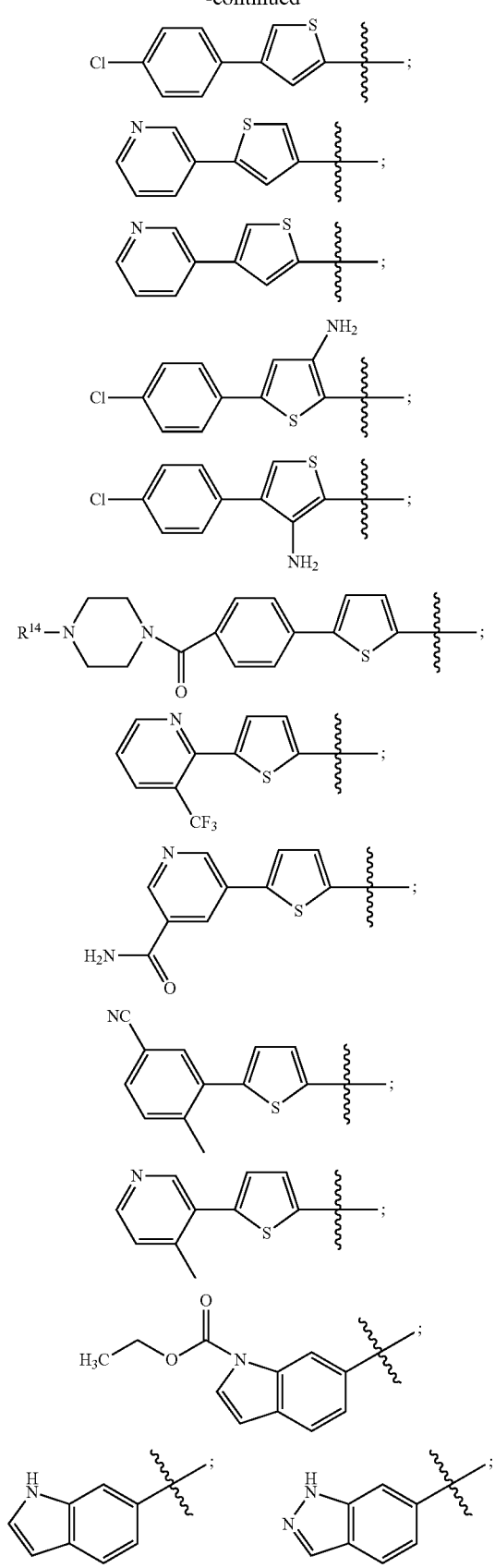

-continued

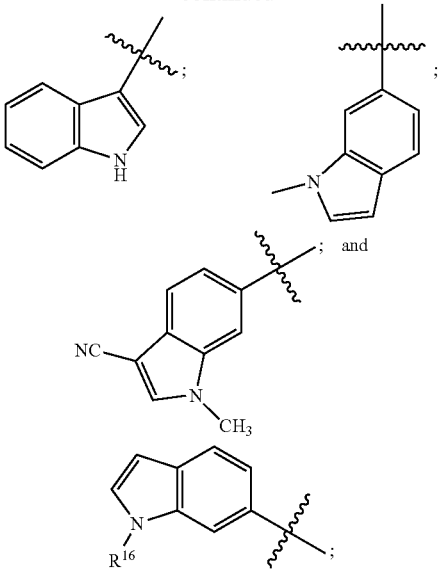

where:
R[10] is a member selected from the group consisting of —OH, —CH₃, —Cl, —F, NH₂, —CN, —CF₃, —N(CH₃)₂, —OCH₃, —CH₂OH, —NHSO₂CH₃, —SO₂NH₂, —CH₂N(CH₃)₂, —C(O)NHCH₃, —C(O)N(CH₃)₂, —C(O)NHCH(CH₃)₂, —C(O)NHCH₂CH₃, and —O—CH₂CH(OH)CH₂OH;

R[11] is a member selected from the group consisting of —OH, —Cl, —F, —CN, —CO₂H, —OCH₃, —NH₂, —CH₂OH, —N(CH₃)₂, —C(O)NHCH(CH₃)₂, and —OCH₂CH(OH)CH₂OH;

R[12] is a member selected from the group consisting of —CH₃, —CN and —F;

R[13] is a member selected from the group consisting of —H and —F;

R[14] is a member selected from the group consisting of —CH₃ and —C(O)OC(CH₃)₃;

R[15] is a member selected from the group consisting of —H and —F; and

R[16] is a member selected from the group consisting of —CH(CH₃)₂ and

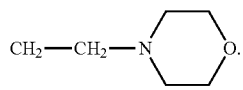

Another particular value for R[1] is a member included as R[1] in the formulas listed in Examples 1 to 126.

Yet another particular value for R[1] is a member included as R[1] in the formulas listed in Examples 127 to 225.

In yet another particular embodiment, R[3] is hydrogen or methyl.

In still another particular embodiment, R[4] is selected from the group consisting of optionally substituted C₁-C₄ alkyls, optionally substituted C₃-C₆ cycloalkyls, optionally substituted 5-6 membered heteroaryls having 1 or 2 heteroatoms selected from the group consisting of N and O (provided that only one O can be in the ring). A particular example of R[4] is cyclopropyl.

In a more particular embodiment, a group of compounds having preferential activity against the p38α may be found. The alpha selectivity can be seen, for example, using the p38 Assays described below.

In another embodiment the instant invention is directed to a pharmaceutical composition comprising at least one compound according to Formula I (including all of the subgroups and particular groups described above) and a pharmaceutically-acceptable carrier or diluent.

In still another embodiment, the present invention is for a method of treating an inflammatory disorder comprising administering to a patient in need of such treatment a pharmaceutical composition according to Formula I (including all of the subgroups and particular groups described above).

In yet another embodiment, the present invention is for a method of inhibiting p38 kinase in a mammal comprising administering to the mammal in need of such treatment at least one compound according to Formula I (including all of the subgroups and particular groups described above).

Utility

The compounds of the invention are selective inhibitors of p38 kinase activity, and in particular, isoforms p38α and p38 µl. Accordingly, compounds of Formula I have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an IC50 value for inhibiting p-38α/β kinase means that the compound has such effectiveness for inhibiting at least one of, or both of, p38α and p38β kinases. Additionally, certain compounds identified herein are selective for p38α, having, for example, at least 50-fold more active for p38α kinase as compared to p38β kinase. 100×≧200×

In view of their activity as inhibitors of p-38α/β kinase, compounds of Formula I are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

Particular examples of diseases that would benefit from p38 inhibitors are asthma, adult respiratory distress syndrome, chronic obstructive pulmonary disease, chronic pulmonary inflammatory disease, diabetes, inflammatory bowel disease, ulcerative colitis, Crohn's disease, osteoporosis, psoriasis, graft vs. host rejection, atherosclerosis, acute coronary disease, multiple myeloma, acute myelogenous leukemia, chronic myelogenous leukemia, pain, myocardial ischemia and arthritis including rheumatoid arthritis, psoriatic arthritis, traumatic arthritis, rubella arthritis, gouty arthritis and osteoarthritis, and especially rheumatoid arthritis and psoriasis.

The present invention thus provides methods for treating such conditions, comprising administering to a subject in need thereof an effective amount of at least one compound of Formula I or a salt thereof. The methods of treating p38 kinase-associated conditions may comprise administering compounds of Formula I alone or in combination with each other and/or other suitable therapeutic agents useful in treating such conditions. Exemplary of such other therapeutic agents include corticosteroids, rolipram, calphostin, CSAIDs, 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathioprine and cyclophosphamide;

TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of Formula I, including the compounds described in the examples hereof, have been tested in one or more of the assays described below and have shown activity as inhibitors of p38α/β enzymes and TNF-α.

Biological Assays

Generation of p38 Kinases

For this assay, cDNAs of human p38α, β, and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. (*Mol. Cell. Biol.*, 1247-1255 (1996)).

TNF-α Production by LPS-Stimulated PBMC's

Heparinized human whole blood was obtained from healthy volunteers. Peripheral blood mononuclear cells (PB- MCs) were purified from human whole blood by Ficoll-Hypaque density gradient centrifugation and resuspended at a concentration of $5\times10^6$/ml in assay medium (RPMI medium containing 10% fetal bovine serum). 50 µl of cell suspension was incubated with 50 µl of test compound (4× concentration in assay medium containing 0.2% DMSO) in 96-well tissue culture plates for 5 minutes at RT. 100 µl of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 µl prepared from three 20 µl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 µl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltiLex A scintillation wax (Wallac), and counted on a Microbeta scintillation counter Model 1450 (Wallac) Inhibition data were analyzed by nonlinear least-squares regression using Prizm (GraphPadSoftware). The final concentration of reagents in the assays are ATP, 1 µM; [$\gamma$-$^{33}$P]ATP, 3 nM; MBP (Sigma, #M1891), 2 µg/well; p38, 10 nM; and DMSO, 0.3%. One particular group of compounds of interest are those with both (1) an activity of <100 nm versus p38 alpha and (2) and a selectivity for alpha versus beta (for example, a 50-fold, 100-fold or 200-fold selectivity). The compounds in Examples 127-225 have at least a 50-fold alpha selectivity.

TNF-α Production by LPS-Stimulated Mice

Mice (Balb/c female, 6-8 weeks of age, Harlan Labs; n=8/treatment group) were injected intraperitoneally with 50 µg/kg lipopolysaccharide (LPS; *E. coli* strain 0111:B4, Sigma) suspended in sterile saline. Ninety minutes later, mice were sedated by $CO_2$:$O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

p38α Assay

The assays were performed in U-bottom 384-well plates. The final assay volume was 30 ul prepared from 15 ul additions of enzyme and substrates (fluoresceinated peptide and ATP) and test compounds in assay buffer (100 mM HEPES pH 7.2, 10 mM $MgCl_2$, 0.015% Brij35 and 4 mM DTT). The reaction was initiated by the combination of activated p38alpha with substrates and test compounds. The reaction was incubated at room temperature for 60 min. and terminated by adding 45 ul of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 20 uM; FL-P38a peptide, 1.5 uM; p38alpha, 6 nM; and DMSO, 1.6%.

p38β Assay

The assays were performed in U-bottom 384-well plates. The final assay volume was 30 ul prepared from 15 ul additions of enzyme and substrates (fluoresceinated peptide and ATP) and test compounds in assay buffer (100 mM HEPES pH 7.2, 10 mM $MgCl_2$, 0.015% Brij35 and 4 mM DTT). The reaction was initiated by the combination of activated p38beta with substrates and test compounds. The reaction was incubated at room temperature for 60 min. and terminated by adding 45 ul of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 20 uM; FL-P38b peptide, 1.5 uM; p38beta, 1 nM; and DMSO, 1.6%.

Abbreviations

For ease of reference, the following abbreviations are employed herein, including the methods of preparation and Examples that follow:
MeOH=methanol
EtOH=ethanol
EtOAc=ethyl acetate
Boc=tert-butyloxycarbonyl
CBZ=carbobenzyloxy or carbobenzoxy or benzyloxycarbonyl
DCM=dichloromethane
DCE=1,2-dichloroethane
DEAD=diethyl azodicarboxylate
DMF=dimethyl formamide
DMSO=dimethyl sulfoxide
PmB=para-methoxybenzyl
TFA=trifluoroacetic acid
THF=tetrahydrofuran
TMS=trimethylsilyl
p-TsOH=para-toluenesulphonic acid
HATU=O-(7-Azabenzotriazol-1-yl-N,N,N',N'-tetramethyluronim hexafluorophosphate
KOH=potassium hydroxide
$K_2CO_3$=potassium carbonate
$POCl_3$=phosphorous oxychloride
KOtBu=potassium t-butoxide
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
LiHMDS=lithium bis(trimethylsilyl)amide
NaH=sodium hydride
NaOEt=sodium ethoxide
NaOH=sodium hydroxide
$Na_2S_2O_3$=sodium thiosulfate
HCl=hydrogen chloride
NMP=N-methylpyrrolidinone
$CO_2$=carbon dioxide
Pd=palladium
Pd/C=palladium on carbon
sec=second (s)
min=minute(s)
h=hour(s)
L=liter
mL or ml=milliliter

23

μL=microliter
g=gram(s)
mg=milligram(s)
mol=moles
mmol=millimole(s)
N=Normal
M=Molar
° C.=degrees Celsius
rt=room temperature
Ret. time or $t_R$=retention time (minutes)
anhyd.=anhydrous
sat or sat'd=saturated
aq.=aqueous
HPLC=high performance liquid chromatography
LCMS=high performance liquid chromatography/mass spectrometry
MS=mass spectrometry
NMR=nuclear magnetic resonance
MHz=megahertz
s=singlet
m=multiplet
d=doublet
dd=doublet of doublet Methods of Preparation The compounds of Formula I may generally be prepared according to the following schemes and the knowledge of one skilled in the art. As shown below, each Scheme is followed by one or more Examples for making specific compounds using the disclosed Scheme.

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited are incorporated herein by reference in their entirety for the subject matter noted and for related subject matter.

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. The preparation of heterocycles useful to this invention are described in the series of books: *Comprehensive Heterocyclic Chemistry. The Structure, Reactions, Synthesis and Uses, of Heterocyclic Compounds*, First Edition Pergamon Press New York, publ., Katritzky, A. R., Rees, C. W., eds. (1984), and *Comprehensive Heterocyclic Chemistry II. A Review of the Literature 1982-1995. The Structure, Reactions, Synthesis and Uses of Heterocyclic Compounds*, Pergamon Press New York, publ. Katritzky, A. R., Rees, C. W. and Scriven, E. F., eds. (1996).

Acids or acid chlorides, used for the preparation of compounds useful to this invention may be commercially available or readily prepared by many methods known to one skilled in the art of organic chemistry and are described in Richard C. Larock, *Comprehensive Organic Transformations. A Guide to Functional Group Preparation*, VCH Publishers, Inc., publ., pp. 385-439 (1989).

EXAMPLES

The following Examples are offered as illustrative as a partial scope of the invention and are not meant to be limiting of the scope of the invention. Unless otherwise indicated, they have been prepared, isolated and characterized using the Schemes and other methods disclosed herein. The abbreviations used herein are defined above.

Unless otherwise indicated, the following HPLC conditions were used for the Examples: YMC S5 ODS 4.6×50 mm Ballistic column, 4 mL/min flow rate, 4 min. linear gradient elution (Start solvent % B=0; Final solvent % B=100), solvent A=10% MeOH/90% $H_2O$/0.2% $H_3PO_4$. Solvent B=90% MeOH/10% $H_2O$/0.2% $H_3PO_4$.

Examples 1 to 126

Schemes 1 to 12

Schemes 1 to 12 described in this application may be used to make the compounds noted therein. The definitions and abbreviations listed above are applicable unless otherwise noted.

Scheme 1

Compounds of the general structure c may be prepared according to Steps A or B in Scheme 1 below where $R^{20}$=C(O)NH—$R^4$.

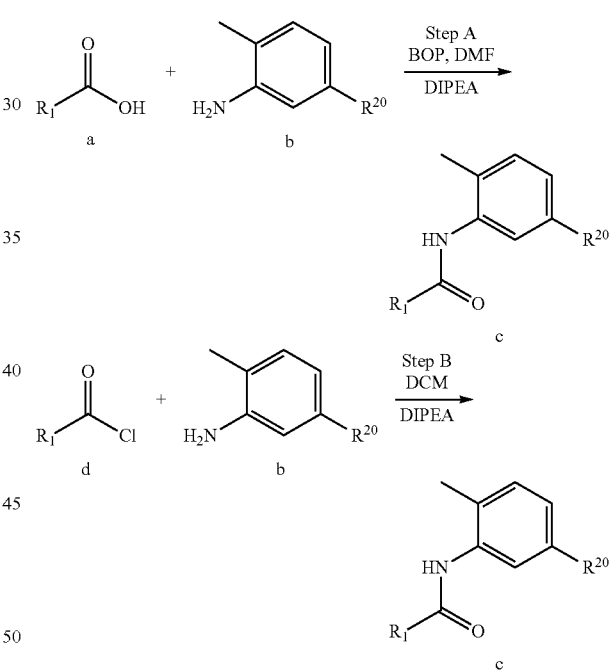

Step A

Carboxylic acid a and aniline b are dissolved in a polar aprotic solvent such as DMF. An amine base, such as DIPEA, and a coupling reagent, such as BOP are added. The reaction is stirred at room temperature or elevated temperature to afford product c.

Step B

Alternatively, carboxylic acid chloride d is reacted with aniline b in an aprotic solvent, such as DCM, in the presence of an amine base, such as DIPEA, to afford product c.

Scheme 2

Scheme 2 may be used where $R^{29}$ is H or n-propyl, $R^{30}$ is H or $CH_3$ and X=Cl, Br, I or another suitable leaving group.

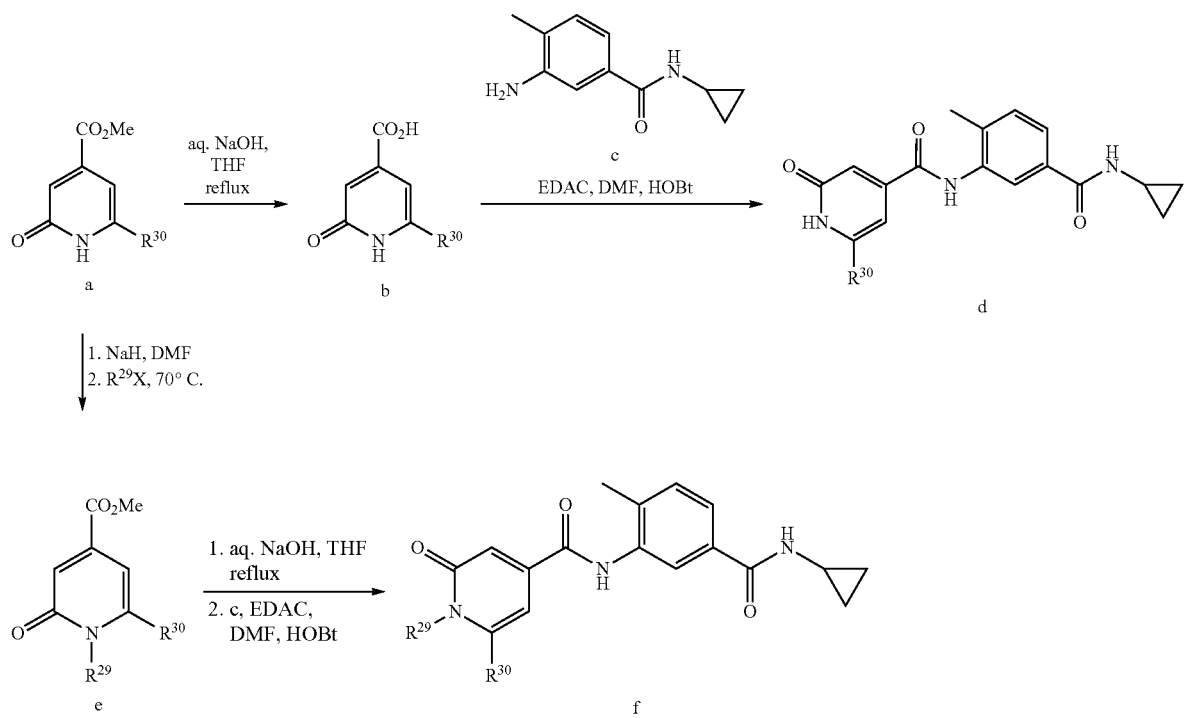
Scheme 3
Scheme 3 may be used where is $R^{31}$ is an optionally substituted alkyl, an optionally substituted cycloalkyl, an optionally substituted aryl, an optionally substituted heterocyclo or an optionally substituted heteroaryl.
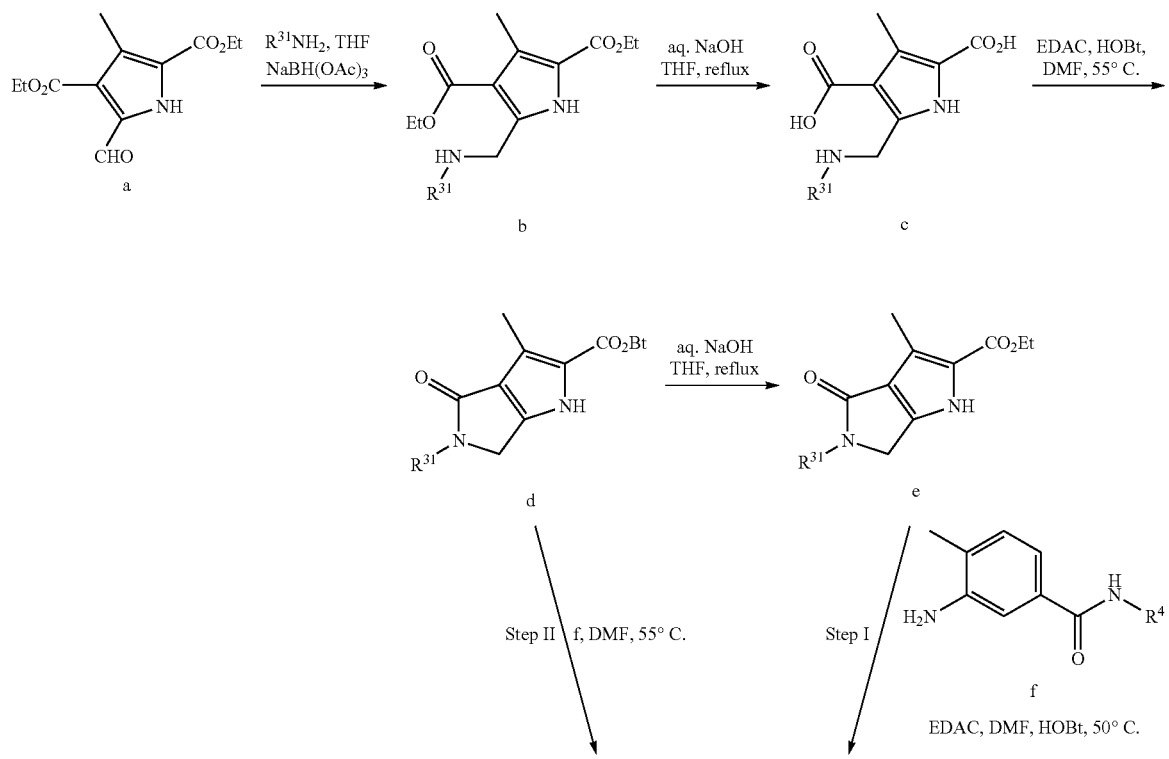

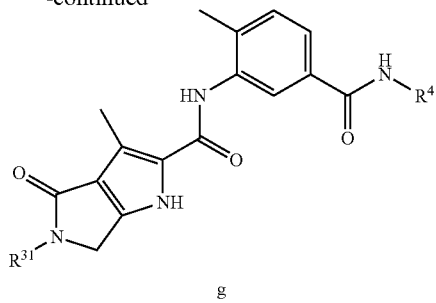

g

SCHEME 4
Synthesis of Pyrrole Based Inhibitors

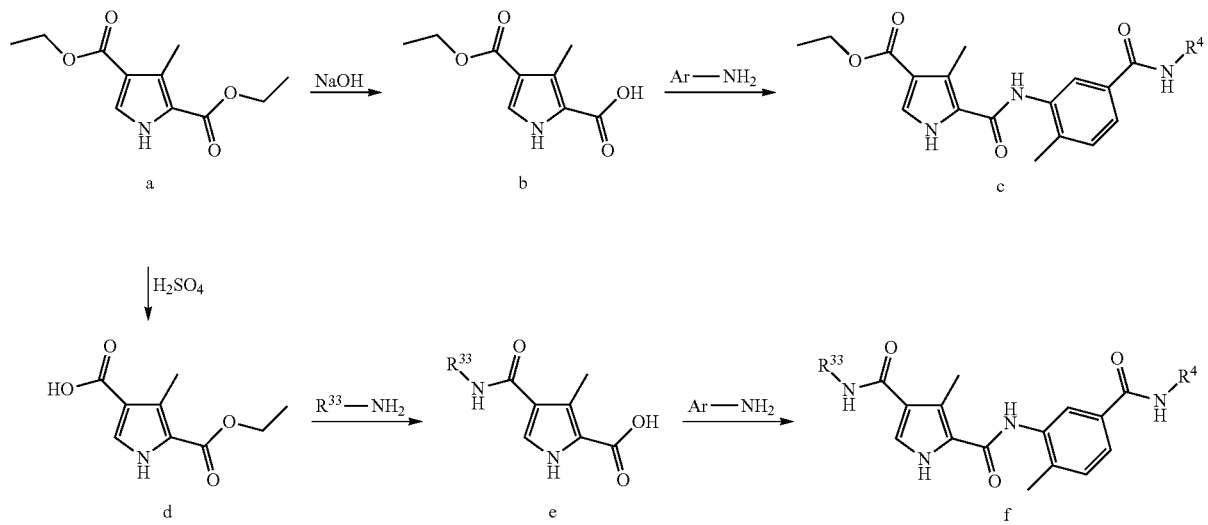

The various pyrrole based p38 kinase inhibitors can be prepared according to the procedures outlined in Scheme 4, where $R^{33}$ has the same definition as $R^{31}$. Diethyl-3-methyl-pyrrole-2,4-dicarboxylate can be hydrolyzed to the 4-monocarboxylic acid d with an acid such as $H_2SO_4$. Standard amide bond formation with an amine can afford the C-4 amide pyrrole e which, in turn, can be hydrolyzed to the C2-carboxylic acid and further elaborated to an amide via coupling with an aniline to afford compounds of the general structure f. The 2-monocarboxylic acid pyrrole b can be prepared from the diester via basic saponification which can then be coupled to an amine or aniline to afford compounds of the general structure c.

SCHEME 5
Synthesis of Pyrrolotriazinone Inhibitors

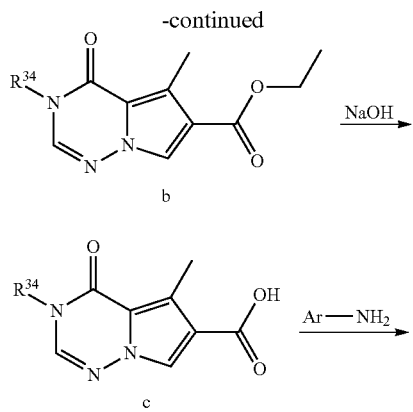

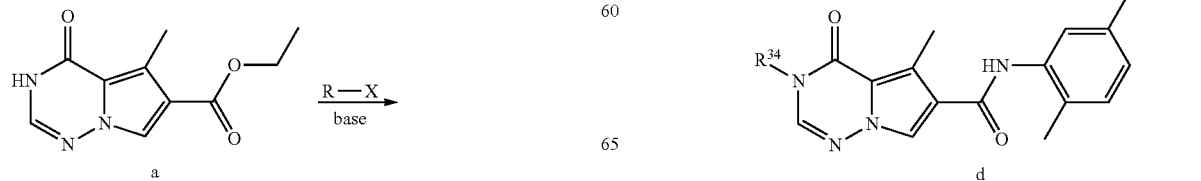

The pyrrolotriazinone-aniline p38 inhibitors can be prepared according to the methods outlined in Scheme 5, where $R^{34}$ has the same definition as $R^{31}$ and a suitable value for "aryl" is selected (for example as shown in the Examples). Pyrrolotriazinone a can be alkylated on N3 using a base and alkylating agent, such as propyl iodide, to give b. The C6 ester can be hydrolyzed to the acid with a hydroxide source, such as NaOH, to furnish c. Finally, acid c can be coupled to an aniline using standard amide bond forming conditions to furnish d.

SCHEME 6

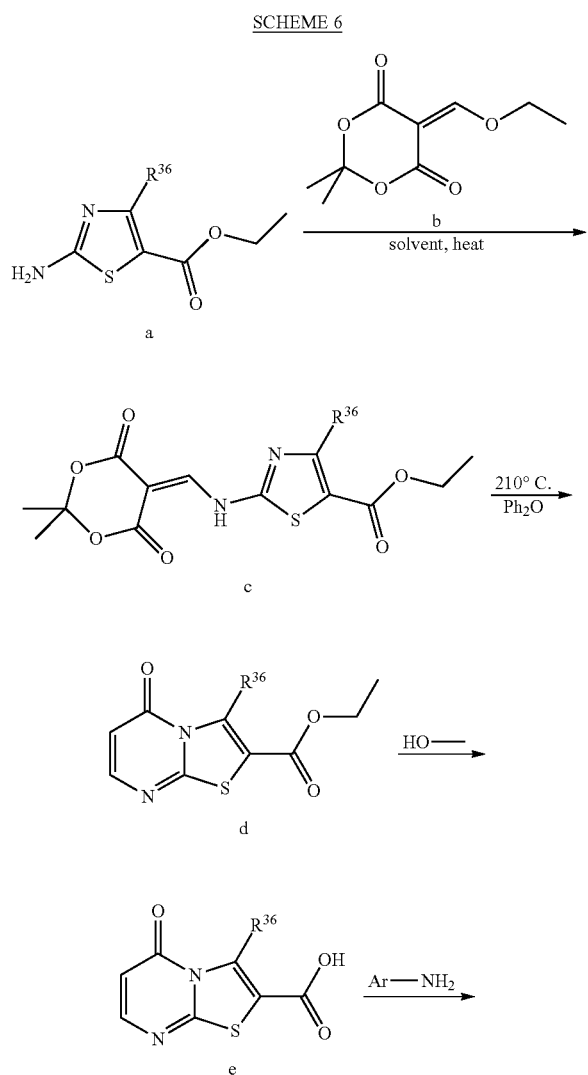

-continued

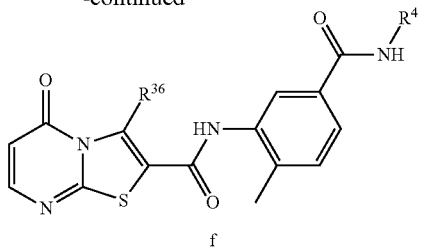

The fused thiazole-pyrimidinone p38 inhibitors can be prepared according to the general procedure outlined in Scheme 6 where $R^{36}$ has the same definition as $R^{31}$ and aryl has the same definitions as in Scheme 5 Aminothiazole a can be reacted with 5-(methoxymethylene)-2,2-dimethyl-1,3-dioxane-4,6-dione b in an appropriate solvent with heating to give c. The heating of c in a high boiling solvent, such as diphenyl ether, gives the 6,5-fused ring compound d. Ester d can be hydrolyzed to the carboxylic acid e with a hydroxide source, such as NaOH, which can then be coupled with an aniline to afford compounds of the general structure f.

SCHEME 7

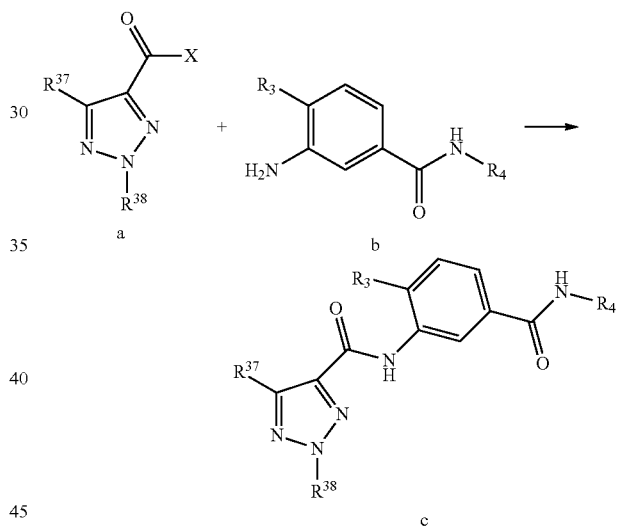

Compound c can be prepared as outlined in Scheme 7 by reacting acid halide a (where X=Cl or Br; $R^{37}$=H or $CH_3$; and $R^{38}$=the same values as described for $R^{31}$) with an aniline b in an inert solvent, such as dichloromethane or THF, in the presence of an organic base such as diisopropylethyl amine or triethyl amine or DBU to form c.

Alternatively c can be prepared by reacting carboxylic acid a (X=OH) with an aniline b under standard amide coupling conditions, e.g., EDC, HOBt, i-$Pr_2EtNH_2$, to form c.

SCHEME 8

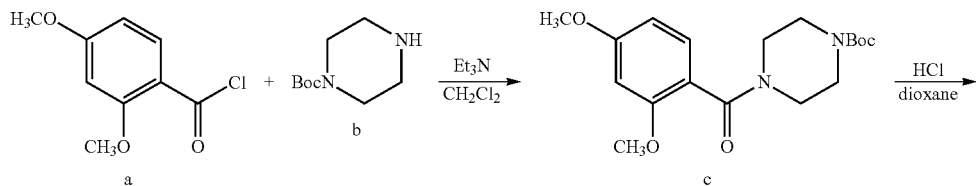

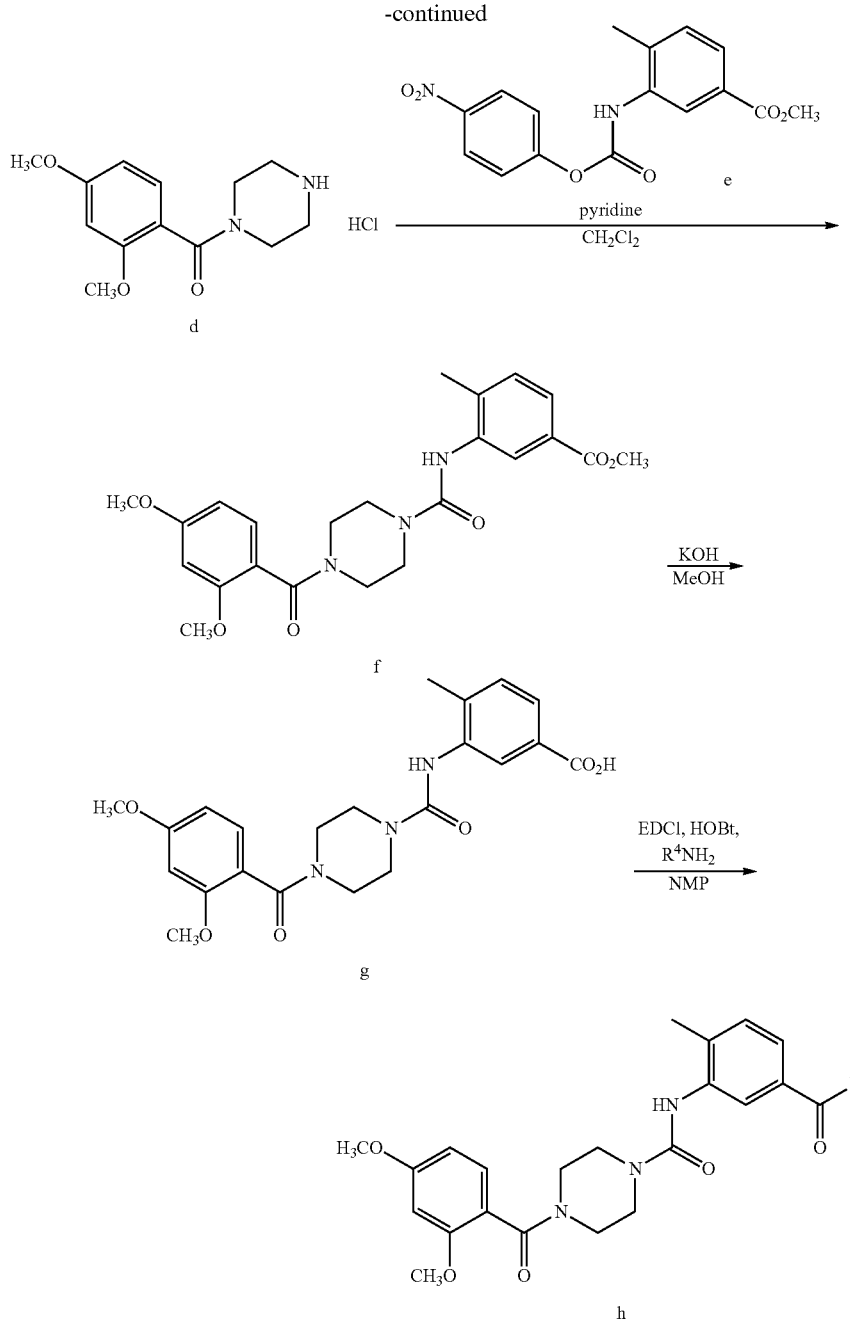

In Scheme 8, compound h can be prepared from the commercially-available compounds a and b. Compound a can be reacted with compound b in the presence of a base, such as triethylamine, in a solvent, such as dichloromethane, to afford compound c. Compound c can be reacted with an inorganic acid, such as hydrochloric acid, in a solvent, such as dioxane, to afford compound d. Compound d can be reacted with compound e in the presence of a base, such as pyridine, in a solvent, such as dichloromethane, to afford compound f. Compound f can be hydrolyzed in the presence of hydroxide, such as potassium hydroxide, in a solvent, such as methanol, to afford compound g. Finally, compound g can be reacted with an amine in the presence of a coupling reagent, such as EDCI and HOBt, and a base, such as diisopropylethylamine, in a solvent, such as NMP, to afford compound h.

SCHEME 9

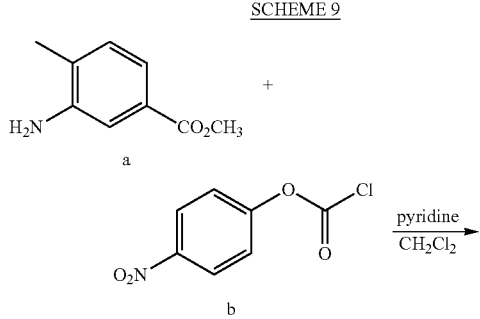

33

-continued

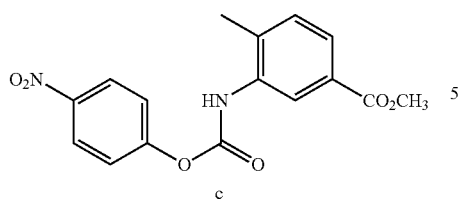

c

In Scheme 9, compound c can be prepared from the commercially-available compounds a and b using a base, such as pyridine, in a solvent, such as dichloromethane.

SCHEME 10

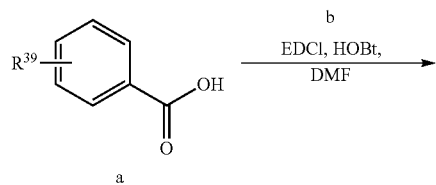

b

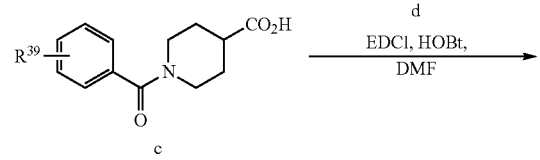

d

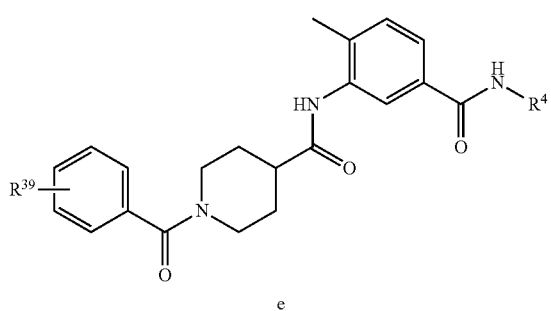

e

For Scheme 10, compound e can be prepared from the commercially available compounds a and b as depicted in Scheme 10 where $R^{39}$ has the same values as defined for $R^{31}$. Compound a can be reacted with compound b in the presence of coupling reagents, such as EDCI and HOBt, in a solvent, such as dimethylformamide, to afford compound c. Compound c can be reacted with compound d in the presence of coupling reagents, such as EDCI and HOBt, in a solvent, such as dimethylformamide, to afford compound e.

34

SCHEME 11

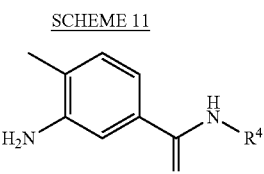

b

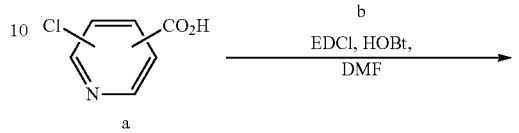

a

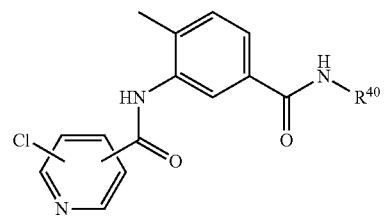

c

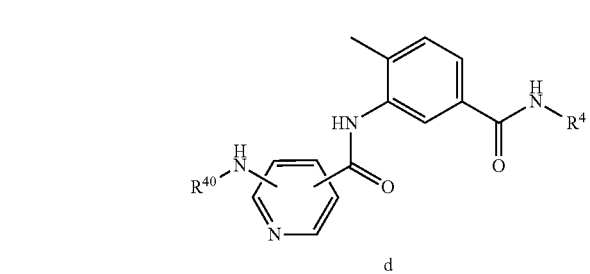

d

For Scheme 11, compound d can be prepared from compounds a and b as depicted in Scheme 11 where $R^{40}$ has the same values as defined for $R^{31}$. Commercially available compound a can be reacted with compound b in the presence of coupling reagents, such as EDCI and HOBt, in a solvent, such as dimethylformamide, to afford compound c. Compound c can be reacted with amines ($RNH_2$) in a solvent, such as N-methylpyrrolidinone, to afford compound d.

SCHEME 12

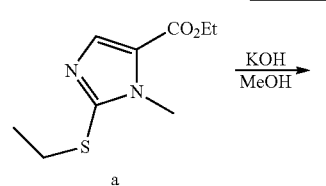

a

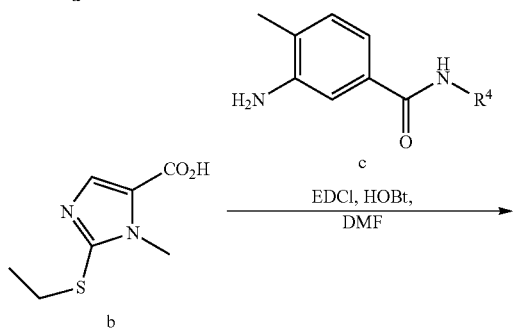

b

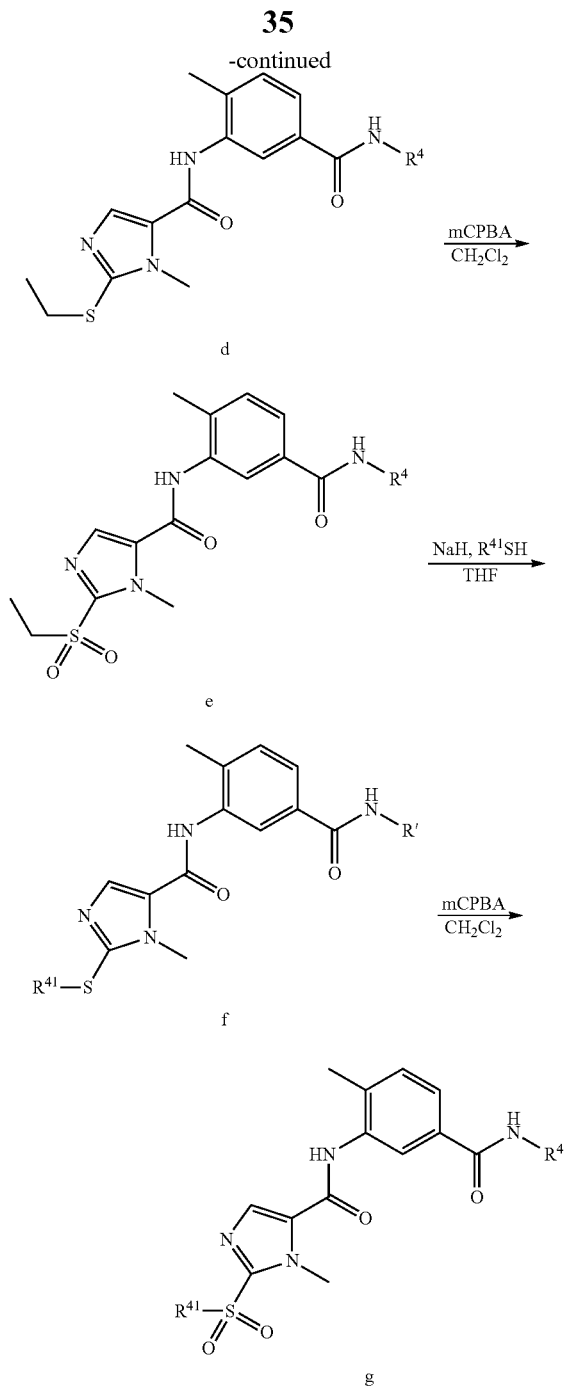

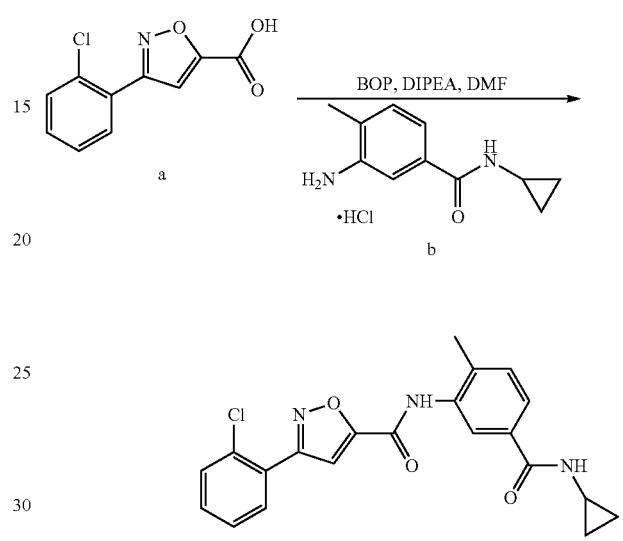

oxidant, such as m-chloroperbenzoic acid, in a solvent, such as dichloromethane, to afford compound g.

Example 1

Method 1

To a solution of 3-(2-chlorophenyl)isoxazole-5-carboxylic acid a (45 mg, 0.20 mmol) in DMF (0.5 mL) was added 3-amino-N-cyclopropyl-4-methylbenzamide b (50 mg, 0.22 mmol), BOP (111 mg, 0.25 mmol), and DIPEA (0.087 mL, 0.5 mmol). The reaction was stirred at room temperature for 3 h, then heated to 70° C. for an additional 1 h. Upon cooling to room temperature, water (4 mL) was added and the resulting precipitate was collected by vacuum filtration. The crude solid was further purified by reverse phase preparative HPLC to afford Example 1 (also called Compound 1) as an off-white solid (44 mg). HPLC ret. time: 3.20 min. LCMS [M+H]$^+$= 396.3, 398.3

Example 2

Method 2

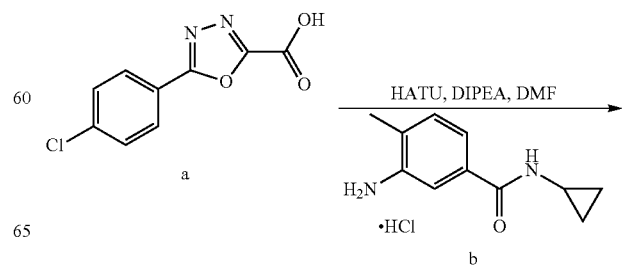

For Scheme 12, compound g can be prepared from commercially available compound a as depicted in Scheme 12 where $R^{41}$ has the same values as defined for $R^{31}$. Compound a can be hydrolyzed with aqueous hydroxide, such as potassium hydroxide, in a solvent, such as methanol, to afford compound b. Compound b can be reacted with compound c in the presence of coupling reagents, such as EDCI and HOBt, in a solvent, such as dimethylformamide, to afford compound d. Compound d can be oxidized with an oxidant, such as m-chloroperbenzoic acid, in a solvent, such as dichloromethane, to afford compound e. Compound e can be reacted with a thiol (RSH) in the presence of a base, such as sodium hydride, in a solvent, such as tetrahydrofuran, to yield compound f. Finally, compound f can be oxidized with an -continued

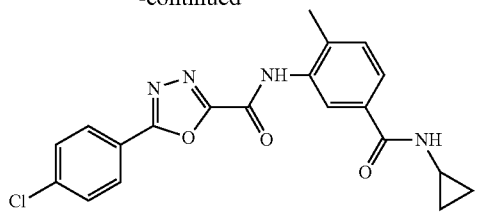

2

To a solution of 5-(4-chlorophenyl)-1,3,4-oxadiazole-2-carboxylic acid a (45 mg, 0.20 mmol) in DMF (0.5 mL) was added 3-amino-N-cyclopropyl-4-methylbenzamide b (50 mg, 0.22 mmol), HATU (95 mg, 0.25 mmol), and DIPEA (0.105 mL, 0.6 mmol). The reaction was stirred at 80° C. for 1 h. Upon cooling to room temperature, water (4 mL) was added and the resulting precipitate was collected by vacuum filtration to afford Example 2 (also called Compound 2) as an off-white solid (51 mg). HPLC ret. time: 3.17 min. LCMS [M+H]$^+$=397.3, 399.3.

Examples 3 to 9

The Examples 3 to 9 shown in Table 1 were prepared in a manner analogous to the above Examples 1 and 2.

TABLE 1

| Example No. | Structure | Method (Example No.) | HPLC r.t. (min.) | MW | MS (MH+) |
|---|---|---|---|---|---|
| 3 | 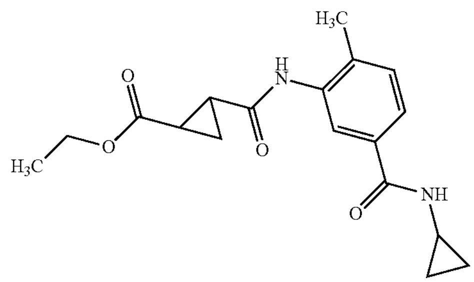 [SMILES: CCOC(=O)C1CC1C(=O)Nc1cc(C(=O)NC2CC2)ccc1C] | 2 | 2.56 | 330.39 | 333.1 |
| 4 | 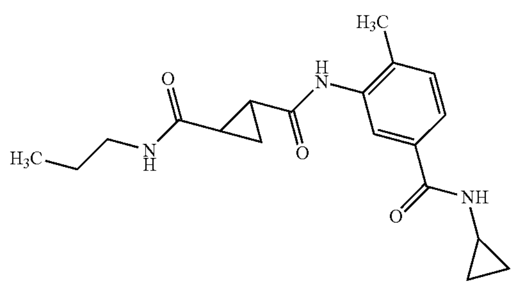 [SMILES: CCCNC(=O)C1CC1C(=O)Nc1cc(C(=O)NC2CC2)ccc1C] | 2 | 2.31 | 343.43 | 344.2 |
| 5 | 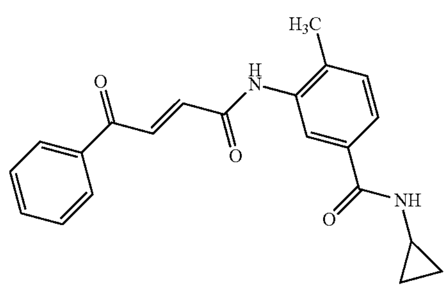 [SMILES: Cc1ccc(C(=O)NC2CC2)cc1NC(=O)/C=C/C(=O)c1ccccc1] | 1 | 2.89 | 348.41 | 349.1 |
| 6 | 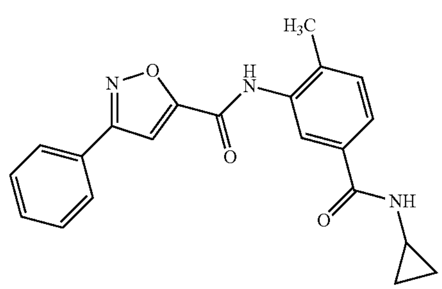 [SMILES: Cc1ccc(C(=O)NC2CC2)cc1NC(=O)c1cc(-c2ccccc2)no1] | 1 | 3.04 | 361.4 | 362.2 |

TABLE 1-continued

| Example No. | Structure | Method (Example No.) | HPLC r.t. (min.) | MW | MS (MH+) |
|---|---|---|---|---|---|
| 7 | 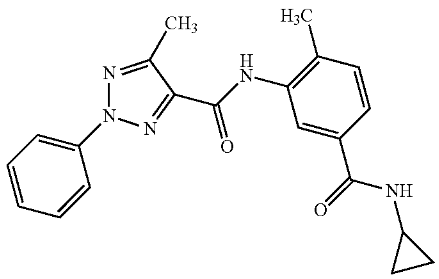 [SMILES: Cc1ccc(C(=O)NC2CC2)cc1NC(=O)c1nn(-c2ccccc2)nc1C] | 2 | 3.5 | 375.43 | 376.1 |
| 8 | 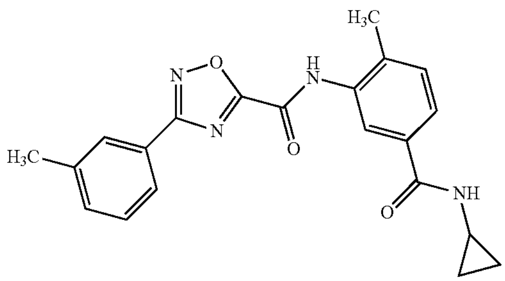 [SMILES: Cc1cccc(-c2noc(C(=O)Nc3cc(C(=O)NC4CC4)ccc3C)n2)c1] | 2 | 3.35 | 376.42 | 377.1 |
| 9 | 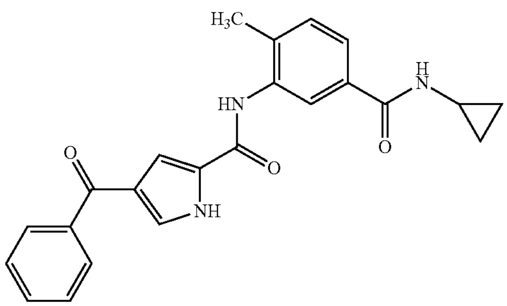 [SMILES: Cc1ccc(C(=O)NC2CC2)cc1NC(=O)c1cc(C(=O)c2ccccc2)c[nH]1] | 2 | 2.83 | 387.44 | 388.1 |

Example 10

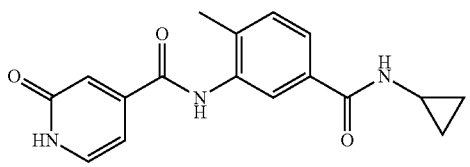

Step A

A solution of a (Scheme 2) (R³⁰=H); 0.234 g, 1.59 mmol, 1.0 eq.), THF (3.2 mL) and aqueous NaOH (1 N, 6.4 mL, 6.4 mmol, 4.0 eq.) was refluxed overnight. After cooling to room temperature, the reaction mixture was concentrated in vacuo but not to dryness. At 0° C., aqueous HCl (3 N) was added until pH was equal to about 3 as determined by litmus paper. The aqueous layer was extracted with CH₂Cl₂ (3×) and EtOAc (3×). The organic layers were combined, dried over Na₂SO₄, filtered and concentrated in vacuo to give b (Scheme 2) as an orange solid (0.0696 g, 32% yield). HPLC RT=0.377 min (94%, 220 nm); LC/MS (MH)=139.99.

Step B

A solution of b (Scheme 2) (0.0696, 0.50 mmol, 1.0 eq.), c (Scheme 2) (0.115 g, 0.06 mmol, 1.2 eq.), EDAC (0.146 g, 0.76 mmol, 1.5 eq.), HOBt (0.103 g, 0.76 mmol, 1.5 eq.) and DMF (1.0 mL) was stirred under nitrogen overnight. The reaction was diluted with water and EtOAc, and the layers were separated. The aqueous layer was extracted with EtOAc (4×). The organic layers were combined, dried over Na₂SO₄, filtered and concentrated in vacuo to a yellow oil which was subjected to autoprep. The appropriate fractions were collected and lyophilized to give Compound 10 (d in Scheme 2) (also called Example 10) as an off-white solid (0.040 g, 25% yield). HPLC RT=1.717 min (97%, 220 nm); LC/MS (MH)= 312.79.

Example 11

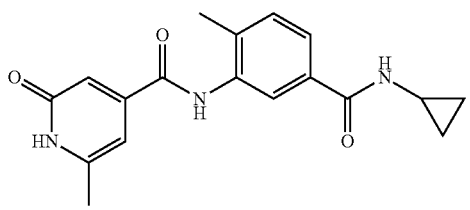

In a similar sequence, Example 11 (also called Compound 11) (d in Scheme 2, wherein R²⁹=H and R³⁰=CH₃) was obtained as a white solid. HPLC RT=1.937 min (95%, 220 nm); LC/MS (MH)=326.16.

Example 12

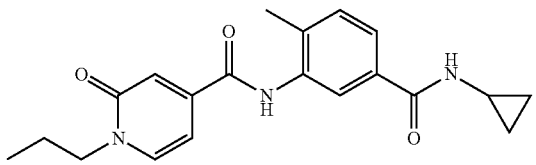

Step A

To a solution of a (Scheme 2) ($R^{30}$=H, 0.166 g, 1.1 mmol, 1.0 eq.) in DMF (1.2 mL) under nitrogen at 0° C. was added NaH (95% in mineral oil, 0.0601 g, 2.4 mmol, 2.2 eq.). The cold bath was removed, and the reaction was stirred for 5 min. to room temperature. n-Propylamine was added, and the solution was heated at 70° C. After 3.5 h, the reaction was cooled to room temperature and diluted with EtOAc and water. After separation of the layers, the aqueous layer was extracted with EtOAc (2×). The organic layers were combined, dried over $Na_2SO_4$, filtered and concentrated in vacuo. After autoprep, the appropriate fractions were collected to give e as a white solid (0.032 g, 15% yield). HPLC RT=1.930 min (100%, 220 nm); LC/MS (MH)=196.09.

Step B

In a similar sequence as that for d in Scheme 2, Example 12 (also called Compound 12) (f in Scheme 2, wherein $R^{29}$=n-propyl and $R^{30}$=H) was obtained as a white solid. HPLC RT=2.277 min (100%, 220 nm); LC/MS (MH)=354.08.

Example 13

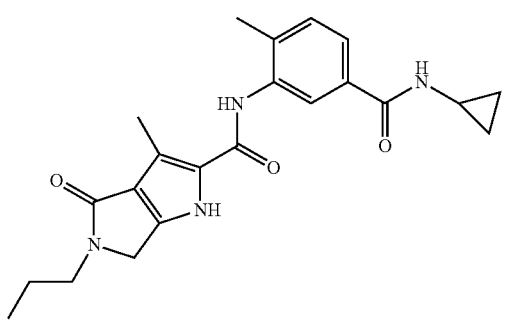

Step A

To a solution of a (Scheme 3) (3.17 g, 12.5 mmol, 1.0 eq.) and n-propylamine (1.1 mL, 13.4 mmol, 1.1 eq.) in THF (50 mL) under nitrogen was added $NaBH(OAc)_3$ (4.07 g, 19.2 mmol, 1.5 eq.). After stirring overnight, the reaction mixture was concentrated in vacuo, and the residue was diluted with $CH_2Cl_2$ and water. After separation of the layers, the aqueous layer was extracted with $CH_2Cl_2$, and the organic layers were combined, washed with saturated aqueous $NaHCO_3$, dried over $Na_2SO_4$, filtered and concentrated in vacuo. Silica gel chromatography using $CH_2Cl_2$:MeOH (20:1) as eluent and afforded b ($R^{31}$=n-propyl and $R^4$=cyclopropyl) as a light yellow solid (2.43 g, 66%). HPLC RT=2.393 min (100%, 220 nm); LC/MS (MH)=297.00.

Step B

A solution of b (2.43 g, 8.2 mmol, 1.0 eq.), THF (16 mL) and aqueous NaOH (1 N, 35 mL, 35 mmol, 4.3 eq.) was refluxed overnight. After cooling to room temperature, the reaction mixture was concentrated in vacuo not to dryness. At 0° C., aqueous HCl (6 N) was added until the pH was equal to about 5 as measured by litmus paper. The precipitate was collected, washed with water and dried to give c as a white solid (1.78 g, 90% yield). HPLC RT=1.023 min (96%, 220 nm); LC/MS (MH)=241.12.

Step C

A solution of c (0.91 g, 3.8 mmol, 1.0 eq.), EDAC (1.6 g, 8.4 mmol, 2.2 eq.), HOBt (1.1 g, 8.4 mmol, 2.2 eq.) and DMF (200 mL) was heated under nitrogen at 55° C. After 0.5 h, the reaction mixture was cooled to room temperature, and the solvent was removed by distillation. The residue was dissolved in $CH_2Cl_2$, washed successively with water and aqueous saturated $NaHCO_3$, dried over $Na_2SO_4$, filtered and concentrated in vacuo. Trituration with $Et_2O$ afforded crude d as a tan solid which was used without further purification. HPLC RT=2.850 min (84%, 220 nm); LC/MS (MH)=350.15.

Step D

In a similar sequence as that for c, e was obtained as a tan solid (0.16 g, 48% yield). HPLC RT=1.920 min (93%, 220 nm); LC/MS (MH)=223.02.

Step E (Step I in Scheme 3)

A solution of e (0.071 g, 0.32 mmol, 1.0 eq.), f (0.075 g, 0.40 mmol, 1.2 eq.), EDAC (0.094 g, 0.49 mmol, 1.5 eq.), HOBt (0.067 g, 0.49 mmol, 1.5 eq.) and DMF (0.6 mL) was stirred under nitrogen overnight. The reaction mixture was then heated at 50° C. and stirred overnight. After cooling to room temperature, MeOH was added, and the reaction mixture was subjected to autoprep. The appropriate fractions were collected, and at 0° C., $NaHCO_3$ (s) was added until the pH was equal to about 11 as determined by litmus paper. The precipitate was collected, washed with water and dried to give Example 13 (also called Compound 13) (g in Scheme 3, wherein $R^{31}$=n-propyl, and $R^4$=cyclopropyl) as a white solid (0.036 g, 28% yield). HPLC RT=2.597 min (100%, 220 nm); LC/MS (MH)=395.21.

Example 14

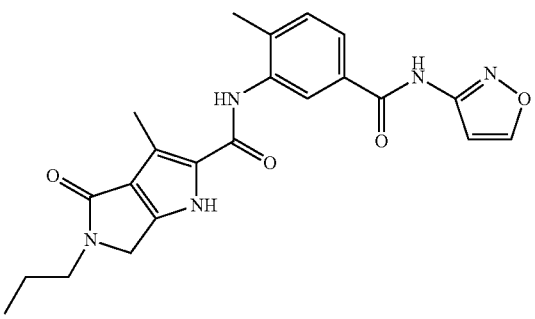

Step A (Step II in Scheme 3)

For this Example $R^4$=isoxazole and $R^{31}$=n-Pr. A solution of d (0.103 g, 0.30 mmol, 1.0 eq.) and f (0.103 g, 0.48 mmol, 1.6 eq.) in DMF (0.6 mL) was mechanically shaken at 50° C. for two days. After cooling to room temperature, MeOH was added, and the reaction mixture was subjected to autoprep. The appropriate fractions were collected, and at 0° C., NaHCO₃ (s) was added until the pH was equal to about 11 as determined by litmus paper. The precipitate was collected, washed with water and dried to give Example 14 (also called Compound 14) as a white solid (0.017 g, 13% yield). HPLC RT=2.763 min (100%, 220 nm); LC/MS (MH)=422.13.

Examples 15 to 18

For Examples, 15 to 18, Scheme 3 was used, with appropriate values for the materials.

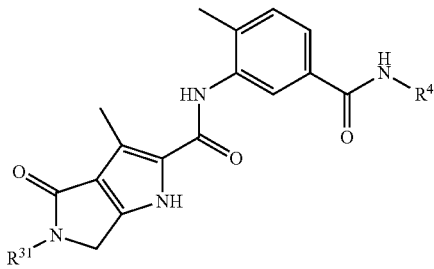

Using Step II in Scheme 3, the following compounds were obtained:

Example 15

($R^{31}$=ethyl, $R^4$=cyclopropyl): HPLC RT=2.427 min (93%, 220 nm); LC/MS (MH)=381.21.

Example 16

($R^{31}$=ethyl, $R^4$=isoxazole): HPLC RT=2.533 min (<100%, 220 nm); LC/MS (MH)=408.15.

Example 17

($R^{31}$=ethyl, $R^4$=methyl): HPLC RT=2.207 min (99%, 220 nm); LC/MS (MH)=355.14.

Example 18

($R^{31}$=ethyl, $R^4$=ethyl): HPLC RT=2.350 min (98%, 220 nm); LC/MS (MH)=369.21.

Example 19

For Example 19, Scheme 4 was used with appropriate substitutions.
Step A

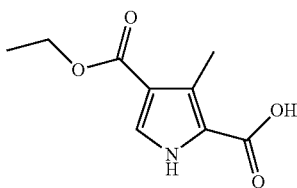

The material b was prepared according to the method of Corwin: see Corwin, A. H., Viohl, P., *J. Am. Chem. Soc.*, 1137 (1944).

Step B

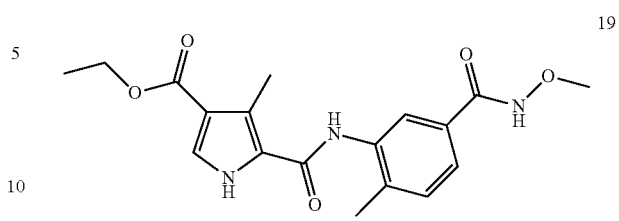

In acid b (63 mg, 0.32 mmol), EDC (74 mg, 0.38 mmol), HOBt (52 mg, 0.38 mmol) and 2-methyl-5-(methoxyamido) aniline hydrochloride (95 mg, 0.44 mmol) in a resealable vial was added DMF (1.5 mL) and DIPEA (0.12 mL, 0.7 mmol). The vial was sealed and heated at 60° C. for 20 h. The reaction solution was cooled and partitioned between EtOAc (10 mL) and water (5 mL). The layers were separated, and the organic layer dried over Na₂SO₄, filtered, and concentrated to an oil. The product was purified by preparative TLC to afford Example 19 (also called Compound 19) (17.7 mg). HPLC $t_R$=3.21 min, 99.3% purity. LCMS: m/z calculated for $C_{18}H_{21}N_3O_5$ [M+H]⁺: 360.2. Found: 360.2.

Example 20

Scheme 4

Step A

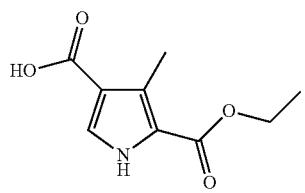

Diethyl-3-methyl-pyrrole-2,4-dicarboxylate as a (4.13 g) was dissolved in 10 mL H₂SO₄ and stirred overnight at room temperature. The solution was poured into ice water (20 mL) with stirring. The resulting solids were filtered and rinsed with water to give d (2.67 g) after drying.
Step B

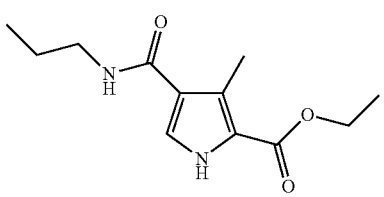

Acid d (0.95 g, 4.8 mmol), EDC (1.01 g, 5.3 mmol), HOBt (0.71 g, 5.3 mmol) was added in DMF (4 mL) and DIPEA (1.25 mL, 7.2 mmol). After stirring for 1 h, propylamine (0.6 mL, 7.2 mmol) was added and the reaction solution stirred for 3 h. Water was added and the resulting solids were collected by filtration and washed with water to give e (750 mg) after drying.

Step C

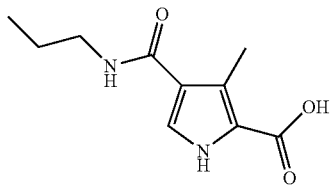

To a solution of d (750 mg) in THF (2 mL) was added 2 N NaOH (2 mL) and the mixture was then heated at 60° C. for 5 h. The THF was removed on a rotovap and the resulting solution adjusted to pH 4 with 1 N HCl. The precipitated solids were collected and washed to give the acid e (246 mg).

Step D

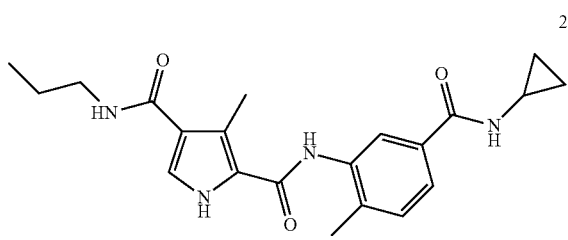

In a solution of acid e (16 mg, 0.07 mmol) in NMP (0.3 mL) was added HATU (32 mg, 0.08 mmol) and 3-amino-N-cyclopropyl-4-methyl-benzamide (29 mg, 0.15 mmol) and then heated at 50° C. for 20 h. The product was purified directly by preparative HPLC to give Example 20 (also called Compound 20) (f, 6 mg). HPLC $t_R$=3.02 min, 94% purity. LCMS: 383.2 (M+H).

Example 21

Scheme 5

Step A

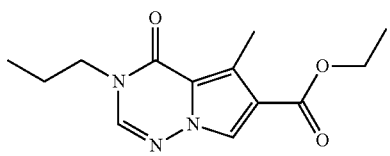

To a solution of pyrrolotriazinone as a (606 mg, 2.5 mmol) in DMF (6 mL) was added $Cs_2CO_3$ (1.01 g, 3.1 mmol) and n-propyl iodide (0.3 mL, 3.1 mmol) and the reaction mixture stirred for 3 h. Water (30 mL) was added dropwise via addition funnel and the resulting solids stirred for 15 minutes, filtered and rinsed with water. The crude solid was used directly in the next step.

Step B

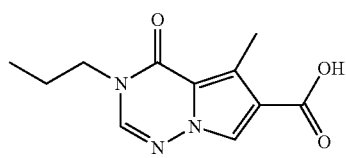

To the ester b (2.5 mmol) was added MeOH (5 mL) and 1N NaOH (5 mL) and the solution was heated at 60° C. for 18 h. The reaction was cooled to room temperature and the MeOH removed in vacuo. The resulting solution was further diluted with water (5 mL) and neutralized with 1N HCl (5 mL). The precipitated solids were filtered and rinsed with water to give the crude acid c (450 mg, 77% yield, 2 steps).

Step C

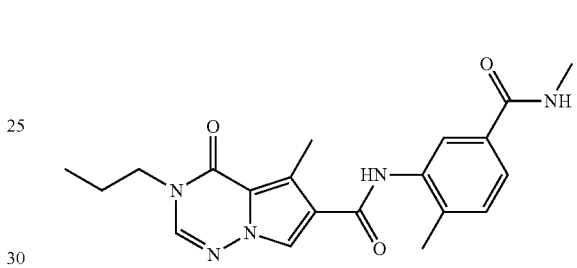

To a solution of the acid c (1 equiv), EDC (1.2 equiv), HOBt (1.2 equiv) in DMF (0.43M) was added an aniline (1.2 equiv) and the reaction was heated at 60-65° C. for 20 h. The reactions were cooled to room temperature, water (4 volumes) was added and the resulting solids were stirred for 4 h, filtered and rinsed with water to give the pure Example 21 (also called Compound 21) (d, 18.7 mg, 48% yield)). HPLC $t_R$=3.16 min, 99% purity. LCMS: m/z Calcd for $C_{20}H_{23}N_5O_3$ [M+H]$^+$: 382.18. Found: 382.2.

Examples 22 to 28

For Examples 22 to 28 a procedure similar to Example 21 was used with the values for $R^{50}$ as listed in the table. More generally, $R^{50}$ can be selected from the group defined for $R^{31}$.

TABLE 2

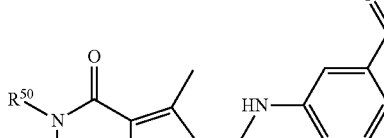

| Example No. | $R^{50}$ | $R^4$ | Data MS/HPLC |
|---|---|---|---|
| 22 | —$CH_2$—$CH_2$—$CH_3$ | —$CH_2$—$CH_3$ | 396.2/3.29 min |
| 23 | —$CH_2$—$CH_2$—$OCH_3$ | —$CH_2$—$CH_3$ | 412.2/3.09 min |
| 24 | —$CH_2$—$CH_2$—$CH_3$ | H | 368.2/3.06 min |
| 25 | —$CH_2$—$CH_2$—$CH_3$ | —$CO_2$—$CH_2$—$CH_3$ | 465.3/3.36 min |
| 26 | —$CH_2$—$CH_2$—$CH_3$ | —$CO_2$—$CH_3$ | 426.2/3.26 min |

TABLE 2-continued

| | | | |
|---|---|---|---|
| 27 | —CH₂—CH₂—CH₃ | cyclopropyl | 408.4/3.36 min |
| 28 | —CH₂-(2-pyridyl) | cyclopropyl | 457.3/2.88 min |

Example 29

Scheme 6

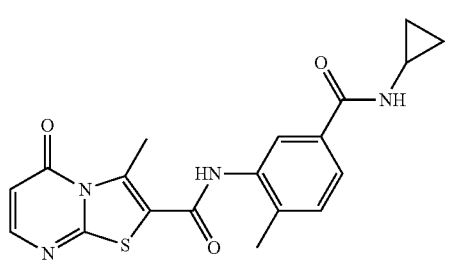

Step A

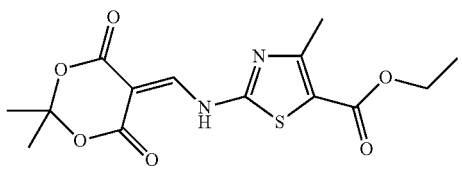

A solution of ethyl 2-aminothiazole-4-methyl-5-carboxylate as a (210 mg, 1.13 mmol) and 5-(methoxymethylene)-2,2-dimethyl-1,3-dioxane-4,6-dione as b (213 mg, 1.13 mmol) in MeCN (3 mL) was heated at 70° C. for 90 min. The solution was then cooled to room temperature and the MeCN removed in vacuo. Ether (5 mL) was added then hexane (2 mL) and the resulting slurry stirred for 5 min then filtered. The solids were washed with hexane (2×3 mL) and dried on a filter to give c as a tan solid (231 mg, 60% yield). HPLC $t_R$=3.66 min, 96% purity; LCMS 341.1 (M+H).

Step B

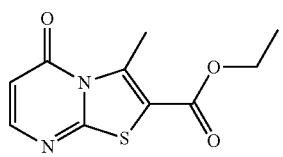

A suspension of c (154 mg) in diphenylether (1.5 mL) was heated to 200-210° C. for 25 min. The reaction began to evolve $CO_2$ around 200° C. The solution was cooled and purified directly by column chromatography (10% to 35% EtOAc/hexane) to give d (67 mg, 62% yield). LCMS 239.04 (M+H).

Step C

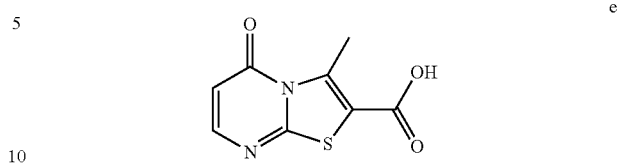

To a solution of d (62 mg, 0.26 mmol) in MeOH (0.4 mL) and THF (0.4 mL) was added 1N NaOH (0.4 mL, 0.39 mmol) and the solution stirred at rt for 30 minutes upon which solids had precipitated. pH 7 buffer (0.8 mL) was added and the reaction vessel cooled in an ice bath and added 1 N HCl (0.4 mL). The solution was concentrated and the product extracted from the salts with hot EtOAc and was used without further purification.

To a solution of acid e (19.5 mg, 0.09 mmol) and 3-amino-N-cyclopropyl-4-methyl-benzamide hydrochloride (25 mg, 0.11 mmol) in NMP (0.4 mL) was added HATU (42.4 mg, 0.11 mmol) and DIPEA (0.02 mL, 0.11 mmol) and the solution heated to 75° C. for 4 h. The crude reaction mixture was purified by preparative HPLC to give Example 29 (also called Compound 29) (12.6 mg, 35% yield). HPLC $t_R$=2.83 min, 99.0% purity; LCMS 383.1 (M+H).

Examples 30 to 31

Compounds for Examples 30 to 31 in Table 3 below were made using the process described in Scheme 6, similar to Example 29 above.

TABLE 3

| Example No. | R¹ | R⁴ | Data MS/HPLC |
|---|---|---|---|
| 30 | H | cyclopropyl | 369.1/2.82 min |
| 31 | H | 3-methyl-isoxazol-5-yl | 396.1/2.94 min |

Example 32

Scheme 1

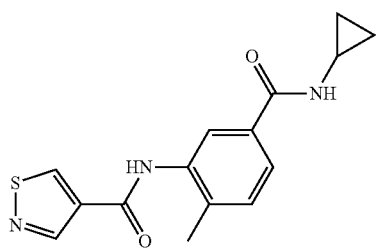

To a solution of isothiazole-3-carboxylic acid (20 mg, 0.15 mmol), EDC (32.4 mg, 0.17 mmol), HOBt (23 mg, 0.17 mmol) in DMF (0.3 mL) was added 3-amino-N-cyclopropyl-4-methyl-benzamide hydrochloride (35 mg, 0.15 mmol) followed by DIPEA (0.03 mL, 0.17 mmol). The reaction was heated at 50° C. for 1 h. Water (0.6 mL) was added dropwise and the reaction removed from heating. The solids were stirred overnight at room temp, filtered, and washed with water to give (42.1 mg, 91% yield). HPLC $t_R$=2.63 min, 99.80% purity; LCMS 302.1 (M+H).

Step A

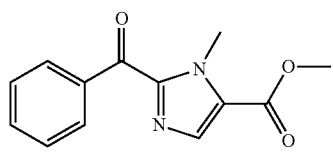

Benzoyl chloride (0.35 mL, 3.0 mmol) was added to a solution of 5-methoxycarbonyl-1methylimidazole (0.35 g, 2.5 mmol) and TEA (0.41 mL) in MeCN (5 mL) at 0° C. The reaction was stirred for 2 h at 0° C., poured into water, and extracted in to EtOAc. The combined organic extracts were dried over $Na_2SO_4$, filtered, and concentrated to a solid which wash washed with MeOH to give a (412 mg).

Step B

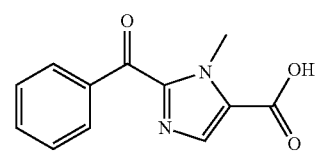

Ester a was hydrolyzed to acid b using the method to make e in Step C of Example 20 (Scheme 1).

Example 33

Scheme 1

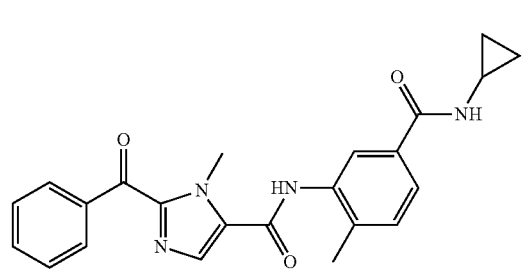

Example 33 was prepared as follows.

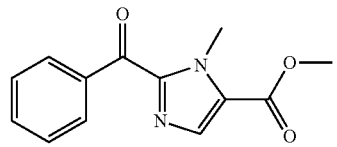

Step A

Benzoyl chloride (0.35 mL, 3.0 mmol) was added to a solution of 5-methoxycarbonyl-1methylimidazole (0.35 g, 2.5 mmol) and TEA (0.41 mL) in MeCN (5 mL) at 0° C. The reaction was stirred for 2 h at 0° C., poured into water, and extracted in to EtOAc. The combined organic extracts were dried over $Na_2SO_4$, filtered, and concentrated to a solid which wash washed with MeOH to give a (412 mg).

Step B

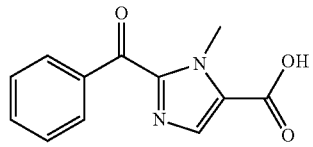

Acid b from Example 33 was coupled to 3-amino-N-cyclopropyl-4-methyl-benzamide hydrochloride using the general procedure to make Example 21 (Scheme 5). HPLC $t_R$=3.43 min, 97% purity; LCMS 403.2 (M+H).

Example 34

Example 34 was prepared in a similar fashion as Example 33. HPLC $t_R$=3.39 min, 98.6% purity; LCMS 391.2 (M+H).

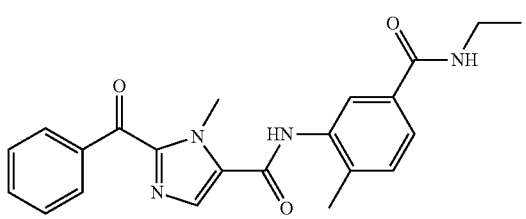

Example 35

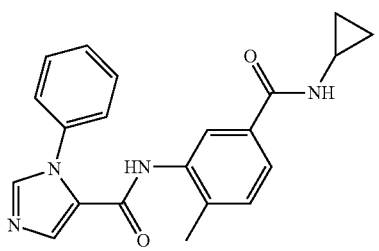

Example 35 was prepared as follows. 5-Ethoxycarbonyl-1-phenylimidazole (200 mg) in MeOH (5 mL) was hydrolyzed according to the general procedure to make e in Step C of Example 20 (Scheme 4) and coupled to 3-amino-N-cyclopropyl-4-methyl-benzamide hydrochloride using the general procedure to make Example 21 Step C (Scheme 5). HPLC $t_R$=2.31 min, 98% purity; LCMS 361.1 (M+H).

Example 36

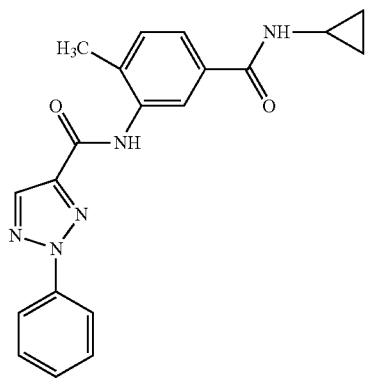

Example 36 was prepared as follows. A solution of 2-phenyl-2H-1,2,3-triazole-4-carboxylic acid (for its preparation, see R. M. Carman and R. F. Evans, *J. Chem. Ed.* 46:847-848 (1969); 100 mg, 0.53 mmol), aniline (300 mg, 1.59 mmol), EDCI (200 mg, 1.06 mol), HOBt (97 mg, 0.63 mol), and diisopropylethyl amine (360 µL, 2.12 mmol) in THF (4 mL), and DMF (0.7 mL) was heated to 54° C. for 95 min. The reaction mixture was concentrated and partitioned between 1 N aq. HCl solution (8 mL) and 1:1 THF: EtOAc (20 mL). The organic extract was separated, washed with 1 N aq. HCl (2×), and satd. aq. NaHCO₃ solution (2×), dried (Na2SO4), filtered, and concentrated to obtain the title compound, Example 36 (172 mg, 90% yield) as a light tan solid, HPLC retention time 3.86 min: LRMS 362.05 (M+H).

Example 37

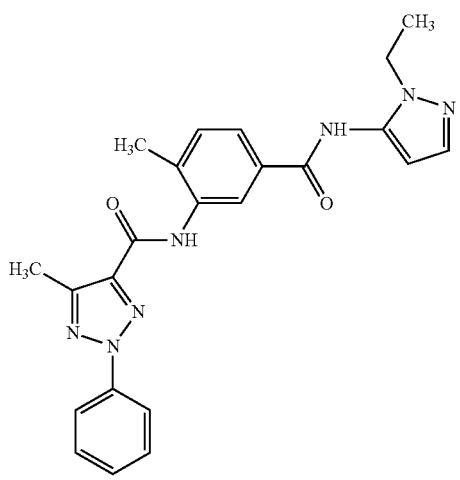

Example 37 was prepared as follows. A solution of 5-methyl-2-phenyl-2H-1,2,3-triazole-4-carbonyl chloride (15 mg, 0.07 mmol), aniline (25 mg, 0.1 mmol), diisopropylethyl amine (35 µL, 0.21 mmol) and predried molecular sieves (3 Å, 100 mg) in dichloromethane (2 mL) was stirred at ambient temperature for 75 min. The reaction mixture was diluted with methanol and filtered. The filtrate was evaporated to dryness and diluted with 1 N aq. HCl. The solid was collected by filtration, washed with 1 N aq. HCl solution, water, satd. aq. NaHCO₃ solution, and water, dried under vacuum over P₂O₅ to obtain a solid which was triturated with ether: hexane mixture (1:1) to obtain the title compound, Example 37 (12 mg, 41% yield), as a white solid, HPLC retention time 4.19 min. LRMS 430.16 (M+H).

Example 38/39

Consolidated (Scheme 8)

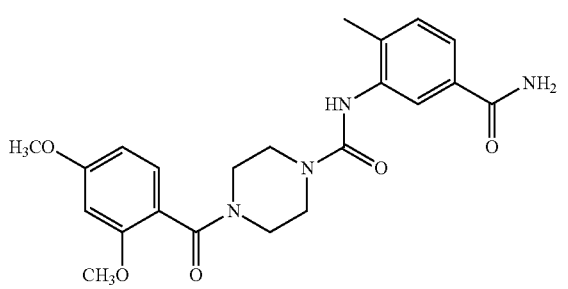

Example 38/39 was prepared as follows.
Step A

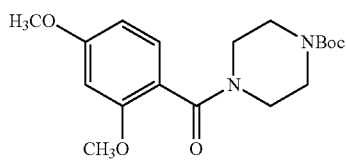

To a solution of 1-BOC-piperazine (2.0 g, 10.7 mmol) and triethylamine (1.6 mL, 11.7 mmol) in dichloromethane (30 mL) was slowly added 2,4-dimethoxybenzoyl chloride a (1.96 g, 9.76 mmol) over 5 minutes and the resulting solution was stirred at rt for 45 minutes. Dichloromethane (~50 mL) was added and the solution was successively washed with 1 N aq. HCl (40 mL), water (40 mL), 1 N aq. NaOH (40 mL), and brine (40 mL). The organic layer was dried over anhyd. sodium sulfate, filtered, and concentrated in vacuo to afford 3.06 g (89%) of compound c as a viscous oil. This crude material was used without any further purification. HPLC Ret. time: 2.97 min.
Step B

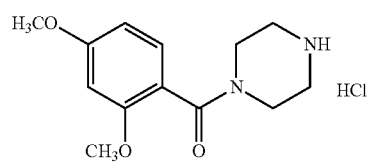

To a solution of compound d (3.06 g, 8.73 mmol) in dioxane (40 mL) at rt was added a 4N solution of anhyd. HCl in dioxane (20 mL). After stirring at rt for 1.5 h, the cloudy reaction mixture was diluted with hexanes (~150 mL) and the solids were collected by vacuum filtration and dried in vacuo to afford 1.9 g (76%) of compound d as a white solid. HPLC Ret. time: 0.77 min. ¹H NMR: (d₄-MeOH, 400 mHz) δ 7.25 (dd, J=6.8, 2.0 Hz, 1H), 6.65-6.63 (m, 2H), 4.10-3.90 (m, 2H), 3.89 (s, 3H), 3.86 (s, 3H), 3.67-3.60 (m, 2H), 3.58 (m, 2H), 3.33-3.22 (m, 4H).

Step C

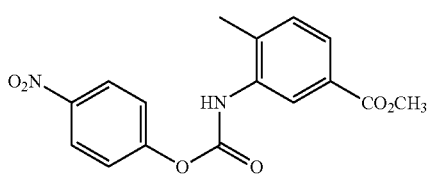

e

To a solution of methyl-3-amino-4-methylbenzoate (1.0 g, 6.0 mmol) and pyridine (2 mL) in dichloromethane (5 mL) at rt was added 4-nitrophenyl chloroformate (1.5 g, 7.3 mmol) and the resulting mixture was stirred at rt for 30 minutes. Dichloromethane (~100 mL) was added and the mixture was successively washed with 10% aq. citric acid (3×50 mL), 10% aq. sodium carbonate (3×50 mL), and brine (50 mL), then dried over anhyd sodium sulfate, filtered, and concentrated in vacuo to afford 1.6 g (80%) of compound e as a pale yellow solid. This material was directly used without any further purification. HPLC Ret. time: 3.05 min.

Step D

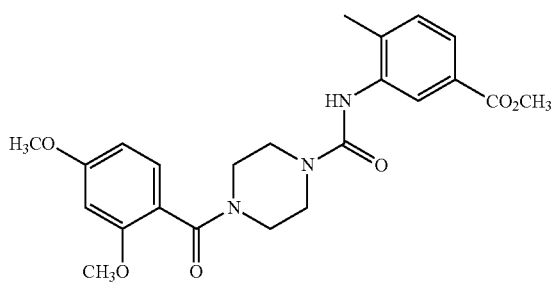

f

To a slurry of compound f (0.62 g, 2.2 mmol) in acetonitrile (4 mL) was added pyridine (1 mL) and the resulting mixture was stirred until a clear solution resulted. At this time, compound e (0.6 g, 1.82 mmol) was added and the reaction mixture was stirred at rt for 15 min, then at 60° C. for 2 h. After cooling to rt, the mixture was concentrated in vacuo and the residue was dissolved in dichloromethane (50 mL) and the solution was successively washed with 1 N aq HCl (3×20 mL), 1 N aq sodium hydroxide (3×20 mL), water (20 mL), and brine (20 mL). The resulting solution was concentrated in vacuo and the resulting oil was purified by flash chromatography on silica gel using a gradient elution beginning with 100% ethyl acetate and ending with 8% methanol in ethyl acetate to afford 0.50 g (62%) of compound f (Compound 39 also called Example 39) as a white solid. HPLC Ret. time: 3.05 min. LCMS MH+ (m/z) 442.4.

Step E

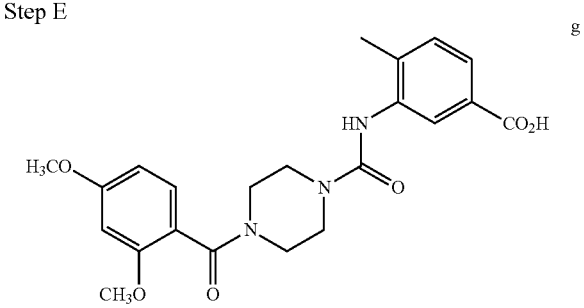

g

To a solution of compound f (0.48 g, 1.1 mmol) in methanol (15 mL) at rt was added 3 N aq sodium hydroxide solution (5 mL) and the resulting mixture was heated at 50° C. for 30 minutes. After cooling to rt, the mixture was concentrated in vacuo and the resulting oil was dissolved in water (~25 mL) and 1 N aq HCl was added until the pH of the solution reached 1-2. The resulting solid was collected by vacuum filtration and dried in vacuo to afford 0.50 g of compound g as a white solid. HPLC Ret. time: 2.50 min. $^1$H NMR: (d$_4$-MeOH, 400 mHz) δ 7.66 (dd, J=8.0, 1.5 Hz, 1H), 7.22 (d, J=7.8 Hz, 1H), 7.10 (d, J=7.8 Hz, 1H), 6.52 (m, 2H), 3.76 (s, 3H), 3.74 (s, 3H), 3.74-3.70 (m, 2H), 3.55 (m, 2H), 3.42 (m, 2H), 3.29-3.24 (m, 4H), 2.20 (s, 3H).

Step F

A mixture of compound g (0.050 g, 0.12 mmol), EDCI (0.029 g, 0.15 mmol), HOBt (0.019 g, 0.14 mmol), and diisopropylethylamine (0.05 mL, 0.26 mmol) in NMP (0.3 mL) was stirred at rt for 20 minutes. At this time, a 0.5 M solution of ammonia in dioxane (0.7 mL, 0.35 mmol) was added and the resulting mixture was stirred at rt for 15 h. The reaction mixture was directly subjected to purification by reverse-phase preparative HPLC. The fractions containing product were neutralized with saturated aq sodium bicarbonate and concentrated on a rotary evaporator to remove the methanol to afford an aqueous slurry. The solids were collected by vacuum filtration, washed with water, and dried in vacuo to afford 0.030 g of Compound 38/39 (also called Example 38/39) as a white solid. HPLC Ret. time: 2.23 min. LCMS MH+ (m/z) 427.3.

Examples 40 to 48

Examples 40 to 48 listed in Table 4 below were prepared as previously described for Example 38.

TABLE 4

| Example No. | Compound Structure | HPLC and LCMS Data |
|---|---|---|
| 40 | 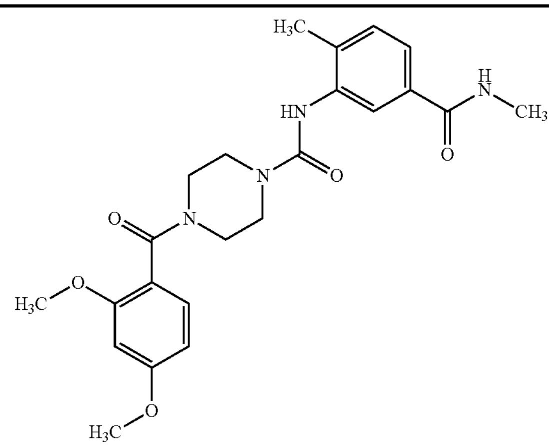 | HPLC $t_R$ = 2.32 min<br>LCMS [M + H]+ = 441.4 |

TABLE 4-continued
| Example No. | Compound Structure | HPLC and LCMS Data |
| --- | --- | --- |
| 41 | 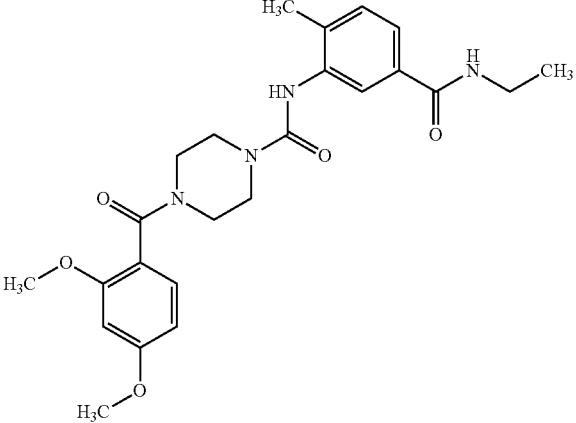 [SMILES: CCNC(=O)c1ccc(C)c(NC(=O)N2CCN(C(=O)c3ccc(OC)cc3OC)CC2)c1] | HPLC $t_R$ = 2.42 min<br>LCMS [M + H]$^+$ = 455.5 |
| 42 | 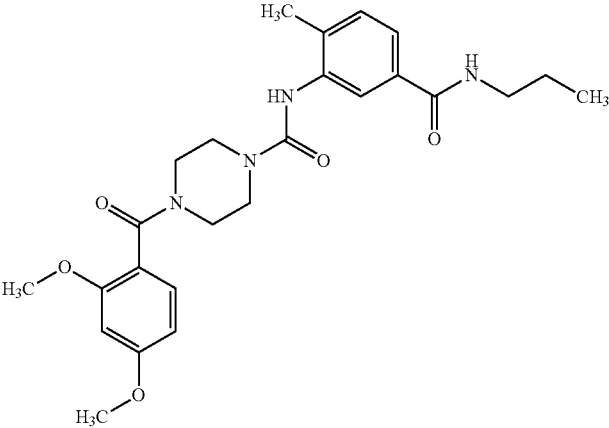 [SMILES: CCCNC(=O)c1ccc(C)c(NC(=O)N2CCN(C(=O)c3ccc(OC)cc3OC)CC2)c1] | HPLC $t_R$ = 2.60 min<br>LCMS [M + H]$^+$ = 469.2 |
| 43 | 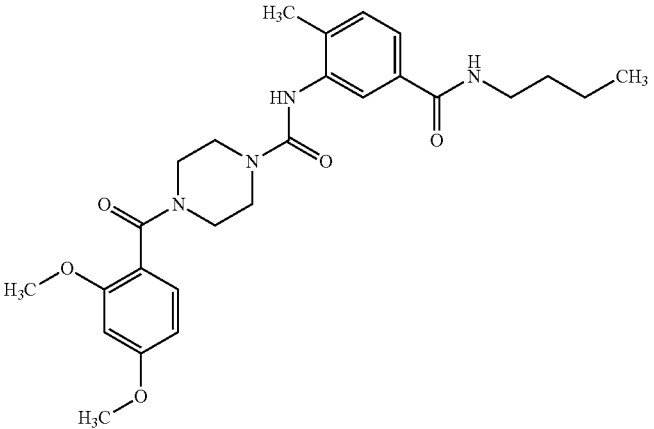 [SMILES: CCCCNC(=O)c1ccc(C)c(NC(=O)N2CCN(C(=O)c3ccc(OC)cc3OC)CC2)c1] | HPLC $t_R$ = 2.79 min<br>LCMS [M + H]$^+$ = 483.0 |

TABLE 4-continued
| Example No. | Compound Structure | HPLC and LCMS Data |
| --- | --- | --- |
| 44 | 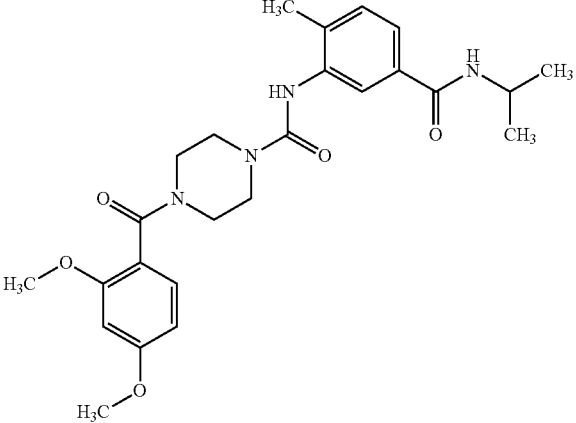 [SMILES: COc1ccc(C(=O)N2CCN(C(=O)Nc3cc(C(=O)NC(C)C)ccc3C)CC2)c(OC)c1] | HPLC $t_R$ = 2.56 min<br>LCMS [M + H]$^+$ = 469.2 |
| 45 | 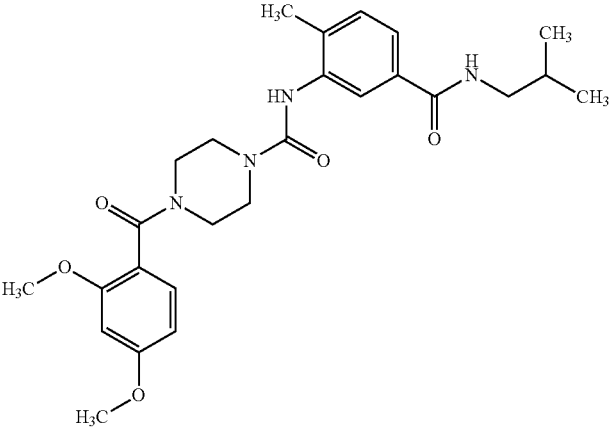 [SMILES: COc1ccc(C(=O)N2CCN(C(=O)Nc3cc(C(=O)NCC(C)C)ccc3C)CC2)c(OC)c1] | HPLC $t_R$ = 2.76 min<br>LCMS [M + H]$^+$ = 483.2 |
| 46 | 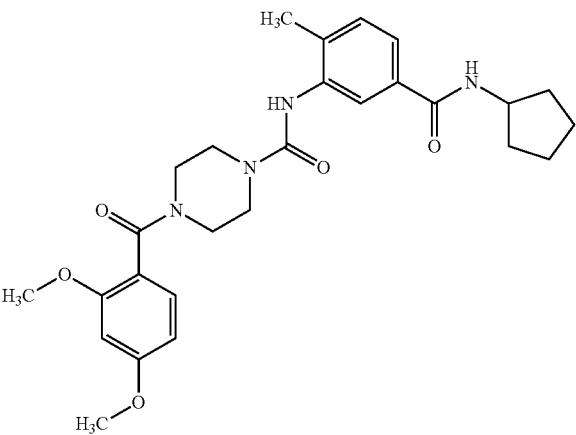 [SMILES: COc1ccc(C(=O)N2CCN(C(=O)Nc3cc(C(=O)NC4CCCC4)ccc3C)CC2)c(OC)c1] | HPLC $t_R$ = 2.82 min<br>LCMS [M + H]$^+$ = 495.2 |

TABLE 4-continued

| Example No. | Compound Structure | HPLC and LCMS Data |
|---|---|---|
| 47 | 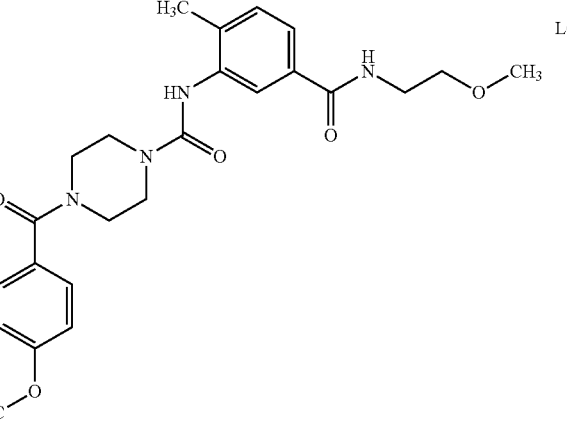 | HPLC $t_R$ = 2.36 min<br>LCMS [M + H]$^+$ = 485.2 |
| 48 | 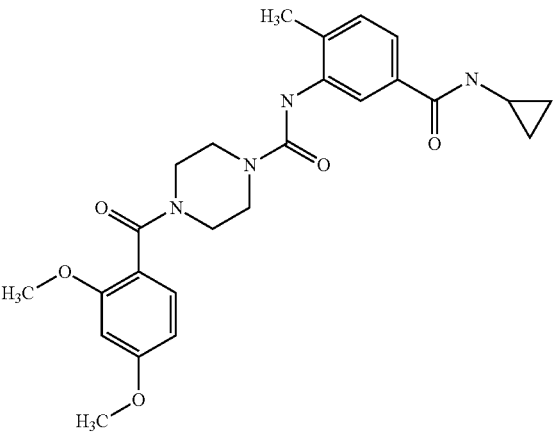 [SMILES: COc1ccc(C(=O)N2CCN(C(=O)Nc3cc(C(=O)NC4CC4)ccc3C)CC2)c(OC)c1] | HPLC $t_R$ = 2.44 min<br>LCMS [M + H]$^+$ = 467.2 |

Example 49

Step A (Scheme 8)

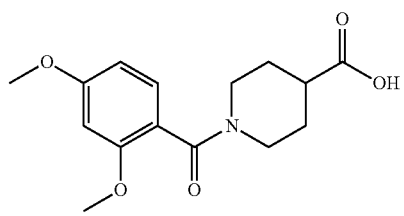

c

Example 49 was prepared as follows with R$^{39}$=2,4-dimethoxy). A solution of 2,4-methoxybenzoic acid (1.00 g, 5.49 mmol), 1-[3-(dimethylamino)-propyl]-3-ethylcarbodiimide hydrochloride and 1-hydroxybenzotriazole in anhydrous DMF (20 mL) was stirred at rt for 1.5 h. The mixture was quenched with ice-water (150 mL) and extracted with ethyl acetate (200 mL×2). The combined organic layer was washed with water, saturated sodium bicarbonate (50 mL×2), brine (50 mL), then dried over sodium sulfate and concentrated in vacuo. The crude compound (2.06 g) was redissolved in anhydrous DMF (20 mL) at rt, diisopropylethylamine (1.91 mL, 0.98 mmol) was added followed by isonipecotic acid (0.85 g, 6.59 mmol) in one portion followed by stirring at rt for 16 h. The resulting mixture was quenched with ice-water and extracted with ethyl acetate (200 mL×3) and the combined organic layers were washed with water (20 mL×2) and brine, then dried over sodium sulfate and concentrated in vacuo to give 1.51 g of compound c as a clear oil. This material was used directly without any further purification. HPLC Ret. Time: 2.14 min. MH$^+$ (m/z) 294.

Step B

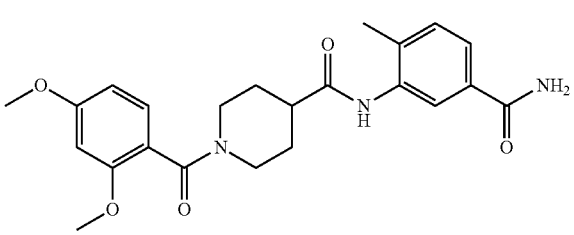

49

Compound c (0.10 g, 0.20 mmol), 1-[3-(dimethylamino) propyl]-3-ethylcarbodiimide hydrochloride and 1-hydroxybenzotriazole in anhydrous DMF (0.8 mL) were stirred under at room temperature for 1 h. Diisopropylethylamine (0.108 mL, 0.60 mmol) was added followed by methyl-3-amino-4-methylbenzoate (62 mg, 0.40 mmol). The reaction was stirred at rt for 16 h. The crude product was purified by reverse-phase preparative HPLC and the fractions containing the product were concentrated and partitioned between ethyl acetate and saturated aqueous sodium bicarbonate. The organic layer was dried over sodium sulfate and concentrated in vacuo to give 0.026 g of Example 49 (also called Compound 49) as a white solid. HPLC Ret. Time: 2.30 min. LCMS MH+ (m/z) 426.

Example 50

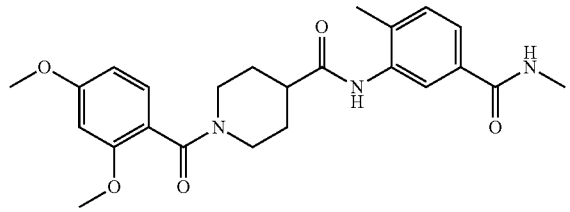

50

Example 50 was prepared as previously described for Example 49. HPLC Ret. Time: 2.39 min. LCMS MH+ (m/z) 440.4.

Example 51

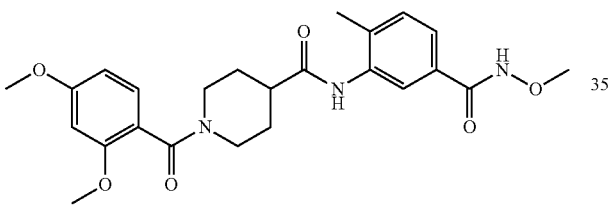

51

Example 51 was prepared as previously described for Example 49. HPLC Ret. Time: 2.39 min. LCMS MH+ (m/z) 456.2.

Example 52

Step A

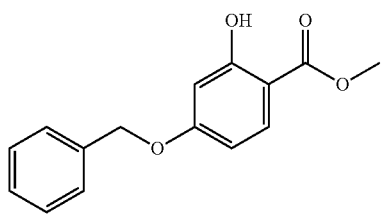

a

Example 52 was prepared as follows. To a suspension of methyl-2,4-dihydroxybenzoate (4.00 g, 23.8 mmol) and potassium carbonate in acetone (100 mL) at 0° C. was added benzyl bromide (3.2 mL, 26.4 mmol) dropwise via syringe. The resulting mixture was stirred at 0° C. for 1 h and at rt for 16 h whereupon the mixture filtered and the resulting filtrate was concentrated in vacuo. The remaining residue was purified by column chromatography to give 4.57 g (74%) of compound a as a white solid. HPLC Ret. Time: 3.80 min.

Step B

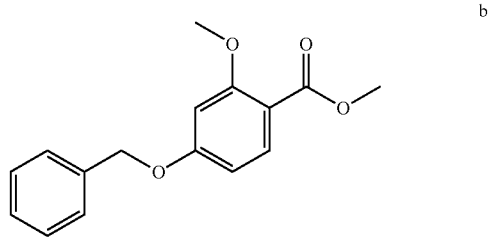 [SMILES: COC(=O)c1ccc(OCc2ccccc2)cc1OC]

b

To a solution of compound b (4.57 g, 17.7 mmol) in anhydrous DMF (70 mL) at 0° C. was added sodium hydride (60% dispersion in oil, 1.06 g, 26.6 mmol) portionwise and the resulting mixture was stirred at 0° C. for 10 min. At this time, iodomethane (2.80 mL, 45 mmol) was added dropwise followed by stirring at 0° C. for 1 h and at rt for 16 h. The mixture was quenched with ice water (300 mL) and the solids were collected by vacuum filtration after 1 h. The solids were washed with water and dried in vacuo to give 4.80 g (99.5%) of compound b as a white solid. This material was used without any further purification. HPLC Ret. Time: 3.38 min. LCMS MH+ (m/z) 273.

Step C

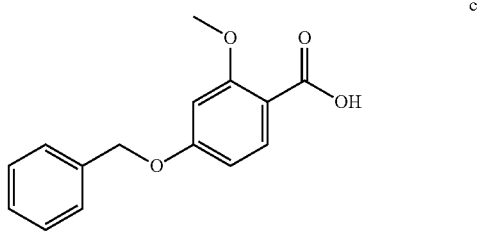 [SMILES: COc1cc(OCc2ccccc2)ccc1C(=O)O]

c

Compound c (3.00 g, 11.0 mmol) in methanol/THF 1:1 (22 mL) and 3N aq sodium hydroxide (11 mL) was heated at 60° C. for 1 h. After the solvent was removed in vacuo, the mixture was brought to pH 1 by slowly adding 3N aq HCl. The resulting solid was collected by filtration and dried in vacuo to give 2.96 g of compound c as a white solid. This material was used without any further purification. HPLC Ret. Time: 3.04 min. MH+ (m/z) 259.

Step D

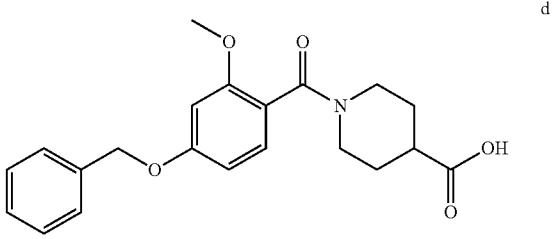 [SMILES: COc1cc(OCc2ccccc2)ccc1C(=O)N1CCC(C(=O)O)CC1]

d

Compound d was prepared from compound c utilizing the same procedure as previously described for compound a in Example 49 by substituting 2,4-methoxylbenzoic acid with instant compound c.

Example 53

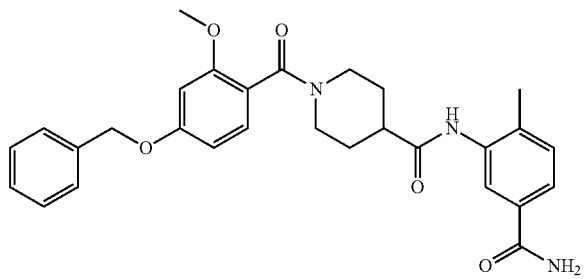

Example 53 was prepared from compound c in Example 49 utilizing the same procedure as previously described in Step B therein. HPLC Ret. Time: 3.07 min. LCMS MH$^+$ (m/z) 502.3.

Example 54

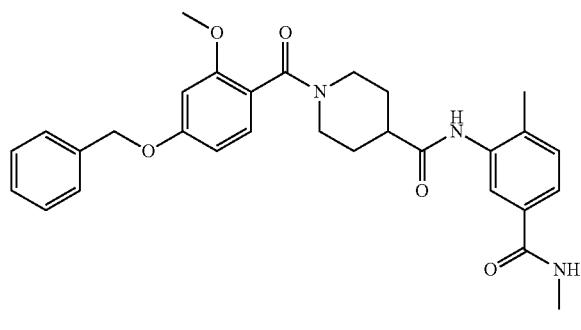

Example 54 was prepared from compound c in Example 49 utilizing the same procedure as previously described in Step B therein. HPLC Ret. Time: 3.07 min. LCMS MH$^+$ (m/z) 516.2.

Example 55

Step A

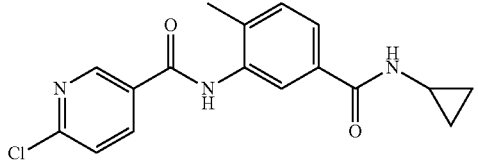

Example 55 was prepared as follows. Compound a was prepared from 6-chloronicotinic acid utilizing the same procedure as previously described in Step B of Example 49.

Step B

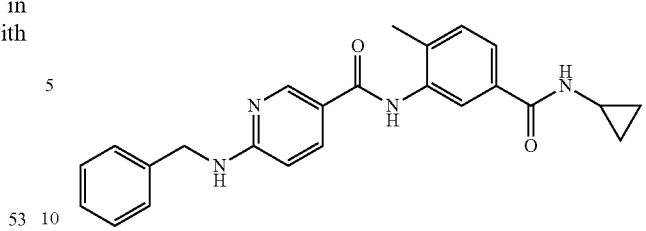

A solution of compound a (50 mg, 0.15 mmol) and benzylamine (0.10 mL, 0.90 mmol) in anhyd NMP (0.5 mL) was heated in a microwave reactor at 200° C. for 15 minutes. The reaction mixture was subjected directly to purification by reverse-phase preparative HPLC and the fraction containing the product was concentrated and lyophilized to give 0.039 g of the TFA salt of the title compound (Example 55) as a white solid. HPLC Ret. Time: 2.11 min. LCMS MH$^+$ (m/z) 401.2.

Example 56

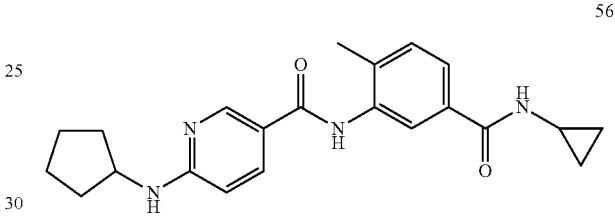

Example 56 was prepared from compound a as previously described in Step B for Example 55. HPLC Ret. Time: 1.85 min. LCMS MH$^+$ (m/z) 379.2.

Example 57

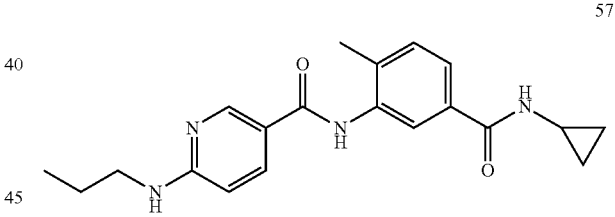

Example 57 was prepared from compound a as previously described in Step B for Example 55. HPLC Ret. Time: 1.66 min. LCMS MH$^+$ (m/z) 353.3.

Example 58

Step A

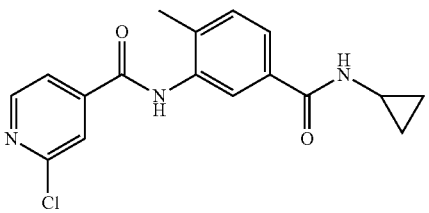

Compound a was prepared from 2-chloroisonicotinic acid utilizing the same procedure as previously described in Step B for Example 49.

Step B

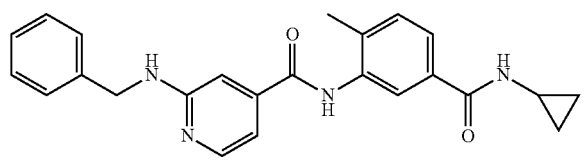

58

Example 58 was prepared from compound a utilizing the same procedure as previously described in Step B for Example 55. HPLC Ret. Time: 2.08 min. LCMS MH+ (m/z) 401.1.

Example 59

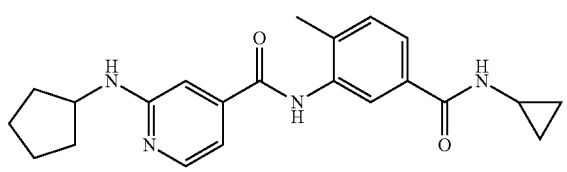

59

Example 59 was prepared from compound a utilizing the same procedure as previously described in Step B for Example 55. HPLC Ret. Time: 1.90 min. LCMS MH+ (m/z) 379.2.

Example 60

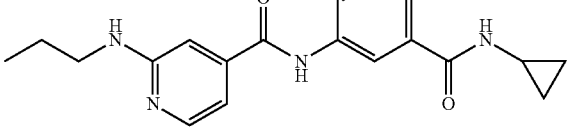

60

Example 60 was prepared from compound a utilizing the same procedure as previously described in Step B for Example 55. HPLC Ret. Time: 1.69 min. LCMS MH+ (m/z) 353.1.

Example 61

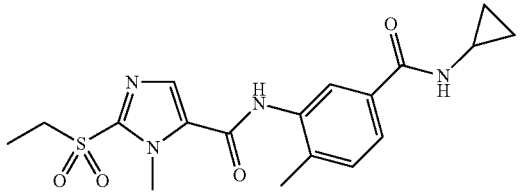

61

Step A

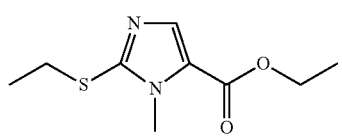

a

Example 61 was prepared as follows. To a slurry of ethyl-2-mercapto-1H-imidazole-5-carboxylate (0.50 g, 2.7 mmol) and potassium carbonate (0.75 g, 5.4 mmol) in anhydrous DMF (10 mL) at room temperature was added iodoethane (0.32 mL, 4.05 mmol) dropwise. The resulting mixture was stirred for 1 h at rt and the reaction was quenched with water (40 mL) and extracted with ethyl acetate (100 mL×3). The combined organic layers were washed with 1M aqueous sodium thiosulphite (20 mL×2), water (20 mL×2), and brine, then dried over sodium sulfate and concentrated in vacuo to give 0.52 g (90%) of compound a as a clear oil. This material was used directly without any further purification. HPLC Ret. Time: 1.83 min.

Step B

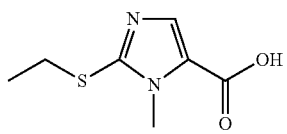

b

A solution of compound a (0.52 g, 2.43 mmol) in methanol (8 mL) and 5 N aq sodium hydroxide (1.5 mL) was refluxed for 1 h. After cooling to rt, the solvent was removed in vacuo and the mixture was brought to pH 1 by slowly adding 6N aq HCl. This solution was lyophilized to give 0.92 g of compound b as a white solid. The resulting material was used directly without any further purification. HPLC Ret. Time: 0.58 min. LCMS MH+ (m/z) 187.

Step C

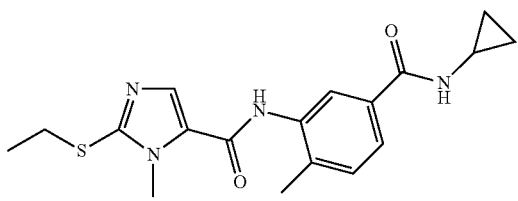

c

Compound c was prepared from compound b utilizing the same procedure as previously described in Step B for Example 49.

Step D

To a slurry of compound c (0.26 g, 0.74 mmole) in dichloromethane (3 mL) was added mCPBA (0.42 g) in one portion and the resulting mixture was stirred at rt for 16 h. The mixture was diluted with water (40 mL) and extracted with ethyl acetate (100 mL×3). The combined organic layers were washed with 1M aq sodium thiosulphite solution (20 mL), water (20 ml×2) and brine, then dried over sodium sulfate and concentrated in vacuo to give 0.30 g of white sticky solid. Purification by reverse-phase preparative HPLC and lyophilization of the fraction containing the product afforded the TFA salt of the title compound (Example 61) as a white solid. HPLC Ret. Time: 2.12 min. MH+ (m/z) 391.

Example 62

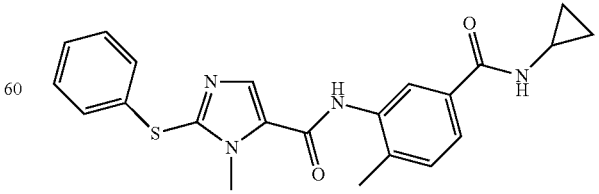

62

To a solution of benzenethiol (0.081 g, 0.72 mmol) in THF (1 mL) was added 60% oil dispersion of sodium hydride (0.020 g, 0.51 mmol) and the resulting mixture was heated to 40° C. for 10 minutes. At this time, Example 61 was added in one portion and the resulting mixture was stirred at 50° C. for 16 h. The reaction was quenched with water (10 mL) and extracted with ethyl acetate (100 mL). The organic layer was washed with 1M aqueous sodium hydroxide and brine, then dried over sodium sulfate and concentrated in vacuo to give the crude product as a white solid. This material was purified by reverse-phase preparative HPLC and lyophilization of the fraction containing the product afforded the TFA salt of the title compound (Example 62) as a white solid. HPLC Ret. Time: 2.79 min. LCMS MH+ (m/z) 407.

Example 63

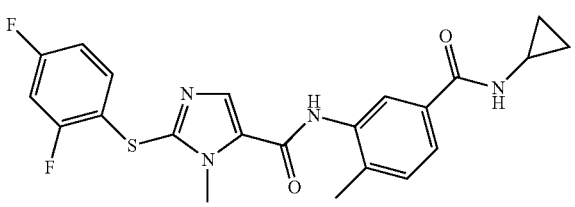

63

Example 63 was prepared from Example 61 utilizing the same procedure as previously described for Example 62. HPLC Ret. Time: 3.08 min. LCMS MH+ (m/z) 443.1.

Example 64

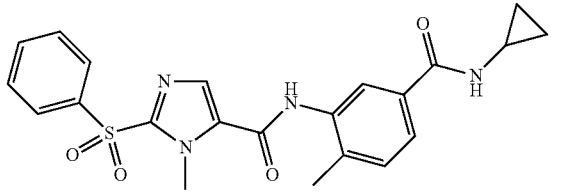

64

Example 64 was prepared from Example 62 utilizing the same procedure as previously described in Step D for Example 61. HPLC Ret. Time: 2.57 min. LCMS MH+ (m/z) 439.2.

Examples 65 to 126

Examples 65 to 126 as listed in Table 5 were prepared as described above for the previous Examples.

TABLE 5

| Example No. | Structure |
|---|---|
| 65 | 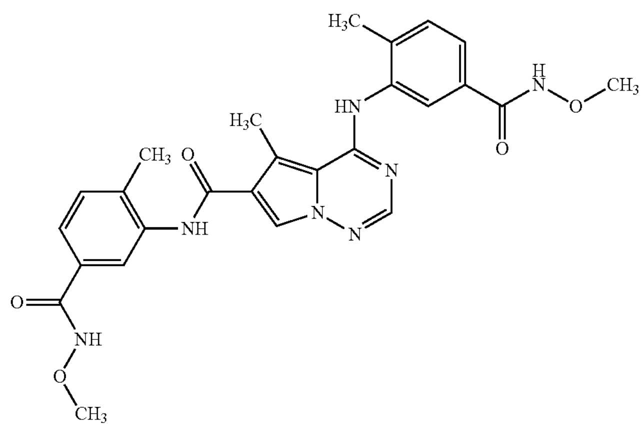 [SMILES: CONC(=O)c1ccc(C)c(NC(=O)c2cn3ncnc(Nc4cc(C(=O)NOC)ccc4C)c3c2C)c1] |
| 66 | 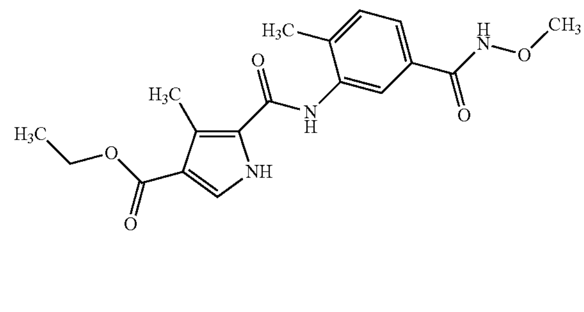 [SMILES: CCOC(=O)c1c[nH]c(C(=O)Nc2cc(C(=O)NOC)ccc2C)c1C] |

TABLE 5-continued

| Example No. | Structure |
|---|---|
| 67 | 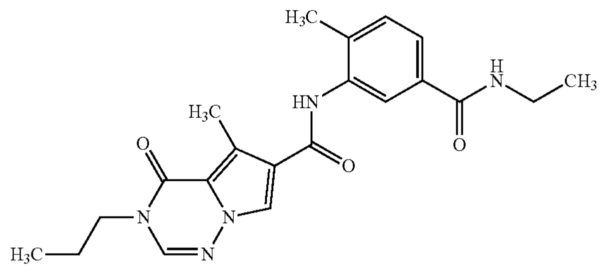 [SMILES: CCCn1cnn2cc(C(=O)Nc3cc(C(=O)NCC)ccc3C)c(C)c2c1=O] |
| 68 | 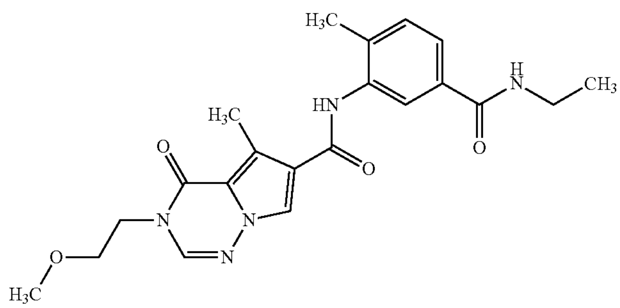 [SMILES: CCNC(=O)c1ccc(C)c(NC(=O)c2cn3ncn(CCOC)c(=O)c3c2C)c1] |
| 69 | 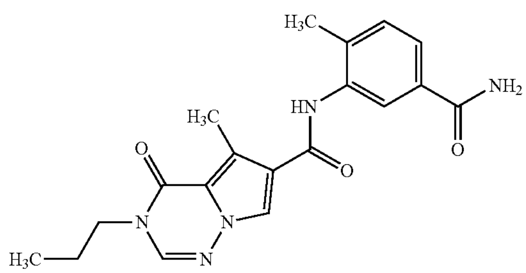 [SMILES: CCCn1cnn2cc(C(=O)Nc3cc(C(N)=O)ccc3C)c(C)c2c1=O] |
| 70 | 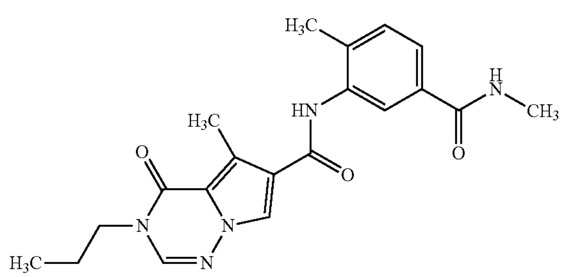 [SMILES: CCCn1cnn2cc(C(=O)Nc3cc(C(=O)NC)ccc3C)c(C)c2c1=O] |
| 71 | 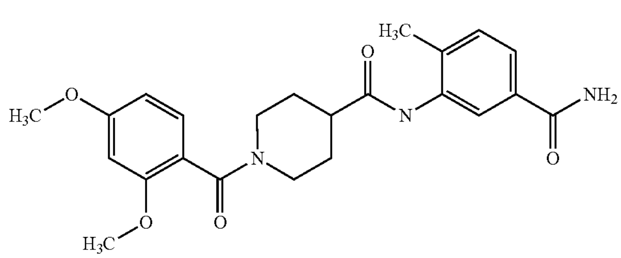 [SMILES: COc1ccc(C(=O)N2CCC(C(=O)Nc3cc(C(N)=O)ccc3C)CC2)c(OC)c1] |

TABLE 5-continued
| Example No. | Structure |
|---|---|
| 72 | 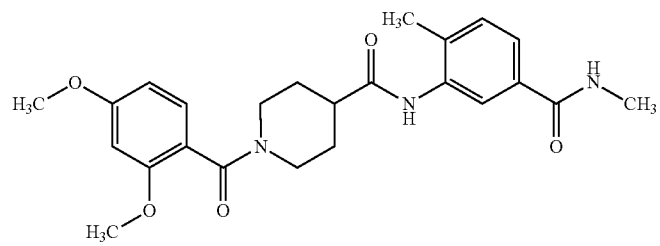 |
| 73 | 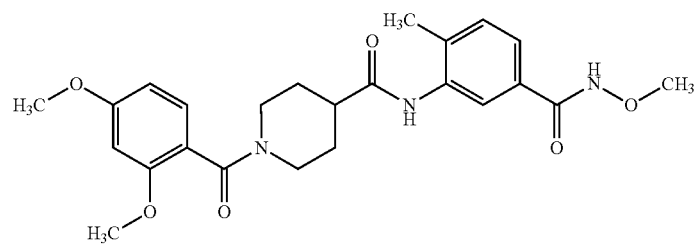 |
| 74 | 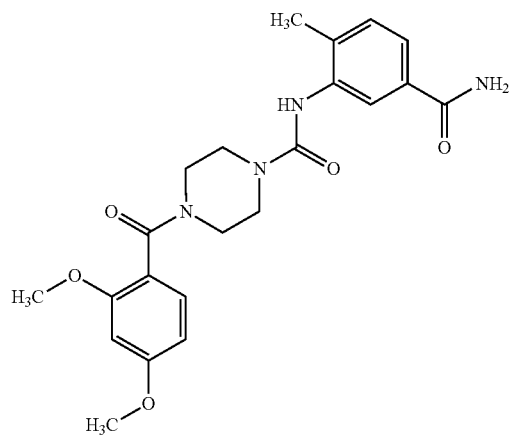 [SMILES: COc1ccc(C(=O)N2CCN(C(=O)Nc3cc(C(N)=O)ccc3C)CC2)c(OC)c1] |
| 75 | 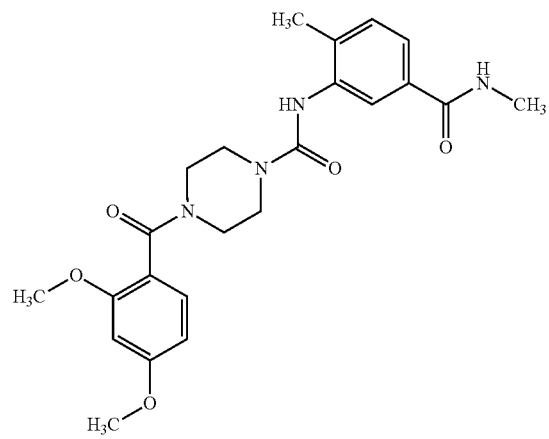 |

TABLE 5-continued

| Example No. | Structure |
|---|---|
| 76 | 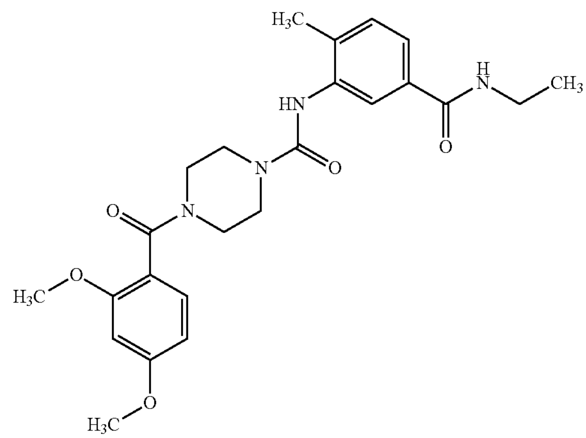 [SMILES: CCNC(=O)c1ccc(C)c(NC(=O)N2CCN(C(=O)c3ccc(OC)cc3OC)CC2)c1] |
| 77 | 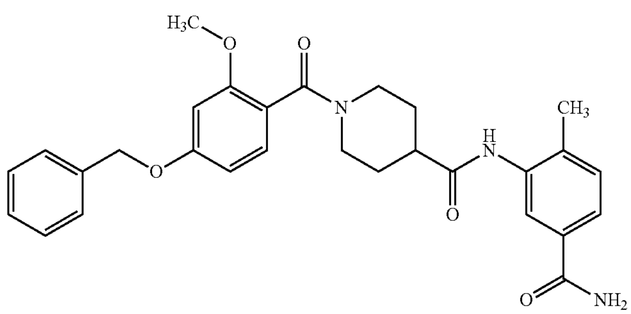 [SMILES: COc1cc(OCc2ccccc2)ccc1C(=O)N1CCC(C(=O)Nc2cc(C(N)=O)ccc2C)CC1] |
| 78 | 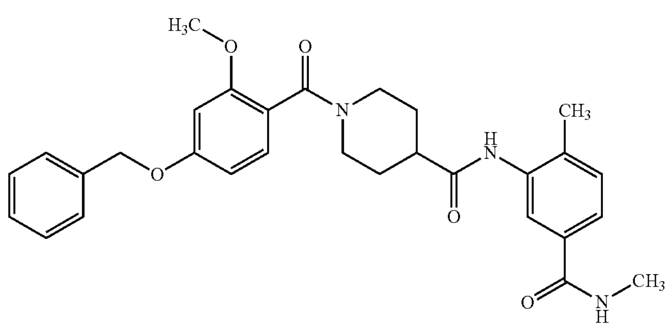 [SMILES: CNC(=O)c1ccc(C)c(NC(=O)C2CCN(C(=O)c3ccc(OCc4ccccc4)cc3OC)CC2)c1] |
| 79 | 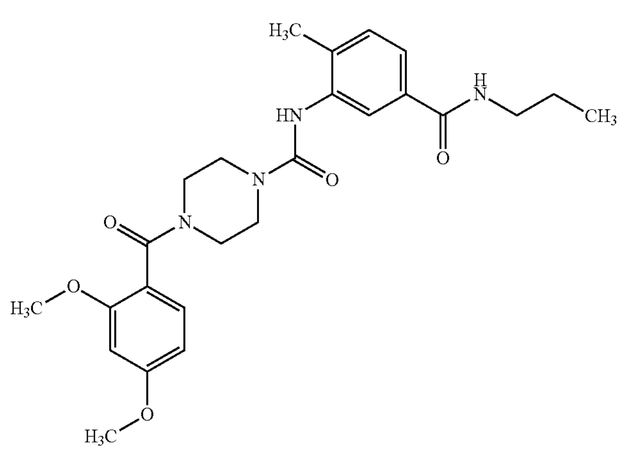 [SMILES: CCCNC(=O)c1ccc(C)c(NC(=O)N2CCN(C(=O)c3ccc(OC)cc3OC)CC2)c1] |

TABLE 5-continued

| Example No. | Structure |
|---|---|
| 80 | *(chemical structure)* |
| 81 | *(chemical structure)* |
| 82 | *(chemical structure)* |

TABLE 5-continued

| Example No. | Structure |
|---|---|
| 83 | (chemical structure) |
| 84 | (chemical structure) |
| 85 | (chemical structure) |
| 86 | (chemical structure) |

TABLE 5-continued
| Example No. | Structure |
|---|---|
| 87 | 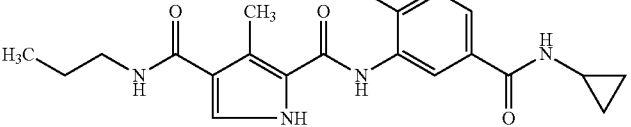 |
| 88 | 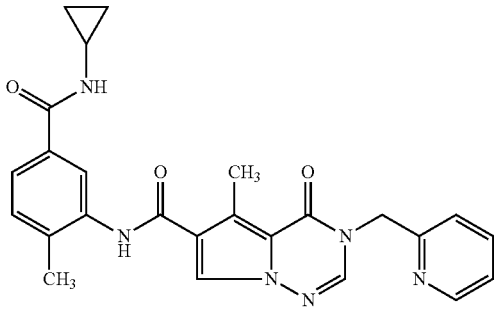 [SMILES: Cc1ccc(C(=O)NC2CC2)cc1NC(=O)c1cn2ncn(Cc3ccccn3)c(=O)c2c1C] |
| 89 | 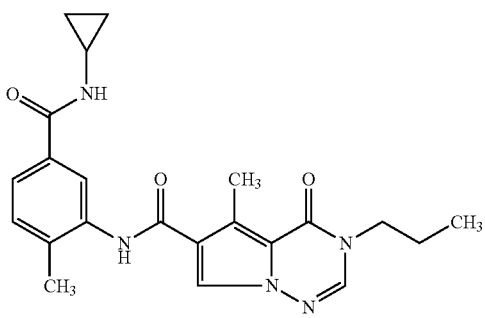 [SMILES: CCCn1cnn2cc(C(=O)Nc3cc(C(=O)NC4CC4)ccc3C)c(C)c2c1=O] |
| 90 | 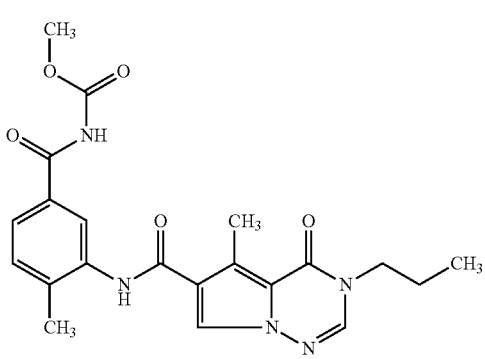 [SMILES: CCCn1cnn2cc(C(=O)Nc3cc(C(=O)NC(=O)OC)ccc3C)c(C)c2c1=O] |
| 91 | 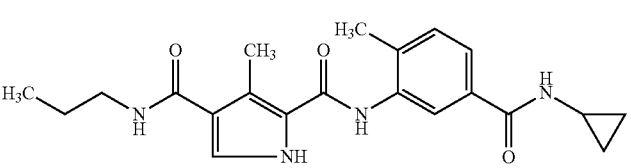 [SMILES: CCCNC(=O)c1c[nH]c(C(=O)Nc2cc(C(=O)NC3CC3)ccc2C)c1C] |
| 92 | 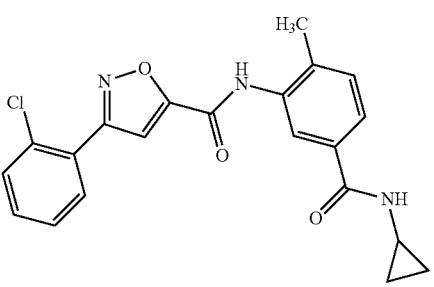 [SMILES: Cc1ccc(C(=O)NC2CC2)cc1NC(=O)c1cc(-c2ccccc2Cl)no1] |

TABLE 5-continued

| Example No. | Structure |
| --- | --- |
| 93 | 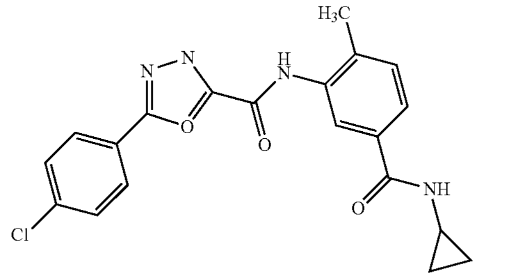 |
| 94 | 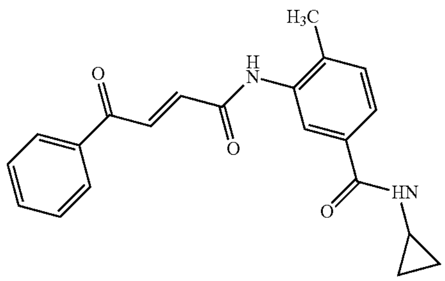 [SMILES: Cc1ccc(C(=O)NC2CC2)cc1NC(=O)/C=C/C(=O)c1ccccc1] |
| 95 | 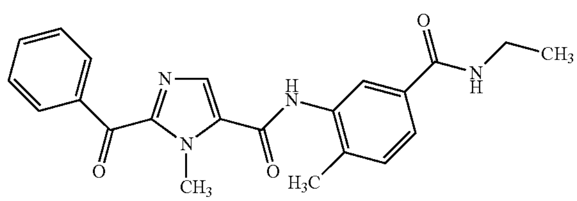 [SMILES: CCNC(=O)c1ccc(C)c(NC(=O)c2cnc(C(=O)c3ccccc3)n2C)c1] |
| 96 | 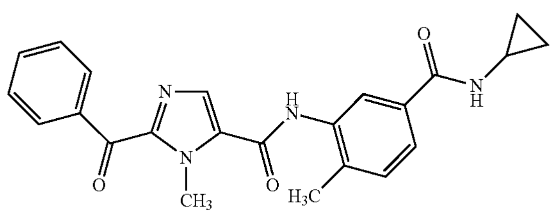 [SMILES: Cc1ccc(C(=O)NC2CC2)cc1NC(=O)c1cnc(C(=O)c2ccccc2)n1C] |
| 97 | 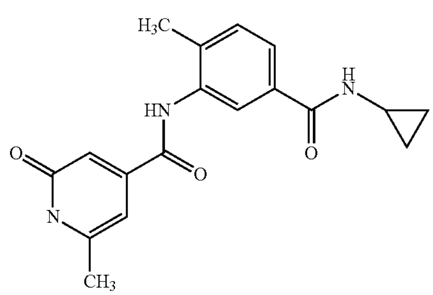 [SMILES: Cc1cc(C(=O)Nc2cc(C(=O)NC3CC3)ccc2C)cc(=O)[nH]1] |
| 98 | 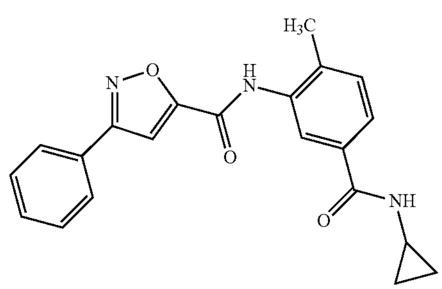 [SMILES: Cc1ccc(C(=O)NC2CC2)cc1NC(=O)c1cc(-c2ccccc2)no1] |

TABLE 5-continued
| Example No. | Structure |
|---|---|
| 99 | 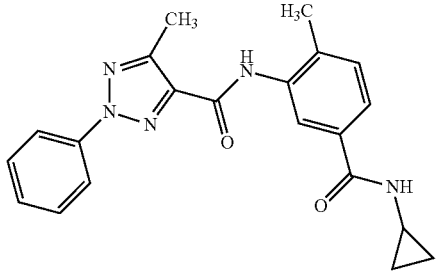 [SMILES: Cc1ccc(C(=O)NC2CC2)cc1NC(=O)c1nn(-c2ccccc2)nc1C] |
| 100 | 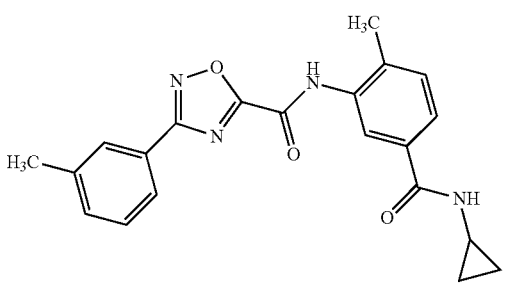 [SMILES: Cc1cccc(-c2noc(C(=O)Nc3cc(C(=O)NC4CC4)ccc3C)n2)c1] |
| 101 | 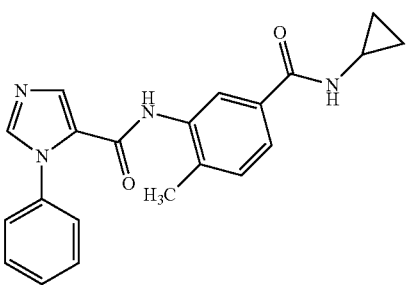 [SMILES: Cc1ccc(C(=O)NC2CC2)cc1NC(=O)c1cncn1-c1ccccc1] |
| 102 | 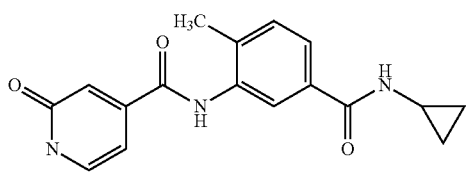 [SMILES: Cc1ccc(C(=O)NC2CC2)cc1NC(=O)c1cc[nH]c(=O)c1] |
| 103 | 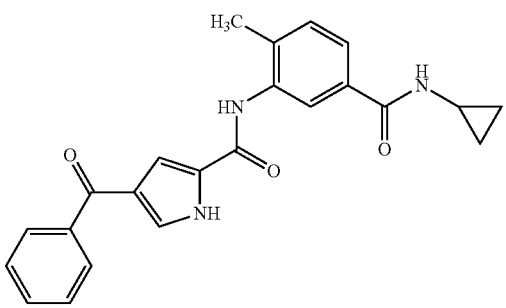 [SMILES: Cc1ccc(C(=O)NC2CC2)cc1NC(=O)c1cc(C(=O)c2ccccc2)c[nH]1] |
| 104 | 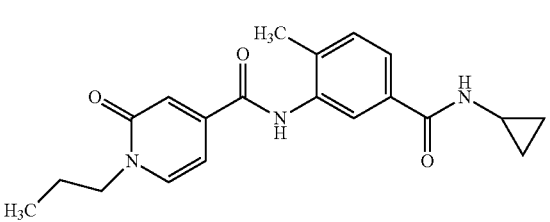 [SMILES: CCCn1ccc(C(=O)Nc2cc(C(=O)NC3CC3)ccc2C)cc1=O] |

TABLE 5-continued

| Example No. | Structure |
| --- | --- |
| 105 | 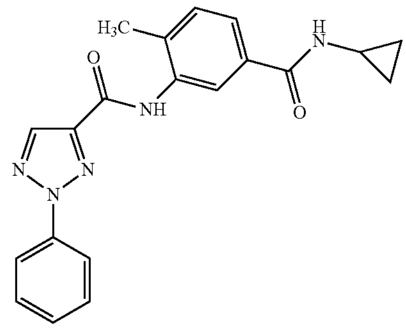 [SMILES: Cc1ccc(C(=O)NC2CC2)cc1NC(=O)c1cnn(-c2ccccc2)n1] |
| 106 | 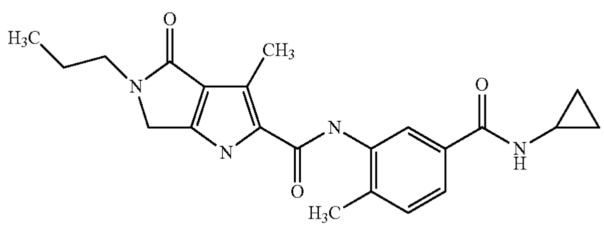 [SMILES: CCCN1Cc2[nH]c(C(=O)Nc3cc(C(=O)NC4CC4)ccc3C)c(C)c2C1=O] |
| 107 | 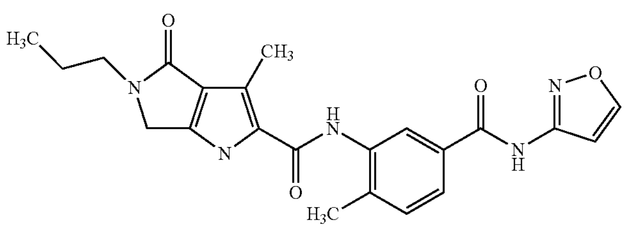 [SMILES: CCCN1Cc2[nH]c(C(=O)Nc3cc(C(=O)Nc4ccon4)ccc3C)c(C)c2C1=O] |
| 108 | 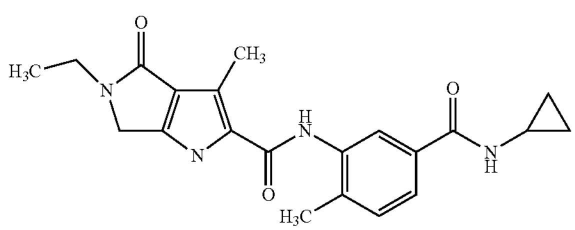 [SMILES: CCN1Cc2[nH]c(C(=O)Nc3cc(C(=O)NC4CC4)ccc3C)c(C)c2C1=O] |
| 109 | 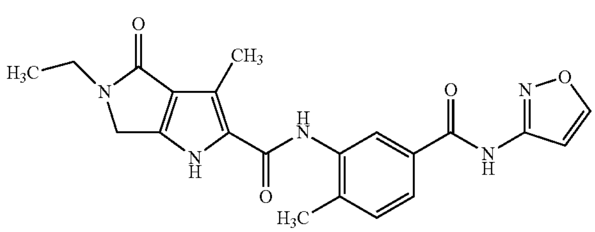 [SMILES: CCN1Cc2[nH]c(C(=O)Nc3cc(C(=O)Nc4ccon4)ccc3C)c(C)c2C1=O] |
| 110 | 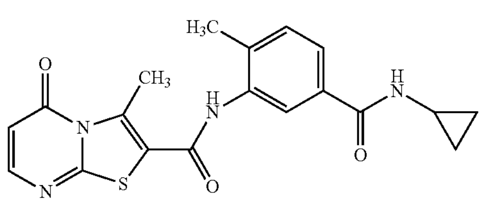 [SMILES: Cc1ccc(C(=O)NC2CC2)cc1NC(=O)c1sc2nccc(=O)n2c1C] |

TABLE 5-continued
| Example No. | Structure |
|---|---|
| 111 | 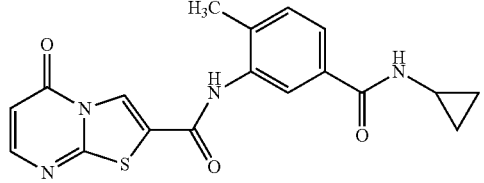 [SMILES: Cc1ccc(C(=O)NC2CC2)cc1NC(=O)c1cn2c(=O)ccnc2s1] |
| 112 | 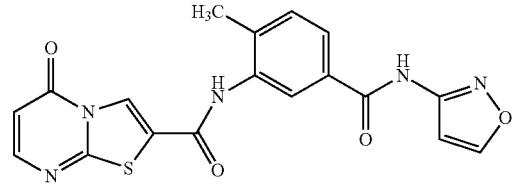 [SMILES: Cc1ccc(C(=O)Nc2ccon2)cc1NC(=O)c1cn2c(=O)ccnc2s1] |
| 113 | 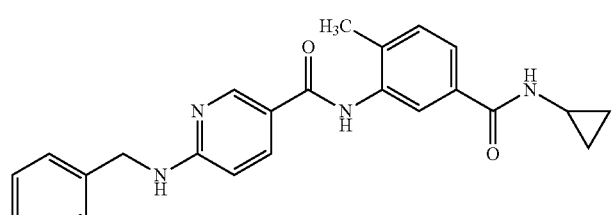 |
| 114 | 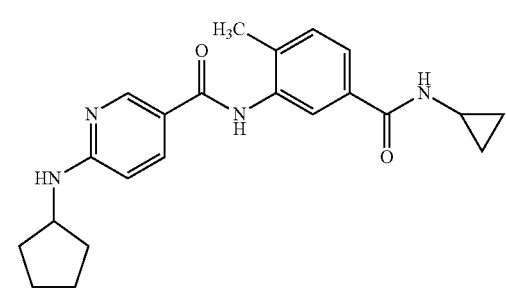 [SMILES: Cc1ccc(C(=O)NC2CC2)cc1NC(=O)c1ccc(NC2CCCC2)nc1] |
| 115 | 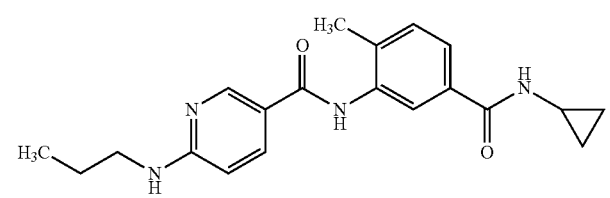 [SMILES: CCCNc1ccc(C(=O)Nc2cc(C(=O)NC3CC3)ccc2C)cn1] |
| 116 | 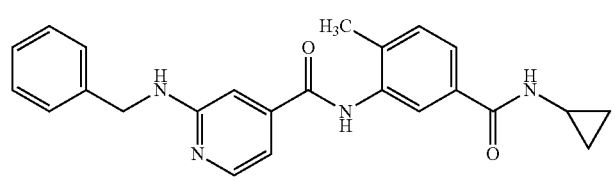 [SMILES: Cc1ccc(C(=O)NC2CC2)cc1NC(=O)c1ccnc(NCc2ccccc2)c1] |

TABLE 5-continued

| Example No. | Structure |
|---|---|
| 117 | 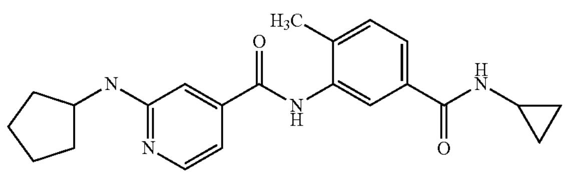 [SMILES: Cc1ccc(C(=O)NC2CC2)cc1NC(=O)c1ccnc(NC2CCCC2)c1] |
| 118 | 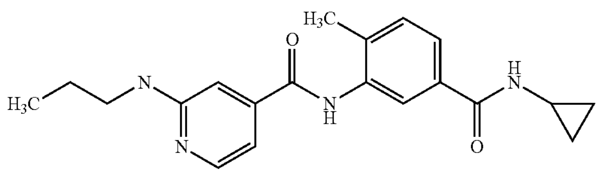 [SMILES: CCCNc1cc(C(=O)Nc2cc(C(=O)NC3CC3)ccc2C)ccn1] |
| 119 | 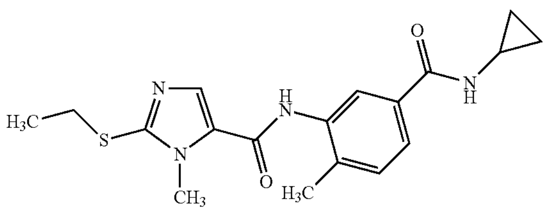 [SMILES: CCSc1ncc(C(=O)Nc2cc(C(=O)NC3CC3)ccc2C)n1C] |
| 120 | 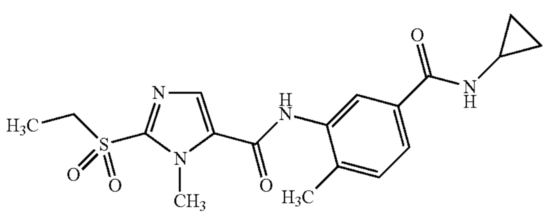 [SMILES: CCS(=O)(=O)c1ncc(C(=O)Nc2cc(C(=O)NC3CC3)ccc2C)n1C] |
| 121 | 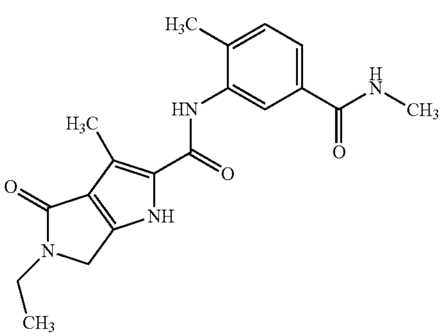 [SMILES: CCN1Cc2[nH]c(C(=O)Nc3cc(C(=O)NC)ccc3C)c(C)c2C1=O] |

TABLE 5-continued
| Example No. | Structure |
|---|---|
| 122 | 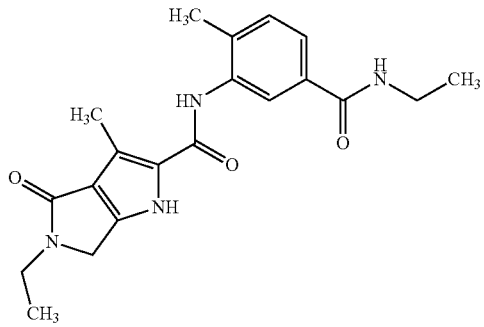 [SMILES: CCNC(=O)c1ccc(C)c(NC(=O)c2[nH]c3c(c2C)C(=O)N(CC)C3)c1] |
| 123 | 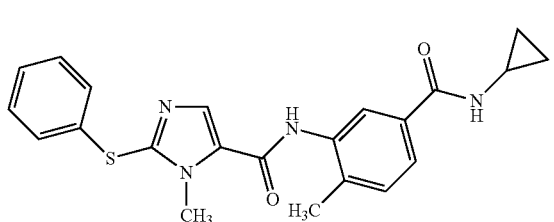 |
| 124 | 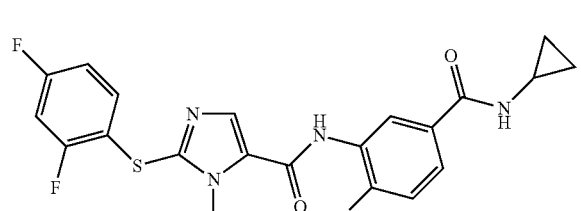 |
| 125 | 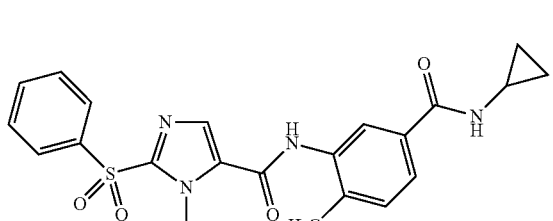 |
| 126 | 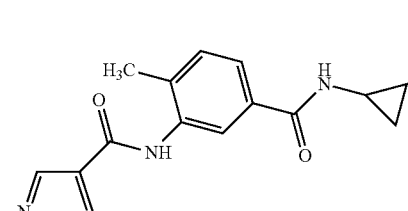 |

Examples 127 to 225

The following Examples 127 to 225 are alpha selective and may be made by the methods described. The previous definitions still pertain. Additional Schemes are also shown.

Scheme 21

Scheme 21 shows a process for making compounds of Formula I where ring A is coupled to Ring B to form $R^1$.

Alternatively, compounds of the type e can be coupled to compound b in the presence of coupling reagents (such as EDCI and HOBt) in the presence of a base (such as diisopropylethylamine) in a solvent (such as DMF) to afford compound f. Compound f can be reacted with bis(pinacolato)diborane in the presence of a palladium catalyst to afford compound g which can then be coupled to aryl or heteroaryl groups, where $X^1$ and $X^2$ are each independently selected from the group consisting of Cl and Br, in the presence of a palladium catalyst, to afford compounds of the type d.

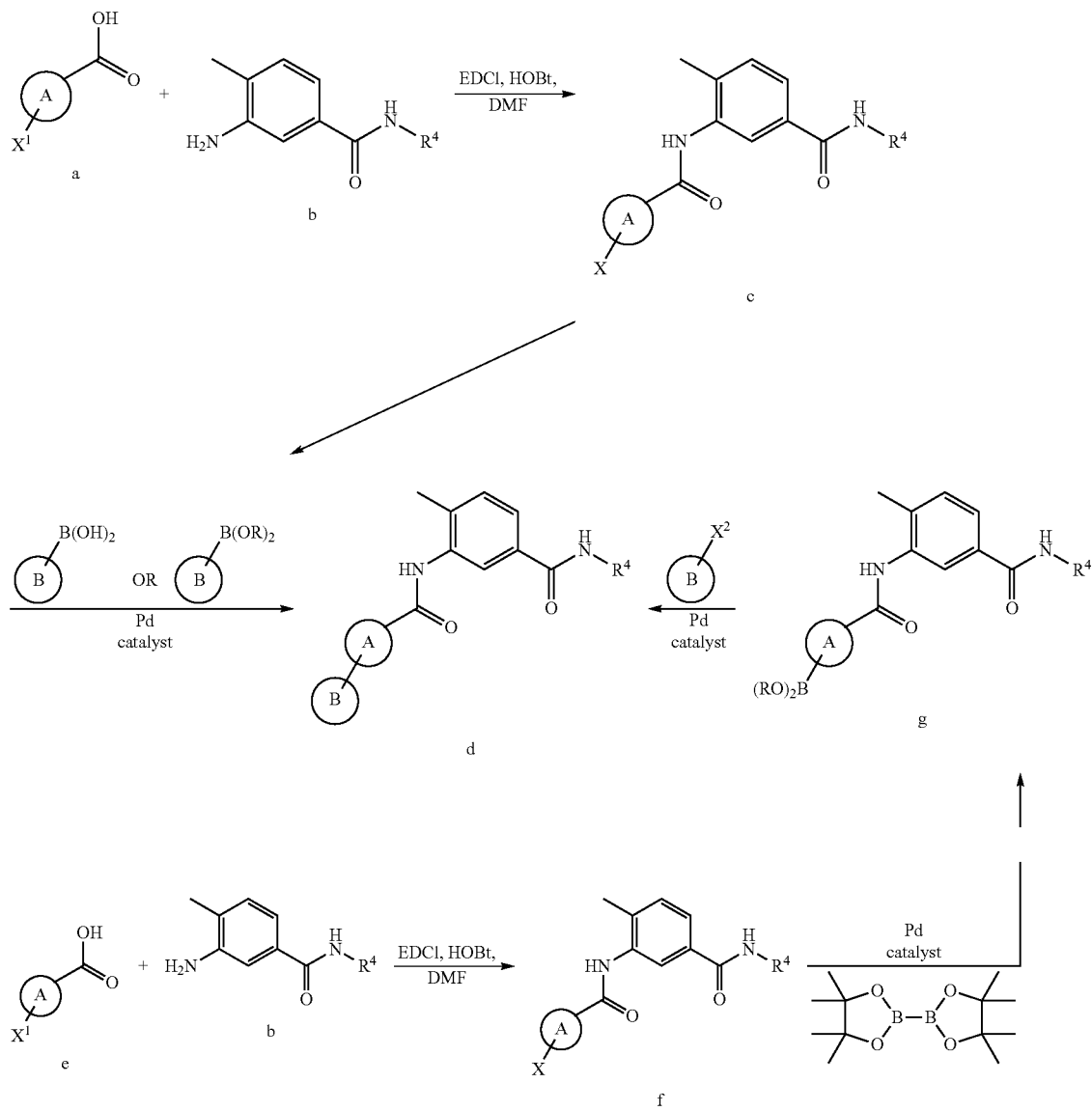

Compounds of the type d where ring A and ring B represent aryl or heteroaryl groups, can be prepared from compounds of the type a, where $X^1$ and $X^2$ are each independently selected from the group consisting of Cl or Br, as depicted in Scheme 1. Compound a can be coupled to compound b in the presence of a coupling reagent (such as EDCI and HOBt) in the presence of a base (such as diisopropylethylamine) in a solvent (such as DMF) to afford compound c. Compound c can be coupled with boronic acids or boronate esters in the presence of palladium catalysts to afford compounds of the type d.

SCHEME 22

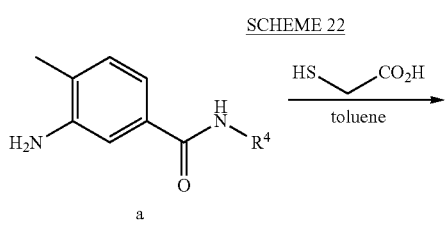

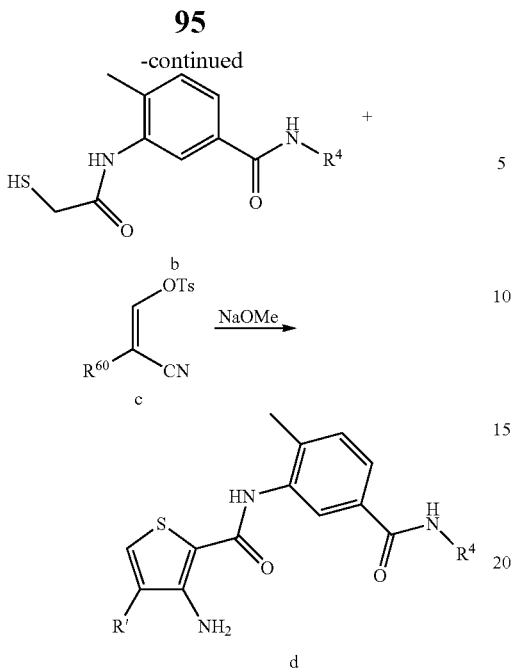

Compounds of the type d can be prepared as described as in Scheme 22. The hydrochloride salt of compound a can be reacted with mercaptoacetic acid in a solvent such as toluene to afford compound b. Compound b can be reacted with compound c in the presence of a base such as NaOMe as described in *J. Med. Chem.*, 6(47):1448 (2004) to afford compounds of the type d.

Example 127

5-(4-Chlorophenyl)-N-(5-(cyclopropylcarbamoyl)-2-methylphenyl)furan-2-carboxamide

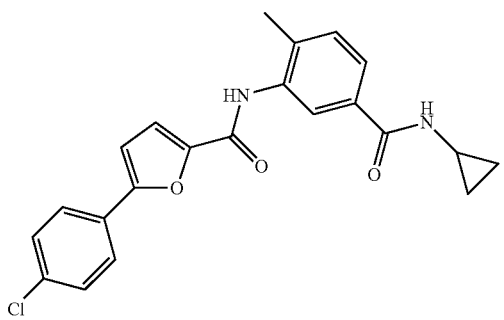 [SMILES: Cc1ccc(C(=O)NC2CC2)cc1NC(=O)c1ccc(-c2ccc(Cl)cc2)o1]

To a solution of 5-(4-chlorophenyl)furan-2-carboxylic acid (45 mg, 0.20 mmol) and 3-amino-N-cyclopropyl-4-methylbenzamide hydrochloride (prepared as described in WO 04/071440) (50 mg, 0.22 mmol) in DMF (0.5 mL) DIPEA (0.105 mL, 0.6 mmol) and the resulting mixture was stirred at rt for 1 h then at 80° C. for 1 h. The reaction was cooled to rt and water (3 mL) was added and the crude product was collected by vacuum filtration and dried under vacuum to afford 78 mg of a tan solid. The crude product was recrystallized from $CH_2Cl_2$ to afford 48 mg of a light tan solid as the title compound (Example 127). HPLC Ret. Time=3.52 min, LCMS $[M+H]^+$ 395.23.

Example 128

4'-Chloro-N-(5-(cyclopropylcarbamoyl)-2-methylphenyl)biphenyl-3-carboxamide

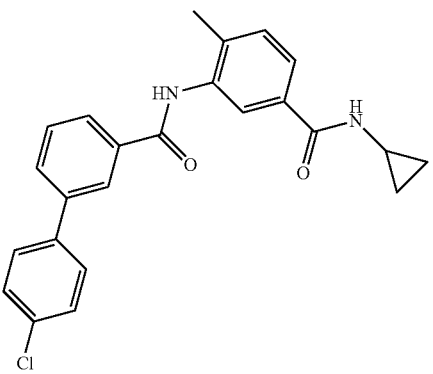 [SMILES: Cc1ccc(C(=O)NC2CC2)cc1NC(=O)c1cccc(-c2ccc(Cl)cc2)c1]

To a solution of 4'-chlorobiphenyl-3-carboxylic acid (40 mg, 0.17 mmol) in DMF (0.5 mL) was added EDCI (40 mg, 0.21 mmol) and HOBt (26 mg, 0.19 mmol) and the resulting solution was stirred at rt for 15 min. At this time, DIPEA (0.042 mL, 0.26 mmol) was added and the mixture was stirred at rt for ~16 h. Crushed ice (~2 mL volume) was added and the mixture was stirred for 2 h and the product was collected by vacuum filtration, washed with water and dried to afford 59 mg of a white solid as the title compound (Example 128). HPLC Ret. Time=3.67 min, LCMS $[M+H]^+$ 405.19.

Examples 129 to 135

Compounds listed in Table 6 were prepared using methods described in Example 128.

TABLE 6

| Example No. | Structure | Name | HPLC ret. Time, min. | LCMS $[M + H]^+$ |
|---|---|---|---|---|
| 129 | 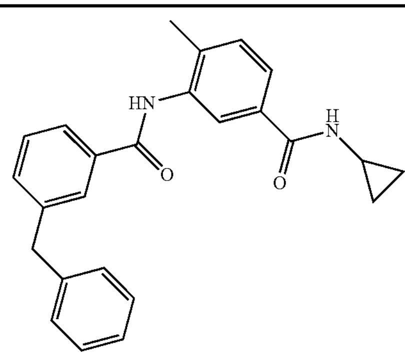 | 3-(3-benzylbenzamido)-N-cyclopropyl-4-methylbenzamide | 3.48** | 385.45 |

TABLE 6-continued

| Example No. | Name | HPLC ret. Time, min. | LCMS [M + H]+ |
|---|---|---|---|
| 130 | N-(5-(cyclopropylcarbamoyl)-2-methylphenyl)-5-(pyridin-2-yl)thiophene-2-carboxamide | 2.64** | 378.42 |
| 131 | N-(5-(cyclopropylcarbamoyl)-2-methylphenyl)-5-phenylthiophene-2-carboxamide | 3.43** | 377.42 |
| 132 | N-(5-(cyclopropylcarbamoyl)-2-methylphenyl)-5-(3-(trifluoromethyl)phenyl)furan-2-carboxamide | 3.62** | 429.39 |
| 133 | 3-(3-((1H-benzo[d]imidazol-1-yl)methyl)benzamido)-N-cyclopropyl-4-methylbenzamide | 1.99** | 425.44 |
| 134 | N-(5-(cyclopropylcarbamoyl)-2-methylphenyl)-5-(4-fluorophenyl)-1H-pyrrole-2-carboxamide | 3.31 | 378.30 |
| 135 | N-(5-(cyclopropylcarbamoyl)-2-methylphenyl)-4-phenylthiophene-2-carboxamide | 3.31 | 373.13 |

**HPLC conditions: Waters Sunfire C18; 4.6 × 50 mm (4 min. gradient); Flow rate = 4 mL/min; Solvent A = 10% MeOH, 90% H$_2$O, 0.1% TFA; solvent B = 90% MeOH, 10% H$_2$O, 0.1% TFA.

Example 136

5-(2-Chlorophenyl)-N-(5-(cyclopropylcarbamoyl)-2-methylphenyl)thiophene-2-carboxamide

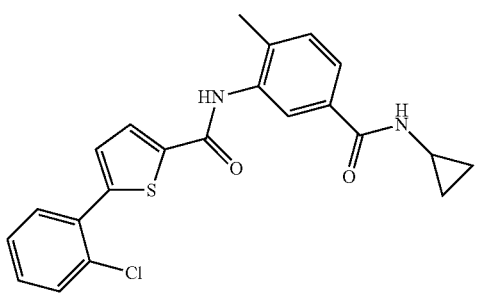 [SMILES: Cc1ccc(C(=O)NC2CC2)cc1NC(=O)c1ccc(-c2ccccc2Cl)s1]

Step A

5-Bromo-N-(5-(cyclopropylcarbamoyl)-2-methylphenyl)thiophene-2-carboxamide

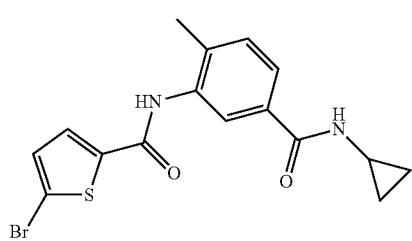

Compound a was prepared by coupling 5-bromothiophene-2-carboxylic acid with 3-amino-N-cyclopropyl-4-methylbenzamide hydrochloride (prepared as described in WO04071440) using the method described in Example 2. HPLC Ret time=3.16 min. LCMS [M+H]$^+$ 379.15.

Step B (2-Chlorophenyl)-N-(5-(cyclopropylcarbamoyl)-2-methylphenyl)thiophene-2-carboxamide 5-Bromo-N-(5-(cyclopropylcarbamoyl)-2-methylphenyl)thiophene-2-carboxamide (80 mg, 0.21 mmol) and 2-chlorophenylboronic acid (50 mg, 0.32 mmol) in toluene (0.7 mL) was purged with argon and ethanol (0.14 mL), 2 M aq. $K_3PO_4$ (0.21 mL, 0.42 mmol), and $Pd(PPh_3)_4$ (12 mg, 0.010 mmol) was added. The resulting mixture was heated at 115° C. for 2 h. After cooling to rt, the mixture was diluted with EtOAc (100 mL), washed with brine and dried over anyhd. sodium sulfate. The solution was filtered and concentrated under vacuum to afford a yellow solid which was triturated with MeOH (2 mL), filtered to collect the solid and rinsed with additional MeOH (2×0.5 mL) and dried under vacuum to afford 56 mg of a white solid as the title compound (Example 136). HPLC Ret time=3.56 min. LCMS [M+H]$^+$ 411.21.

Examples 137 to 179

Compounds listed in Table 7 were prepared using similar methods as described in Example 136.

TABLE 7

| Example No. | Structure | Name | HPLC ret. Time, min. (column conditions)* | LCMS [M + H]$^+$ |
| --- | --- | --- | --- | --- |
| 137 | 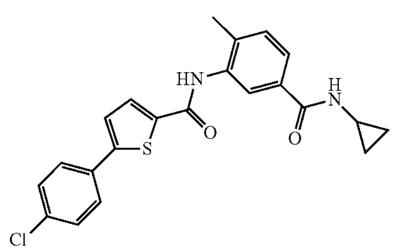 [SMILES: Cc1ccc(C(=O)NC2CC2)cc1NC(=O)c1ccc(-c2ccc(Cl)cc2)s1] | 3-(3-benzylbenzamido)-N-cyclopropyl-4-methylbenzamide | 3.67 | 411.10 |
| 138 | 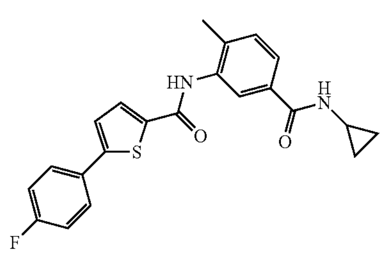 [SMILES: Cc1ccc(C(=O)NC2CC2)cc1NC(=O)c1ccc(-c2ccc(F)cc2)s1] | N-(5-(cyclopropylcarbamoyl)-2-methylphenyl)-5-(pyridin-3-yl)thiophene-2-carboxamide | 3.44 | 395.16 |

TABLE 7-continued

| Example No. | Structure | Name | HPLC ret. Time, min. (column conditions)* | LCMS [M + H]+ |
|---|---|---|---|---|
| 139 | 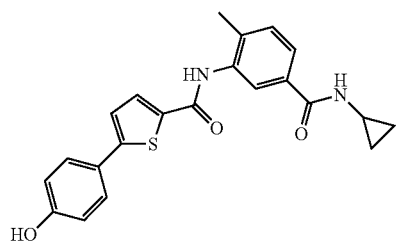 | N-(5-(cyclopropylcarbamoyl)-2-methylphenyl)-5-phenylthiophene-2-carboxamide | 2.95 | 393.16 |
| 140 | 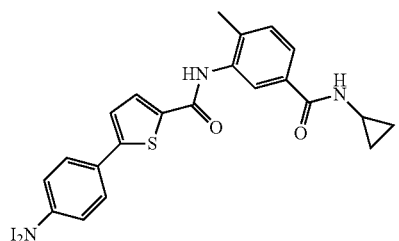 | N-(5-(cyclopropylcarbamoyl)-2-methylphenyl)-5-(3-(trifluoromethyl)phenyl)furan-2-carboxamide | 2.19 | 392.13 |
| 141 | 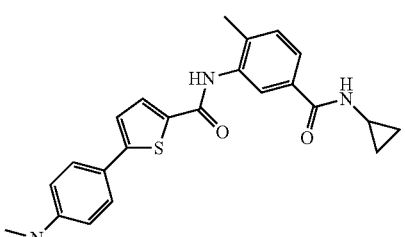 | 3-(3-((1H-benzo[d]imidazol-1-yl)methyl)benzamido)-N-cyclopropyl-4-methylbenzamide | 3.01 | 420.19 |
| 142 | 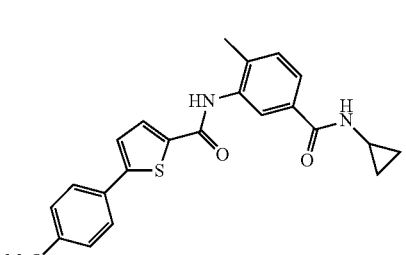 | N-(5-(cyclopropylcarbamoyl)-2-methylphenyl)-5-(4-methoxyphenyl)thiophene-2-carboxamide | 3.39 | 407.2 |
| 143 | 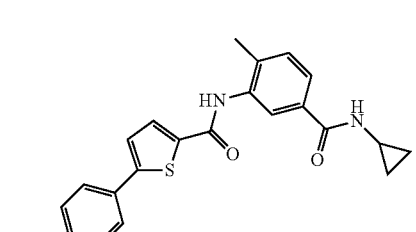 | N-(5-(cyclopropylcarbamoyl)-2-methylphenyl)-5-(4-(hydroxymethyl)phenyl)thiophene-2-carboxamide | 2.94 | 407.14 |
| 144 | 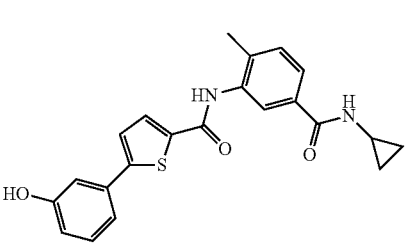 | N-(5-(cyclopropylcarbamoyl)-2-methylphenyl)-5-(3-hydroxyphenyl)thiophene-2-carboxamide | 4.04 | 393.14 |

TABLE 7-continued

| Example No. | Structure | Name | HPLC ret. Time, min. (column conditions)* | LCMS [M + H]+ |
|---|---|---|---|---|
| 145 | 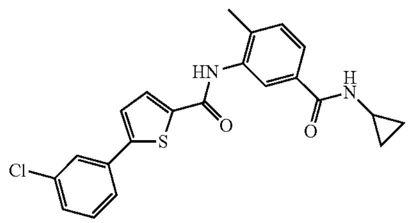 [SMILES: Cc1ccc(C(=O)NC2CC2)cc1NC(=O)c1ccc(-c2cccc(Cl)c2)s1] | N-(5-(cyclopropylcarbamoyl)-2-methylphenyl)-5-(3-chlorophenyl)thiophene-2-carboxamide | 3.66 | 411.07 |
| 146 | 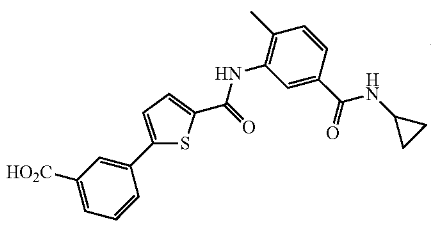 | 3-(5-(5-(cyclopropylcarbamoyl)-2-methylphenylcarbamoyl)thiophen-2-yl)benzoicacid | 3.16 | 421.15 |
| 147 | 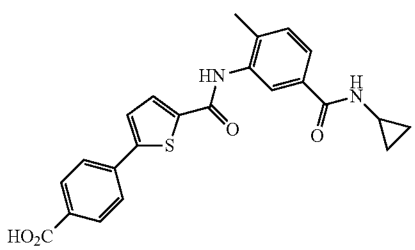 [SMILES: Cc1ccc(C(=O)NC2CC2)cc1NC(=O)c1ccc(-c2ccc(C(=O)O)cc2)s1] | 4-(5-(5-(cyclopropylcarbamoyl)-2-methylphenylcarbamoyl)thiophen-2-yl)benzoicacid | 3.09 | 421.15 |
| 148 | 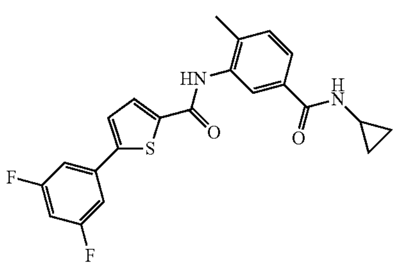 [SMILES: Cc1ccc(C(=O)NC2CC2)cc1NC(=O)c1ccc(-c2cc(F)cc(F)c2)s1] | N-(5-(cyclopropylcarbamoyl)-2-methylphenyl)-5-(3,5-difluorophenyl)thiophene-2-carboxamide | 3.61 | 413.11 |
| 149 | 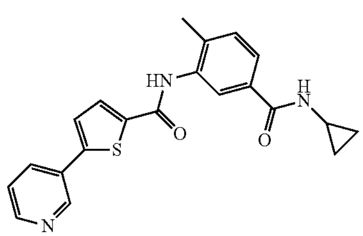 [SMILES: Cc1ccc(C(=O)NC2CC2)cc1NC(=O)c1ccc(-c2cccnc2)s1] | N-(5-(cyclopropylcarbamoyl)-2-methylphenyl)-5-(pyridin-3-yl)thiophene-2-carboxamide | 2.08 | 378.13 |
| 150 | 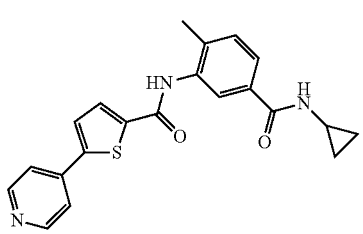 [SMILES: Cc1ccc(C(=O)NC2CC2)cc1NC(=O)c1ccc(-c2ccncc2)s1] | N-(5-(cyclopropylcarbamoyl)-2-methylphenyl)-5-(pyridin-4-yl)thiophene-2-carboxamide | 1.86 | 378.13 |

TABLE 7-continued

| Example No. | Structure | Name | HPLC ret. Time, min. (column conditions)* | LCMS [M + H]+ |
| --- | --- | --- | --- | --- |
| 151 | 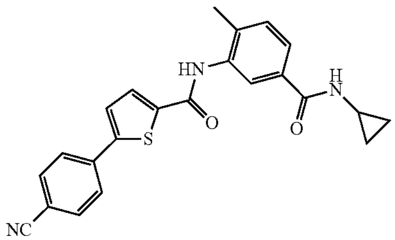 [SMILES: Cc1ccc(C(=O)NC2CC2)cc1NC(=O)c1ccc(-c2ccc(C#N)cc2)s1] | 5-(4-cyanophenyl)-N-(5-(cyclopropylcarbamoyl)-2-methylphenyl)thiophene-2-carboxamide | 3.15 | 402.11 |
| 152 | 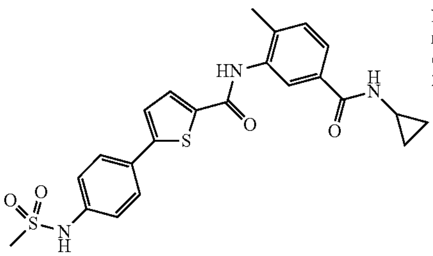 [SMILES: Cc1ccc(C(=O)NC2CC2)cc1NC(=O)c1ccc(-c2ccc(NS(C)(=O)=O)cc2)s1] | N-(5-(cyclopropylcarbamoyl)-2-methylphenyl)-5-(4-(methylsulfonamido)phenyl)thiophene-2-carboxamide | 2.85 | 470.11 |
| 153 | 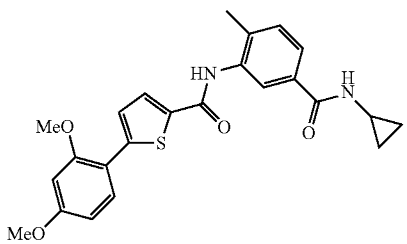 [SMILES: COc1ccc(-c2ccc(C(=O)Nc3cc(C(=O)NC4CC4)ccc3C)s2)c(OC)c1] | N-(5-(cyclopropylcarbamoyl)-2-methylphenyl)-5-(2,4-dimethoxyphenyl)thiophene-2-carboxamide | 3.4 | 427.18 |
| 154 | 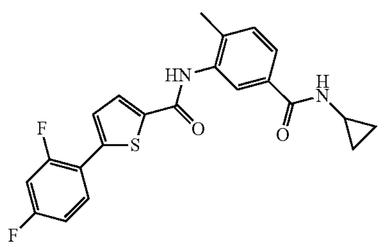 [SMILES: Cc1ccc(C(=O)NC2CC2)cc1NC(=O)c1ccc(-c2ccc(F)cc2F)s1] | N-(5-(cyclopropylcarbamoyl)-2-methylphenyl)-5-(2,4-difluorophenyl)thiophene-2-carboxamide | 3.46 | 413.08 |
| 155 | 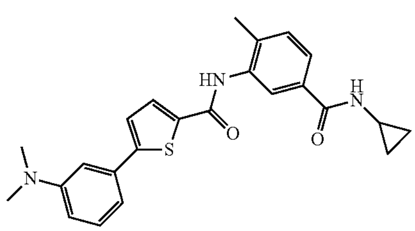 [SMILES: Cc1ccc(C(=O)NC2CC2)cc1NC(=O)c1ccc(-c2cccc(N(C)C)c2)s1] | N-(5-(cyclopropylcarbamoyl)-2-methylphenyl)-5-(3-(dimethylamino)phenyl)thiophene-2-carboxamide | 2.66 | 420.18 |
| 156 | 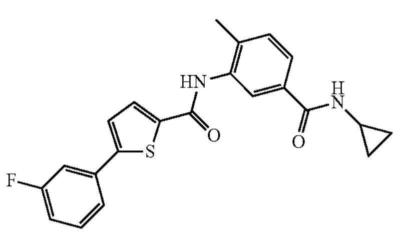 [SMILES: Cc1ccc(C(=O)NC2CC2)cc1NC(=O)c1ccc(-c2cccc(F)c2)s1] | N-(5-(cyclopropylcarbamoyl)-2-methylphenyl)-5-(3-fluorophenyl)thiophene-2-carboxamide | 3.43 | 395.12 |

TABLE 7-continued

| Example No. | Name | HPLC ret. Time, min. (column conditions)* | LCMS [M + H]⁺ |
|---|---|---|---|
| 157 | 5-(3-cyanophenyl)-N-(5-(cyclopropylcarbamoyl)-2-methylphenyl)thiophene-2-carboxamide | 3.15 | 402.09 |
| 158 | N-(5-(cyclopropylcarbamoyl)-2-methylphenyl)-5-(3-methoxyphenyl)thiophene-2-carboxamide | 3.45 | 407.2 |
| 159 | 5-(3-aminophenyl)-N-(5-(cyclopropylcarbamoyl)-2-methylphenyl)thiophene-2-carboxamide | 2.21 | 392.3 |
| 160 | N-(5-(cyclopropylcarbamoyl)-2-methylphenyl)-5-(3-(hydroxymethyl)phenyl)thiophene-2-carboxamide | 2.94 | 407.2 |
| 161 | N-(5-(cyclopropylcarbamoyl)-2-methylphenyl)-5-(2-fluorophenyl)thiophene-2-carboxamide | 3.36 | 395.3 |
| 162 | N-(5-(cyclopropylcarbamoyl)-2-methylphenyl)-5-(4-(trifluoromethyl)phenyl)thiophene-2-carboxamide | 3.71 | 445.3 |

TABLE 7-continued

| Example No. | Structure | Name | HPLC ret. Time, min. (column conditions)* | LCMS [M + H]+ |
|---|---|---|---|---|
| 163 | 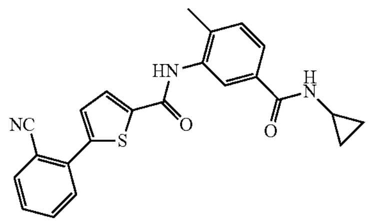 [SMILES: Cc1ccc(C(=O)NC2CC2)cc1NC(=O)c1ccc(-c2ccccc2C#N)s1] | 5-(2-cyanophenyl)-N-(5-(cyclopropylcarbamoyl)-2-methylphenyl)thiophene-2-carboxamide | 3.08 | 402.18 |
| 164 | 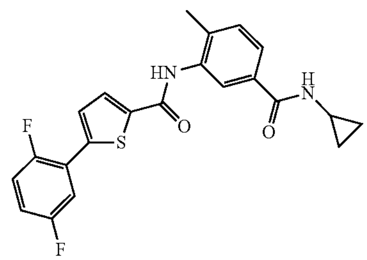 [SMILES: Cc1ccc(C(=O)NC2CC2)cc1NC(=O)c1ccc(-c2cc(F)ccc2F)s1] | N-(5-(cyclopropylcarbamoyl)-2-methylphenyl)-5-(2,5-difluorophenyl)thiophene-2-carboxamide | 3.47 | 413.3 |
| 165 | 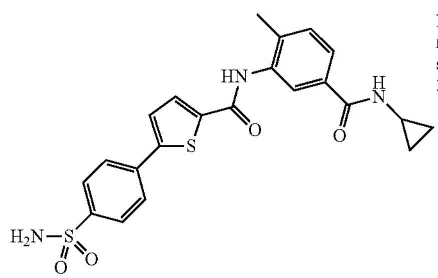 | N-(5-(cyclopropylcarbamoyl)-2-methylphenyl)-5-(4-sulfamoylphenyl)thiophene-2-carboxamide | 2.58 | 456.13 |
| 166 | 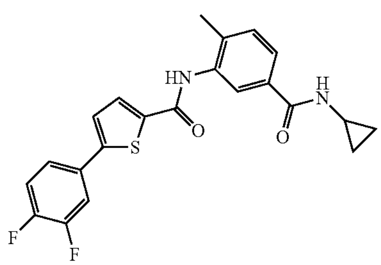 [SMILES: Cc1ccc(C(=O)NC2CC2)cc1NC(=O)c1ccc(-c2ccc(F)c(F)c2)s1] | N-(5-(cyclopropylcarbamoyl)-2-methylphenyl)-5-(3,4-difluorophenyl)thiophene-2-carboxamide | 3.51 | 413.19 |
| 167 | 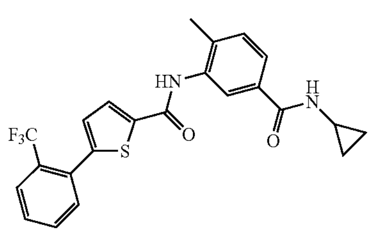 [SMILES: Cc1ccc(C(=O)NC2CC2)cc1NC(=O)c1ccc(-c2ccccc2C(F)(F)F)s1] | N-(5-(cyclopropylcarbamoyl)-2-methylphenyl)-5-(2-(trifluoromethyl)phenyl)thiophene-2-carboxamide | 3.46 | 445.18 |
| 168 | 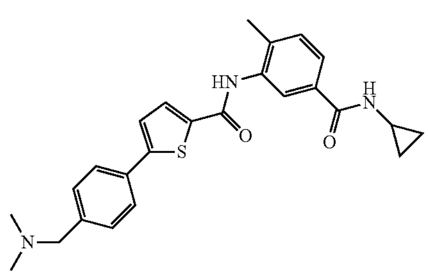 [SMILES: Cc1ccc(C(=O)NC2CC2)cc1NC(=O)c1ccc(-c2ccc(CN(C)C)cc2)s1] | N-(5-(cyclopropylcarbamoyl)-2-methylphenyl)-5-(4-((dimethylamino)methyl)phenyl)thiophene-2-carboxamide | 3.24 | 420.21 |

TABLE 7-continued

| Example No. | Structure | Name | HPLC ret. Time, min. (column conditions)* | LCMS [M + H]+ |
| --- | --- | --- | --- | --- |
| 169 | 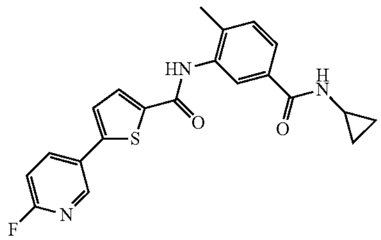 [SMILES: Cc1ccc(C(=O)NC2CC2)cc1NC(=O)c1ccc(-c2ccc(F)nc2)s1] | N-(5-(cyclopropylcarbamoyl)-2-methylphenyl)-5-(6-fluoropyridin-3-yl)thiophene-2-carboxamide | 3.49 | 391.26 |
| 170 | 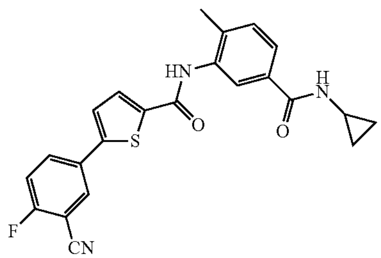 [SMILES: Cc1ccc(C(=O)NC2CC2)cc1NC(=O)c1ccc(-c2ccc(F)c(C#N)c2)s1] | 5-(3-cyano-4-fluorophenyl)-N-(5-(cyclopropylcarbamoyl)-2-methylphenyl)thiophene-2-carboxamide | 2.14 | 463.25 |
| 171 | 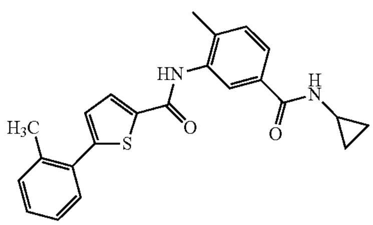 [SMILES: Cc1ccc(C(=O)NC2CC2)cc1NC(=O)c1ccc(-c2ccccc2C)s1] | N-(5-(cyclopropylcarbamoyl)-2-methylphenyl)-5-o-tolylthiophene-2-carboxamide | 3.18 | 408.25 |
| 172 | 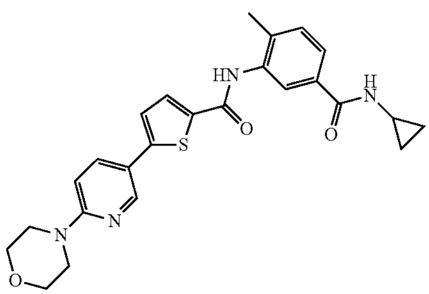 [SMILES: Cc1ccc(C(=O)NC2CC2)cc1NC(=O)c1ccc(-c2ccc(N3CCOCC3)nc2)s1] | N-(5-(cyclopropylcarbamoyl)-2-methylphenyl)-5-(6-morpholinopyridin-3-yl)thiophene-2-carboxamide | 2.89 | 396.1 |
| 173 | 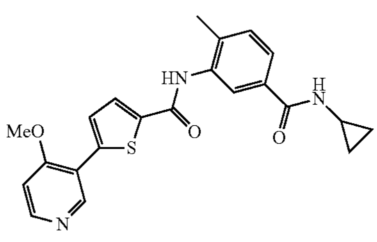 [SMILES: COc1ccncc1-c1ccc(C(=O)Nc2cc(C(=O)NC3CC3)ccc2C)s1] | N-(5-(cyclopropylcarbamoyl)-2-methylphenyl)-5-(4-methoxypyridin-3-yl)thiophene-2-carboxamide | 3.26 | 420.19 |
| 174 | 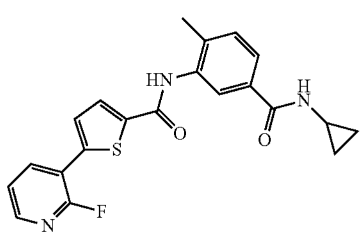 [SMILES: Cc1ccc(C(=O)NC2CC2)cc1NC(=O)c1ccc(-c2cccnc2F)s1] | N-(5-(cyclopropylcarbamoyl)-2-methylphenyl)-5-(2-fluoropyridin-3-yl)thiophene-2-carboxamide | 3.24 | 420.21 |

TABLE 7-continued

| Example No. | Structure | Name | HPLC ret. Time, min. (column conditions)* | LCMS [M + H]+ |
|---|---|---|---|---|
| 175 | 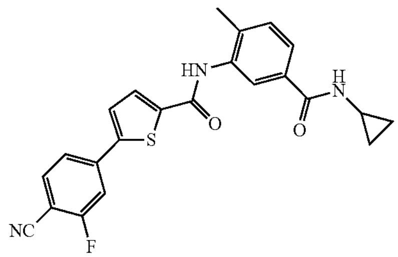 [SMILES: Cc1ccc(C(=O)NC2CC2)cc1NC(=O)c1ccc(-c2ccc(C#N)c(F)c2)s1] | 5-(4-cyano-3-fluorophenyl)-N-(5-(cyclopropylcarbamoyl)-2-methylphenyl)thiophene-2-carboxamide | 3.49 | 391.26 |
| 176 | 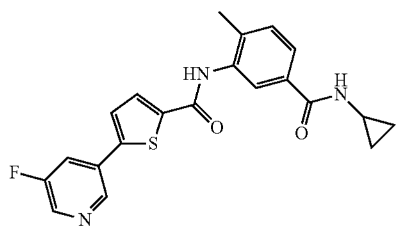 [SMILES: Cc1ccc(C(=O)NC2CC2)cc1NC(=O)c1ccc(-c2cncc(F)c2)s1] | N-(5-(cyclopropylcarbamoyl)-2-methylphenyl)-5-(5-fluoropyridin-3-yl)thiophene-2-carboxamide | 2.94 | 396.23 |
| 177 | 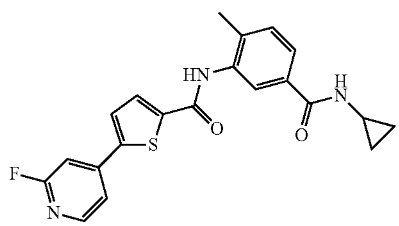 | N-(5-(cyclopropylcarbamoyl)-2-methylphenyl)-5-(2-fluoropyridin-4-yl)thiophene-2-carboxamide | 3 | 396.23 |
| 178 | 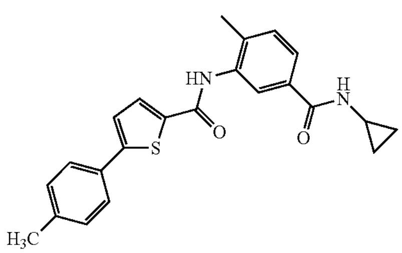 [SMILES: Cc1ccc(-c2ccc(C(=O)Nc3cc(C(=O)NC4CC4)ccc3C)s2)cc1] | N-(5-(cyclopropylcarbamoyl)-2-methylphenyl)-5-p-tolylthiophene-2-carboxamide | 3.66 | 391.3 |
| 179 | 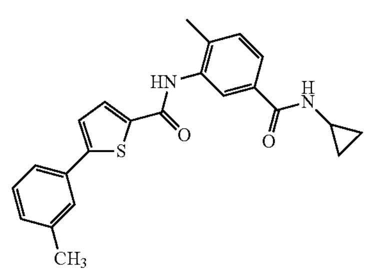 [SMILES: Cc1cccc(-c2ccc(C(=O)Nc3cc(C(=O)NC4CC4)ccc3C)s2)c1] | N-(5-(cyclopropylcarbamoyl)-2-methylphenyl)-5-m-tolylthiophene-2-carboxamide | 3.6 | 391.3 |

*(A): YMC S5 Combiscreen ODS ; 4.6 × 50 mm (4 min. gradient); Flow rate = 4 mL/min; Solvent A = 10% MeOH, 90% H2O, 0.2% $H_3PO_4$; solvent B = 90% MeOH, 10% $H_2O$, 0.2% $H_3PO_4$.

Example 180

N-(5-(Cyclopropylcarbamoyl)-2-methylphenyl)-5-(4-(methylcarbamoyl)phenyl)thiophene-2-carboxamide

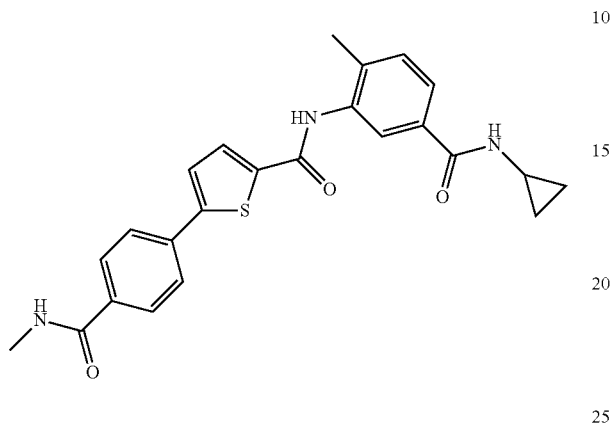

The title compound (Example 180) was prepared by reacting Example 21 with methylamine using the method described in Example 128 to afford a white solid in 93% yield. HPLC Ret. Time=2.82 min, LCMS [M+H]$^+$ 434.17.

Examples 181 to 185

Compounds listed in Table 8 were prepared as in Example 180 using the method described in Example 128.

TABLE 8

| Example No. | Structure | Name | HPLC ret. Time, min. (column conditions)* | LCMS [M+ H]$^+$ |
|---|---|---|---|---|
| 181 | 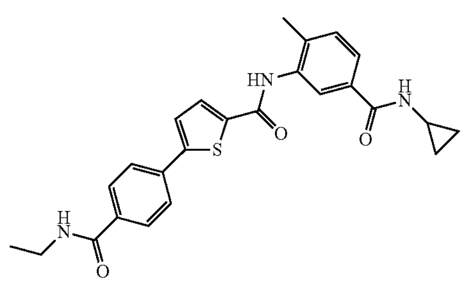 [SMILES: CCNC(=O)c1ccc(-c2ccc(C(=O)Nc3cc(C(=O)NC4CC4)ccc3C)s2)cc1] | N-(5-(cyclopropylcarbamoyl)-2-methylphenyl)-5-(4-(ethylcarbamoyl)phenyl)thiophene-2-carboxamide | 2.97 | 448.21 |
| 182 | 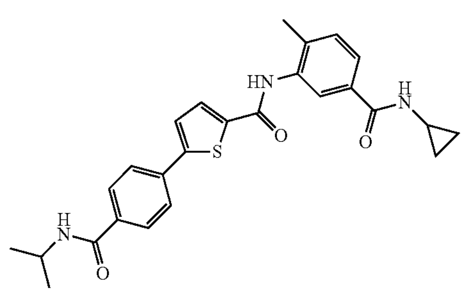 [SMILES: Cc1ccc(C(=O)NC2CC2)cc1NC(=O)c1ccc(-c2ccc(C(=O)NC(C)C)cc2)s1] | N-(5-(cyclopropylcarbamoyl)-2-methylphenyl)-5-(4-(isopropylcarbamoyl)phenyl)thiophene-2-carboxamide | 3.1 | 462.16 |

TABLE 8-continued

| Example No. | Structure | Name | HPLC ret. Time, min. (column conditions)* | LCMS [M+ H]+ |
|---|---|---|---|---|
| 183 | 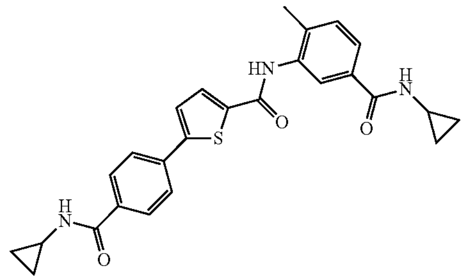 [SMILES: Cc1ccc(C(=O)NC2CC2)cc1NC(=O)c1ccc(-c2ccc(C(=O)NC3CC3)cc2)s1] | N-(5-(cyclopropylcarbamoyl)-2-methylphenyl)-5-(4-(cyclopropylcarbamoyl)phenyl)thiophene-2-carboxamide | 3 | 460.15 |
| 184 | 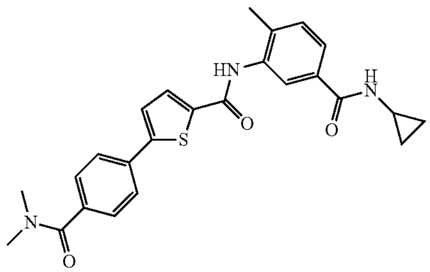 [SMILES: Cc1ccc(C(=O)NC2CC2)cc1NC(=O)c1ccc(-c2ccc(C(=O)N(C)C)cc2)s1] | N-(5-(cyclopropylcarbamoyl)-2-methylphenyl)-5-(4-(dimethylcarbamoyl)phenyl)thiophene-2-carboxamide | 2.88 | 448.18 |
| 185 | 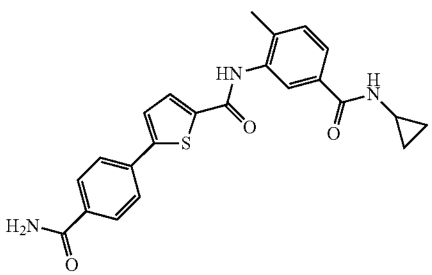 [SMILES: Cc1ccc(C(=O)NC2CC2)cc1NC(=O)c1ccc(-c2ccc(C(N)=O)cc2)s1] | 5-(4-carbamoylphenyl)-N-(5-(cyclopropylcarbamoyl)-2-methylphenyl)thiophene-2-carboxamide | 2.68 | 420.16 |

Example 186

5-(4-Chlorophenyl)-N-(2-methyl-5-(methylcarbamoyl)phenyl)thiophene-2-carboxamide

Step A

Methyl 3-(5-bromothiophene-2-carboxamido)-4-methylbenzoate

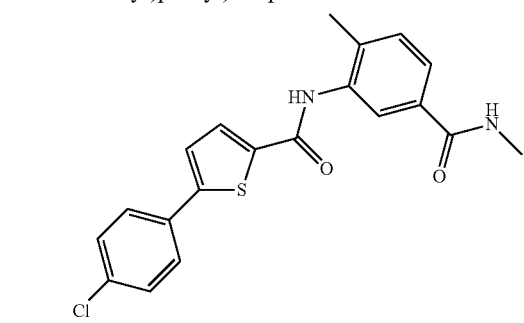

a

Compound a was prepared by coupling 5-bromothiophene-2-carboxylic acid with commercially available methyl 3-amino-4-methylbenzoate using the method described in Example 128 to afford a white solid in 88% yield. HPLC Ret time=3.25 min. LCMS [M+H]+ 355.2.

Step B

Methyl 3-(5-(4-chlorophenyl)thiophene-2-carboxamido)-4-methylbenzoate

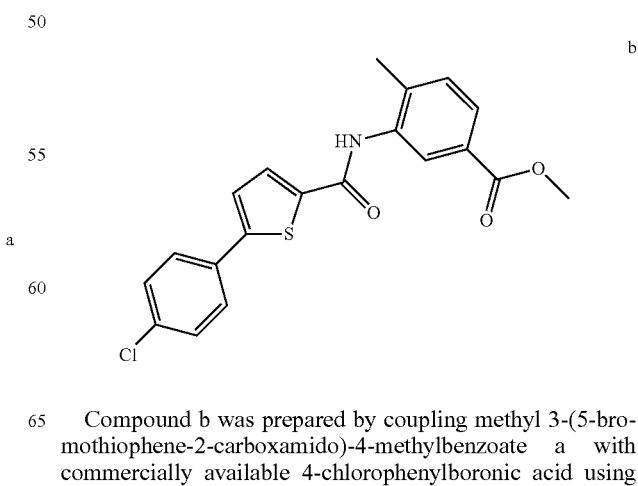

b

Compound b was prepared by coupling methyl 3-(5-bromothiophene-2-carboxamido)-4-methylbenzoate a with commercially available 4-chlorophenylboronic acid using the method described in Step B of Example 136 to afford an off-white solid in 82% yield. HPLC Ret time=3.78 min. LCMS [M+H]+ 386.09.
Step C 3-(5-(4-Chlorophenyl)thiophene-2-carboxamido)-4-methylbenzoic acid

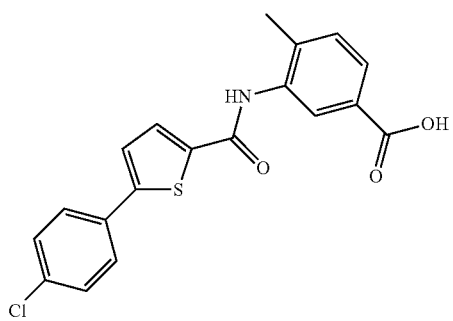

c

Methyl 3-(5-(4-chlorophenyl)thiophene-2-carboxamido)-4-methylbenzoate b (640 mg, 1.66 mmol) was slurried in 1:1 THF/MeOH (10 mL) and 3 N aq. NaOH (2 mL) was added. After stirring overnight at rt, the reaction mixture was filtered then concentrated under vacuum to remove the volatile solvents. The remaining aqueous portion was diluted with water (~5 mL) and made acidic (pH~1) by adding 1 N aq HCl. The resulting slurry was stirred for 2 h then the solid was collected by vacuum filtration. The solid was washed with water then allowed to air dry in funnel to afford 620 mg of compound c as a white solid. HPLC Ret time=3.61 min. LCMS [M+H]+ 372.05.
Step D 5-(4-Chlorophenyl)-N-(2-methyl-5-(methylcarbamoyl)phenyl)thiophene-2-carboxamide The title compound (Example 186) was prepared by reacting 3-(5-(4-chlorophenyl)thiophene-2-carboxamido)-4-methylbenzoic acid c with methylamine using the method described in Example 128 to afford a white solid in 73% yield. HPLC Ret. Time=3.51 min, LCMS [M+H]+ 385.08.

Examples 187 to 191

Compounds listed in Table 9 were prepared using a similar method described in Example 186.

TABLE 9

| Example No. | Structure | Name | HPLC ret. Time, min. (column conditions)* | LCMS [M+ H]+ |
|---|---|---|---|---|
| 187 | 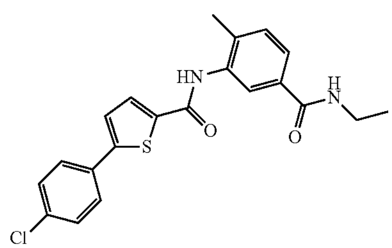 [SMILES: CCNC(=O)c1ccc(C)c(NC(=O)c2ccc(-c3ccc(Cl)cc3)s2)c1] | 5-(4-chlorophenyl)-N-(5-(ethylcarbamoyl)-2-methylphenyl)thiophene-2-carboxamide | 3.64 | 399.1 |
| 188 | 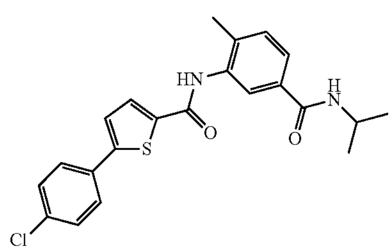 [SMILES: Cc1ccc(C(=O)NC(C)C)cc1NC(=O)c1ccc(-c2ccc(Cl)cc2)s1] | 5-(4-fluorophenyl)-N-(5-(isopropylcarbamoyl)-2-methylphenyl)thiophene-2-carboxamide | 3.75 | 413.09 |
| 189 | 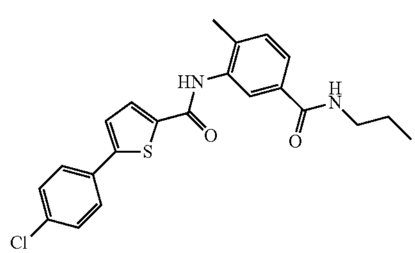 [SMILES: CCCNC(=O)c1ccc(C)c(NC(=O)c2ccc(-c3ccc(Cl)cc3)s2)c1] | 5-(4-chlorophenyl)-N-(2-methyl-5-(propylcarbamoyl)phenyl)thiophene-2-carboxamide | 3.74 | 413.1 |

TABLE 9-continued

| Example No. | Structure | Name | HPLC ret. Time, min. (column conditions)* | LCMS [M+ H]+ |
|---|---|---|---|---|
| 190 | 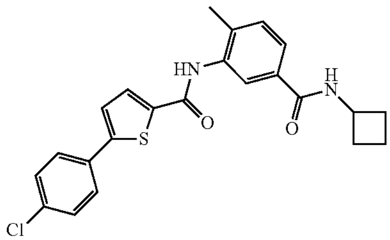 [SMILES: Cc1ccc(C(=O)NC2CCC2)cc1NC(=O)c1ccc(-c2ccc(Cl)cc2)s1] | 5-(4-chlorophenyl)-N-(5-(cyclobutylcarbamoyl)-2-methylphenyl)thiophene-2-carboxamide | 3.8 | 425.13 |
| 191 | 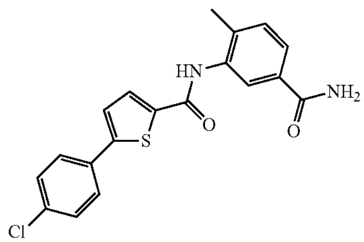 [SMILES: Cc1ccc(C(N)=O)cc1NC(=O)c1ccc(-c2ccc(Cl)cc2)s1] | N-(5-carbamoyl-2-methylphenyl)-5-(4-chlorophenyl)thiophene-2-carboxamide | 3.45 | 371.08 |

Example 192

N-(5-(Cyclopropylcarbamoyl)-2-methylphenyl)-5-(3-(cyclopropylcarbamoyl)phenyl)thiophene-2-carboxamide

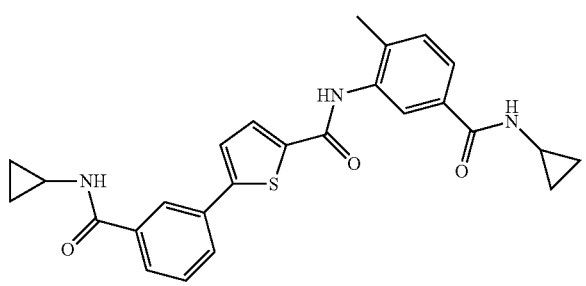 [SMILES: Cc1ccc(C(=O)NC2CC2)cc1NC(=O)c1ccc(-c2cccc(C(=O)NC3CC3)c2)s1]

The title compound (Example 192) was prepared by reacting Example 146 with cyclopropylamine using the method described in Example 128 to afford a white solid in 94% yield. HPLC Ret. Time=3.06 min, LCMS [M+H]+ 460.21.

Example 193

(R)—N-(5-(Cyclopropylcarbamoyl)-2-methylphenyl)-5-(3-(2,3-dihydroxypropoxy)phenyl)thiophene-2-carboxamide

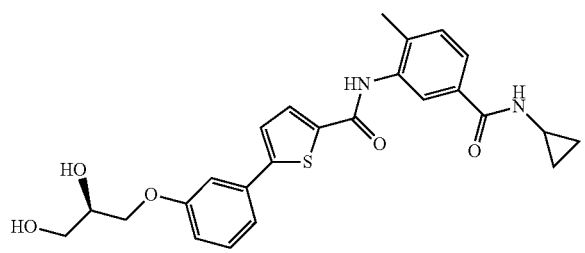 [SMILES: Cc1ccc(C(=O)NC2CC2)cc1NC(=O)c1ccc(-c2cccc(OC[C@H](O)CO)c2)s1]

A mixture of N-(5-(cyclopropylcarbamoyl)-2-methylphenyl)-5-(3-hydroxyphenyl)thiophene-2-carboxamide (Example 144, 80 mg, 0.20 mmol), (R)-(−)-2,2-dimethyl-1,3-dioxolan-4-ylmethyl p-toluenesulfonate (70 mg, 0.24 mmol) and K$_2$CO$_3$ (84 mg, 0.61 mmol) in DMF (0.3 mL) was stirred and heated at 80° C. for 17 h. After cooling to rt, the mixture was diluted with water (~5 mL) and extracted with EtOAc (3×10 mL) and the combined extracts were washed with brine, dried over anhyd. Na$_2$SO$_4$, filtered, and concentrated under vacuum to afford a brown oil. This material was purified by reverse-phase Prep HPLC to isolate the major product which was dissolved in MeOH (~3 mL) and 2 N aq HCl (0.3 mL) was added. The solution was warmed to 65° C. for 45 min then cooled to rt and concentrated under vacuum to remove most of the MeOH. The resulting heterogeneous mixture was diluted with water (~2-3 mL) and stirred for 1 h. The resulting solid was collected by vacuum filtration, rinsed with water (~5 mL), and air dried in funnel then under vacuum to afford 29 mg (30%) of an off-white solid as the title compound (Example 193). HPLC Ret. Time=2.90 min, LCMS [M+H]+ 467.29.

Example 194

(S)—N-(5-(Cyclopropylcarbamoyl)-2-methylphenyl)-5-(3-(2,3-dihydroxypropoxy)phenyl)thiophene-2-carboxamide

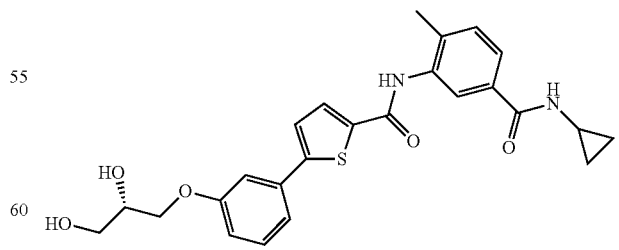

The title compound (Example 194) was prepared from (S)-(+2,2-dimethyl-1,3-dioxolan-4-ylmethyl p-toluenesulfonate using the method described in Example 193 to afford an off-white solid (Example 194) in 34% yield. HPLC Ret. Time=2.90 min, LCMS [M+H]+ 467.26.

Example 195

(R)—N-(5-(Cyclopropylcarbamoyl)-2-methylphenyl)-5-(4-(2,3-dihydroxypropoxy)phenyl)thiophene-2-carboxamide

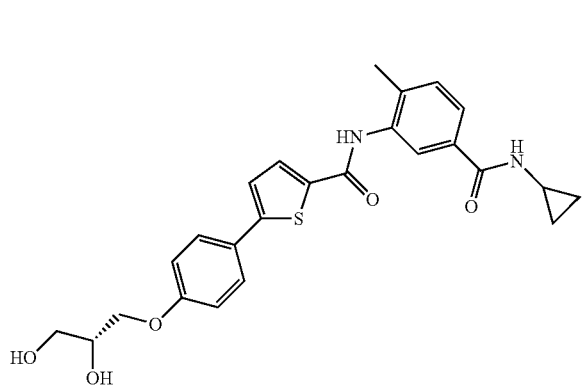 [SMILES: Cc1ccc(C(=O)NC2CC2)cc1NC(=O)c1ccc(-c2ccc(OC[C@H](O)CO)cc2)s1]

The title compound (Example 195) was prepared from Example 139 and (R)-(−)-2,2-dimethyl-1,3-dioxolan-4-ylmethyl p-toluenesulfonate using the method described in Example 68 to afford an off-white solid (Example 195) in 67% yield. HPLC Ret. Time=2.84 min, LCMS [M+H]$^+$ 467.20.

Example 196

3-(5-(5-(Cyclopropylcarbamoyl)-2-methylphenylcarbamoyl)thiophen-2-yl)pyridine 1-oxide

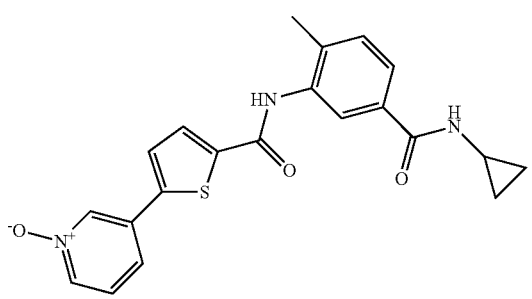

To a slurry of N-(5-(cyclopropylcarbamoyl)-2-methylphenyl)-5-(pyridin-3-yl)thiophene-2-carboxamide (Example 149, 30 mg, 0.079 mmol) in CH$_2$Cl$_2$ (0.5 mL) at rt was added m-CPBA (19 mg, 0.083 mmol) and the resulting slurry was stirred at rt for 30 min then at 35° C. for 4.5 h. The mixture was concentrated under vacuum and the resulting solid was slurried in MeOH (~2 mL) and the solid was collected by vacuum filtration and rinsed with add'n MeOH (~1 mL). The resulting solid was dried in the funnel then under vacuum overnight to afford 25 mg (80%) of an off-white solid as the title compound (Example 196). HPLC Ret. Time=2.34 min, LCMS [M+H]$^+$ 394.10.

Example 197

4-(4-Chlorophenyl)-N-(5-(cyclopropylcarbamoyl)-2-methylphenyl)-3-methylthiophene-2-carboxamide

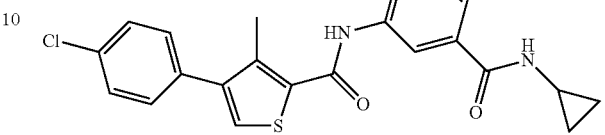

Step A

4-Bromo-N-(5-(cyclopropylcarbamoyl)-2-methylphenyl)-3-methylthiophene-2-carboxamide

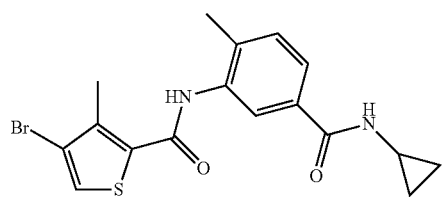

a

The compound a was prepared by coupling commercially available 4-bromo-3-methylthiophene-2-carboxylic acid with 3-amino-N-cyclopropyl-4-methylbenzamide hydrochloride (prepared as described in WO 04/071440) using the method described in Example 128. HPLC Ret time=3.12 min. LCMS [M+H]$^+$ 393.13.

Step B 4-(4-Chlorophenyl)-N-(5-(cyclopropylcarbamoyl)-2-methylphenyl)-3-methylthiophene-2-carboxamide The title compound was prepared by coupling 4-bromo-N-(5-(cyclopropylcarbamoyl)-2-methylphenyl)-3-methylthiophene-2-carboxamide a with commercially available 4-chlorophenylboronic acid using the method described in Step B of Example 136 to afford a white solid (Example 197). HPLC Ret time=3.67 min. LCMS [M+H]$^+$ 425.17.

Example 198

N-(5-(Cyclopropylcarbamoyl)-2-methylphenyl)-3-methyl-4-(pyridin-3-yl)thiophene-2-carboxamide

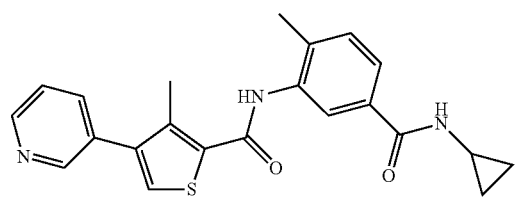 [SMILES: Cc1ccc(C(=O)NC2CC2)cc1NC(=O)c1scc(-c2cccnc2)c1C]

The title compound was prepared by coupling 4-bromo-N-(5-(cyclopropylcarbamoyl)-2-methylphenyl)-3-methylthiophene-2-carboxamide with commercially available 3-pyridylboronic acid using the method described in Step B of Example 136 to afford a white solid (Example 198). HPLC Ret time=1.98 min. LCMS [M+H]$^+$ 392.29.

Example 199

N-(5-(Cyclopropylcarbamoyl)-2-methylphenyl)-4-(6-fluoropyridin-3-yl)-3-methylthiophene-2-carboxamide

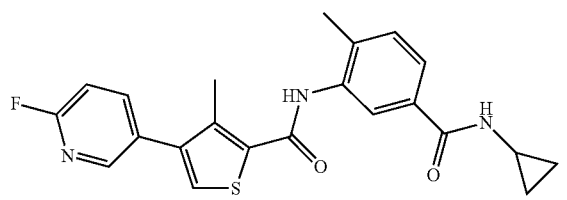 [SMILES: Cc1ccc(C(=O)NC2CC2)cc1NC(=O)c1scc(-c2ccc(F)nc2)c1C]

The title compound was prepared by coupling 4-bromo-N-(5-(cyclopropylcarbamoyl)-2-methylphenyl)-3-methylthiophene-2-carboxamide with commercially available 6-fluoropyridin-3-ylboronic acid using the method described in Step B of Example 136 to afford a white solid (Example 199). HPLC Ret time=2.98 min. LCMS [M+H]$^+$ 410.25.

Example 200

N-(5-(Cyclopropylcarbamoyl)-2-methylphenyl)-4-(5-fluoropyridin-3-yl)-3-methylthiophene-2-carboxamide

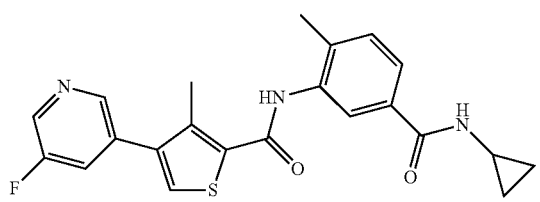 [SMILES: Cc1ccc(C(=O)NC2CC2)cc1NC(=O)c1scc(-c2cncc(F)c2)c1C]

The title compound was prepared by coupling 4-bromo-N-(5-(cyclopropylcarbamoyl)-2-methylphenyl)-3-methylthiophene-2-carboxamide with commercially available 3-fluoro-5-(4,4,5,5-tetramethyl-1,3,2-dioxaborolan-2-yl)pyridine using the method described in Step B of Example 136 to afford a white solid (Example 200). HPLC Ret time=2.98 min. LCMS [M+H]$^+$ 410.22.

Example 201

5-(4-Chlorophenyl)-N-(5-(cyclopropylcarbamoyl)-2-methylphenyl)thiophene-3-carboxamide

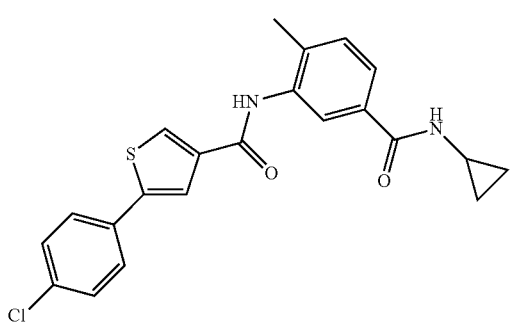

Step A

5-Bromo-N-(5-(cyclopropylcarbamoyl)-2-methylphenyl)thiophene-3-carboxamide

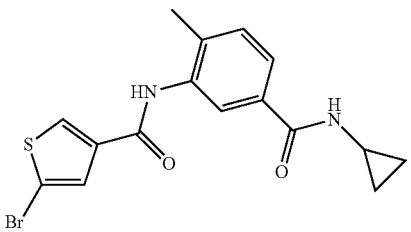 [SMILES: Cc1ccc(C(=O)NC2CC2)cc1NC(=O)c1csc(Br)c1]

Compound a was prepared by coupling commercially available 5-bromothiophene-3-carboxylic acid with 3-amino-N-cyclopropyl-4-methylbenzamide hydrochloride (prepared as described in WO 04/071440) using the method described in Example 128 to afford a tan solid. HPLC Ret time=3.02 min. LCMS [M+H]$^+$ 379.0.

Step B 5-(4-Chlorophenyl)-N-(5-(cyclopropylcarbamoyl)-2-methylphenyl)thiophene-3-carboxamide The title compound was prepared by coupling 5-bromo-N-(5-(cyclopropylcarbamoyl)-2-methylphenyl)thiophene-3-carboxamide a with commercially available 4-chlorophenylboronic acid using the method described in Step B of Example 136 to afford a white solid (Example 201). HPLC Ret time=3.67 min. LCMS [M+H]$^+$ 411.21.

Example 202

N-(5-(Cyclopropylcarbamoyl)-2-methylphenyl)-5-(pyridin-3-yl)thiophene-3-carboxamide

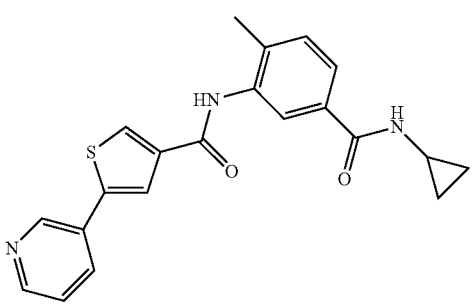 [SMILES: Cc1ccc(C(=O)NC2CC2)cc1NC(=O)c1csc(-c2cccnc2)c1]

The title compound was prepared by coupling 5-bromo-N-(5-(cyclopropylcarbamoyl)-2-methylphenyl)thiophene-3-carboxamide with commercially available 3-pyridylphenylboronic acid using the method described in Step B of Example 136 to afford a white solid (Example 202). HPLC Ret time=1.97 min. LCMS [M+H]$^+$ 378.2.

Example 203

4-(4-Chlorophenyl)-N-(5-(cyclopropylcarbamoyl)-2-methylphenyl)thiophene-2-carboxamide

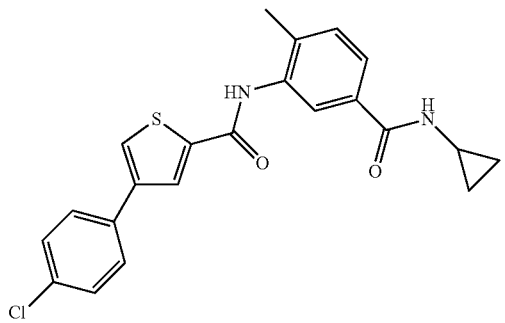 [SMILES: Cc1ccc(C(=O)NC2CC2)cc1NC(=O)c1cc(-c2ccc(Cl)cc2)cs1]

Step A

4-Bromo-N-(5-(cyclopropylcarbamoyl)-2-methylphenyl)thiophene-2-carboxamide

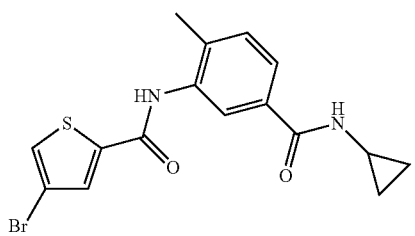

Compound a was prepared by coupling commercially available 3-bromothiophene-5-carboxylic acid with 3-amino-N-cyclopropyl-4-methylbenzamide hydrochloride (prepared as described in WO 04/071440) using the method described in Example 128 to afford a tan solid. HPLC Ret time=3.01 min. LCMS [M+H]$^+$ 379.0.

Step B 4-(4-Chlorophenyl)-N-(5-(cyclopropylcarbamoyl)-2-methylphenyl)thiophene-2-carboxamide The title compound was prepared by coupling 4-bromo-N-(5-(cyclopropylcarbamoyl)-2-methylphenyl)thiophene-2-carboxamide a with commercially available 4-chlorophenylboronic acid using the method described in Step B of Example 136 to afford a white solid (Example 203). HPLC Ret time=3.66 min. LCMS [M+H]$^+$ 411.21.

Example 204

N-(5-(Cyclopropylcarbamoyl)-2-methylphenyl)-4-(pyridin-3-yl)thiophene-2-carboxamide

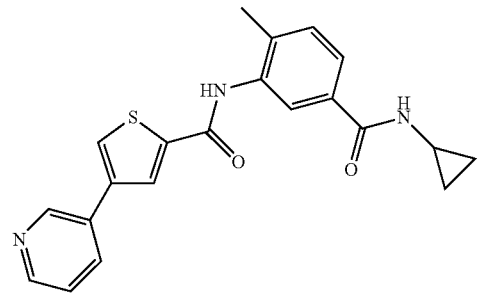 [SMILES: Cc1ccc(C(=O)NC2CC2)cc1NC(=O)c1cc(-c2cccnc2)cs1]

The title compound was prepared by coupling 4-bromo-N-(5-(cyclopropylcarbamoyl)-2-methylphenyl)thiophene-2-carboxamide with commercially available 3-pyridylphenylboronic acid using the method described in Step B of Example 136 to afford a white solid (Example 204). HPLC Ret time=1.91 min. LCMS [M+H]$^+$ 378.22.

Example 205

N-(5-(Cyclopropylcarbamoyl)-2-methylphenyl)-5-(4-(morpholine-4-carbonyl)phenyl)thiophene-2-carboxamide

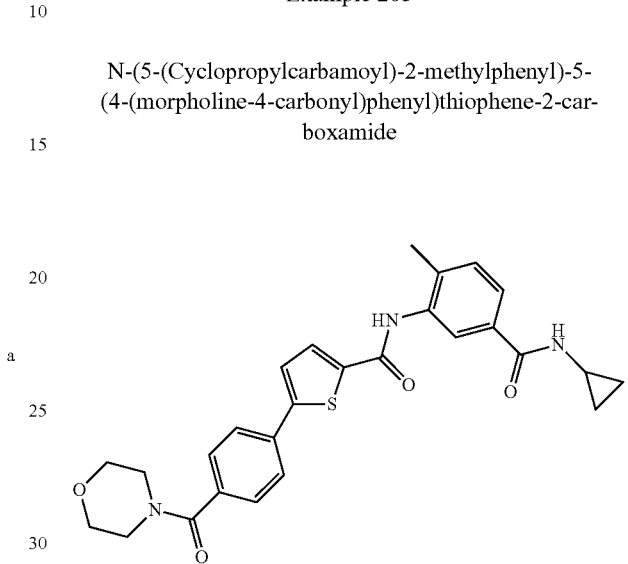

The title compound was prepared by reacting Example 147 with morpholine using the method described in Example 128 to afford a white solid (Example 205). HPLC Ret. Time=2.86 min, LCMS [M+H]$^+$ 490.29.

Example 206

N-(5-(Cyclopropylcarbamoyl)-2-methylphenyl)-5-(4-(4-methylpiperazine-1-carbonyl)phenyl)thiophene-2-carboxamide

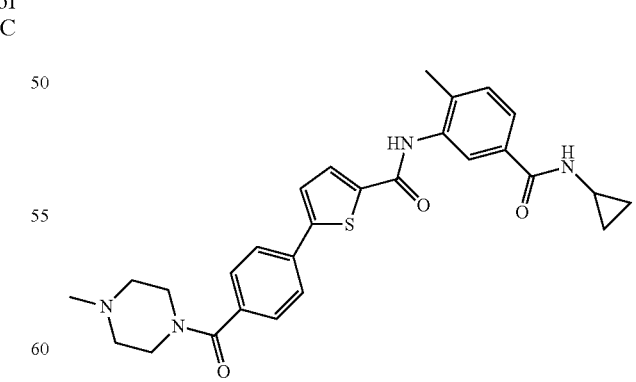

The title compound was prepared by reacting Example 147 with N-methylpiperizine using the method described in Example 128 to afford a white solid (Example 206). HPLC Ret. Time=2.09 min, LCMS [M+H]$^+$ 503.4.

Example 207 tent-Butyl 4-(4-(5-(5-(cyclopropylcarbamoyl)-2-methylphenylcarbamoyl)thiophen-2-yl)benzoyl)piperazine-1-carboxylate

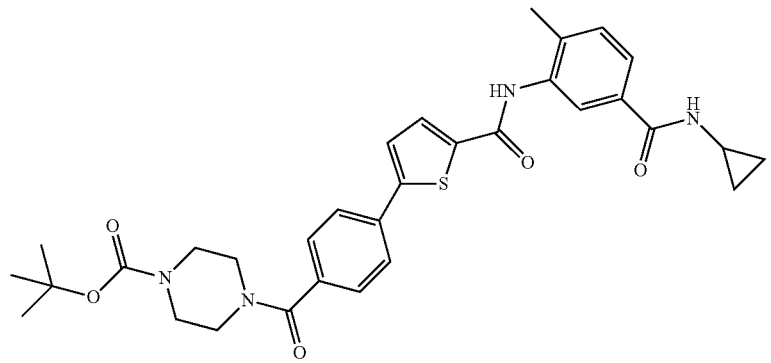 [SMILES: Cc1ccc(C(=O)NC2CC2)cc1NC(=O)c1ccc(-c2ccc(C(=O)N3CCN(C(=O)OC(C)(C)C)CC3)cc2)s1]

The title compound was prepared by reacting Example 147 with tert-butyl piperazine-1-carboxylate using the method described in Example 128 to afford a white solid (Example 207). HPLC Ret. Time=3.42 min, LCMS [M+H]$^+$ 589.45.

Example 208

3-Amino-5-(4-chlorophenyl)-N-(5-(cyclopropylcarbamoyl)-2-methylphenyl)thiophene-2-carboxamide

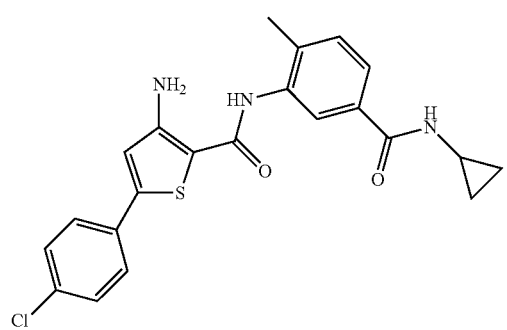 [SMILES: Cc1ccc(C(=O)NC2CC2)cc1NC(=O)c1sc(-c2ccc(Cl)cc2)cc1N]

Step A

Methyl 3-(bis(tert-butoxycarbonyl)amino)-5-(4-chlorophenyl)thiophene-2-carboxylate

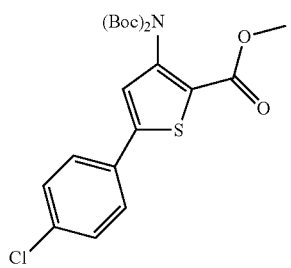

a

To a solution of methyl 3-amino-5-(4-chlorophenyl)thiophene-2-carboxylate (0.50 g, 1.87 mmol) in THF (8 mL) at rt was added a 1.0 M solution of LiHMDS in THF (4.1 mL, 4.1 mmol) and the resulting mixture was stirred at rt for 10 min then (Boc)$_2$O (1.02 g, 4.67 mmol) was added. After stirring at rt for 15 min, the mixture was diluted with EtOAc (200 mL) and was washed with water (2×20 mL), brine, then dried over anhyd Na$_2$SO$_4$, filtered, and concentrated under vacuum to afford ~1.02 g of an orange oil as the crude product. This material was purified by flash column chromatography using EtOAc/Hexanes mixtures as the eluent to afford 600 mg (68%) of a tan solid as the compound a. HPLC Ret time=4.83 min.

Step B 3-(Bis(tert-butoxycarbonyl)amino)-5-(4-chlorophenyl)thiophene-2-carboxylic acid

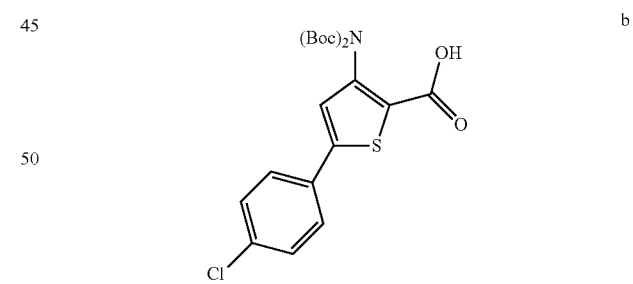

b

To a solution of methyl 3-(bis(tert-butoxycarbonyl)amino)-5-(4-chlorophenyl)thiophene-2-carboxylate a (0.135 g, 0.29 mmol) in 1:1 THF/MeOH (2 mL) at rt was added a 3 N aq NaOH (1 mL) and the resulting mixture was warmed to 65° C. for 30 min then cooled to rt and concentrated to remove the volatile solvents. The remaining aqueous portion was cooled in an ice bath and 1 N aq HCl was added until pH~2 was reached. The slurry was stirred for 1 h then collected the resulting solid by vacuum filtration, rinsed with water and dried under vacuum to afford 86 mg (66%) of an off-white solid as compound b. HPLC Ret time=4.32 min.

Step C
Intermediate c

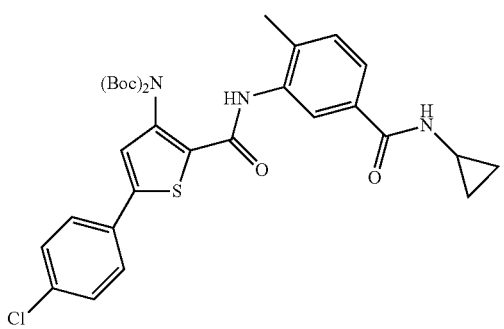

Intermediate c was prepared by coupling 3-(bis(tert-butoxycarbonyl)amino)-5-(4-chlorophenyl)thiophene-2-carboxylic acid with 3-amino-N-cyclopropyl-4-methylbenzamide hydrochloride (prepared as described in WO 04/071440) using the method described in Example 128 to afford a cream colored solid. HPLC Ret time=4.35 min.

Step D

3-Amino-5-(4-chlorophenyl)-N-(5-(cyclopropylcarbamoyl)-2-methylphenyl)thiophene-2-carboxamide A solution of Intermediate c (8.5 mg) was stirred in a solution of 4 N HCl in dioxane (0.5 mL) at rt for 6 h. The mixture was diluted with MeOH and was purified by reverse-phase preparative HPLC to afford the TFA salt of the title compound (Example 208) as a pale yellow solid. HPLC Ret time=3.59 min. LCMS [M+H]$^+$ 426.20.

Example 209

3-Amino-4-(4-chlorophenyl)-N-(5-(cyclopropylcarbamoyl)-2-methylphenyl)thiophene-2-carboxamide

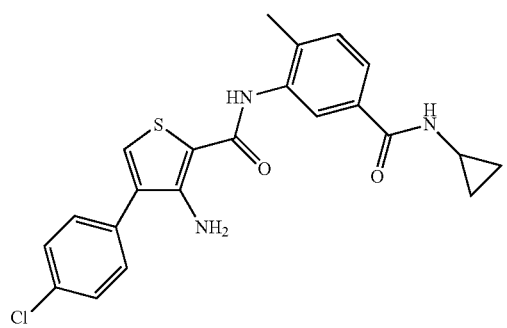 [SMILES: Cc1ccc(C(=O)NC2CC2)cc1NC(=O)c1scc(-c2ccc(Cl)cc2)c1N]

Step A

N-Cyclopropyl-3-(2-mercaptoacetamido)-4-methylbenzamide

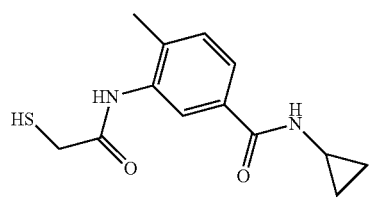

A solution of mercaptoacetic acid (1.65 mL, 24.2 mmol) and 5.0 g (22 mmol) of 3-amino-N-cyclopropyl-4-methylbenzamide hydrochloride (prepared as described in WO 04/071440) in toluene (40 mL) was refluxed for 16 h. At this time, an additional 0.8 mL of mercaptoacetic acid was added and the mixture was continued at reflux for an additional 2 days. After cooling to rt, the solid was collected by vacuum filtration and was rinsed with EtOAc (2×50 mL). The resulting solid was then slurried in water (50 mL) and the solid was recollected by vacuum filtration and rinsed with add'n water. The resulting solid was air dried in the funnel then under vacuum overnight to afford 1.86 g (32%) of a white solid as compound a. HPLC Ret time=1.83 min. LCMS [M+H]$^+$ 265.37.

Step B

3-Amino-4-(4-chlorophenyl)-N-(5-(cyclopropylcarbamoyl)-2-methylphenyl)thiophene-2-carboxamide To MeOH (4 mL) at rt was added a 25% (w/w) solution of NaOMe in MeOH followed by addition of N-cyclopropyl-3-(2-mercaptoacetamido)-4-methylbenzamide a (200 mg, 10.8 mmol). After stirring at rt for 15 min, 200 mg (10.6 mmol) of 2-(4-chlorophenyl)-2-cyanovinyl benzenesulfonate (prepared as described in *J. Med. Chem.*, 6(47):1448 (2004)) was added and the resulting solution was warmed to 60° C. for 2 h then allowed to cool to rt and stir for an additional 15 h. The mixture was concentrated under vacuum to remove the MeOH then water (20 mL) was added and the solution was extracted with EtOAc (200 mL). The organic extract was washed with water, brine, then dried over anhyd Na$_2$SO$_4$, filtered, and concentrated under vacuum to afford 300 mg of an orange solid as the crude product. This material was purified by reverse-phase preparative HPLC to afford 50 mg of a light yellow solid as the title compound (Example 209). HPLC Ret time=3.57 min. LCMS [M+H]$^+$ 426.17.

Example 210

N-(5-(Cyclopropylcarbamoyl)-2-methylphenyl)-5-(3-(trifluoromethyl)pyridin-2-yl)thiophene-2-carboxamide

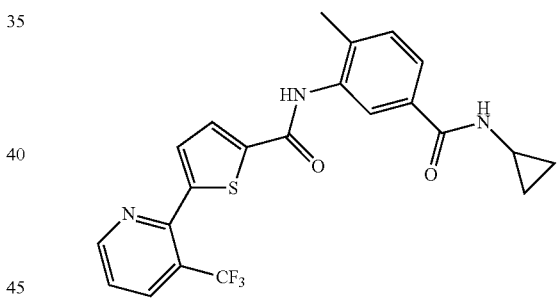

Step A 5-(5-(Cyclopropylcarbamoyl)-2-methylphenylcarbamoyl)thiophen-2-ylboronic acid

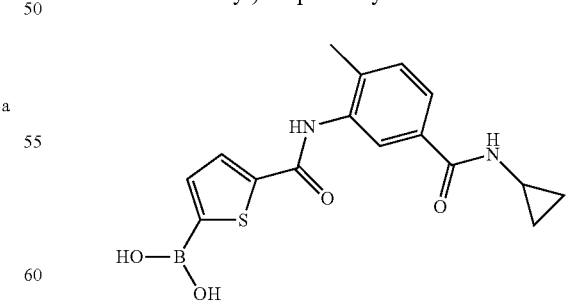

A solution of 1.0 g (2.64 mmol) of 5-bromo-N-(5-(cyclopropylcarbamoyl)-2-methylphenyl)thiophene-2-carboxamide (Example 136, Step B), bis(pinacolato)diborane (1.0 g, 3.95 mmol) and KOAc (1.30 g, 13.2 mmol) in DMF (15 mL) was purged with argon and Pd(dppf)$_2$Cl$_2$/CH$_2$Cl$_2$ complex (65 mg, 0.08 mmol) was added followed by heating at 90° C.

for 16 h. After cooling to rt, the mixture was partitioned between EtOAc (250 mL) and water (50 mL) and the layers were separated. The organic portion was washed with additional water, then brine, then dried over anhyd $Na_2SO_4$, filtered, and concentrated under vacuum to afford 1.62 g of a brown semi-solid as the crude product mixture. This material was triturated with EtOAc and filtered to afford 626 mg of the compound a containing ~10% of the boronate ester. This material was used as is without any further purification. HPLC Ret time=2.36 min. LCMS [M+H]+ 345.2.
Step B N-(5-(Cyclopropylcarbamoyl)-2-methylphenyl)-5-(3-(trifluoromethyl)pyridin-2-yl)thiophene-2-carboxamide The title compound b was prepared by coupling 5-(5-(cyclopropylcarbamoyl)-2-methylphenylcarbamoyl)thiophen-2-ylboronic acid a with commercially available 2-chloro-3-trifluoromethylpyridine using the method described in Step B of Example 136 to afford a light yellow solid after purification by reverse phase preparative HPLC (Example 210). HPLC Ret time=3.46 min. LCMS [M+H]+ 446.26.

Example 211

5-(5-(5-(Cyclopropylcarbamoyl)-2-methylphenylcarbamoyl)thiophen-2-yl)nicotinamide

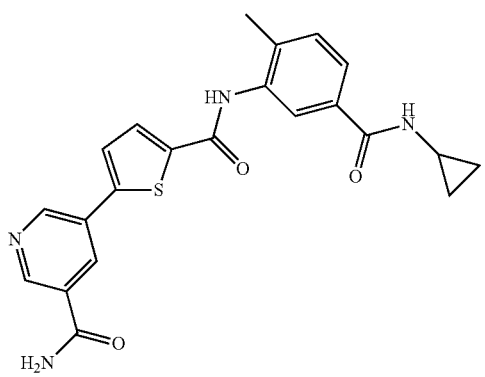 [SMILES: Cc1ccc(C(=O)NC2CC2)cc1NC(=O)c1ccc(-c2cncc(C(N)=O)c2)s1]

The title compound was prepared by coupling 5-(5-(cyclopropylcarbamoyl)-2-methylphenylcarbamoyl)thiophen-2-ylboronic acid (Example 210, Step A) with commercially available 3-chloro-5-cyanopyridine using the method described in Step B of Example 136 to afford a white solid after purification by reverse phase preparative HPLC (Example 211). HPLC Ret time=2.56 min. LCMS [M+H]+ 421.26.

Example 212

N-(5-(Cyclopropylcarbamoyl)-2-methylphenyl)-5-(4-methylpyridin-3-yl)thiophene-2-carboxamide

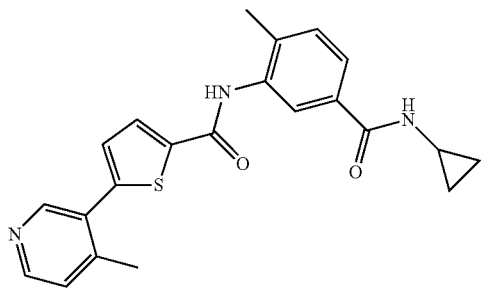 [SMILES: Cc1ccc(C(=O)NC2CC2)cc1NC(=O)c1ccc(-c2cnccc2C)s1]

The title compound was prepared by coupling 5-(5-(cyclopropylcarbamoyl)-2-methylphenylcarbamoyl)thiophen-2-ylboronic acid (Example 210, Step A) with commercially available 3-bromo-4-methylpyridine using the method described in Step B of Example 136 to afford a white solid after purification by reverse phase preparative HPLC (Example 212). HPLC Ret time=1.99 min. LCMS [M+H]+ 392.3.

Example 213

5-(5-Cyano-2-methylphenyl)-N-(5-(cyclopropylcarbamoyl)-2-methylphenyl)thiophene-2-carboxamide

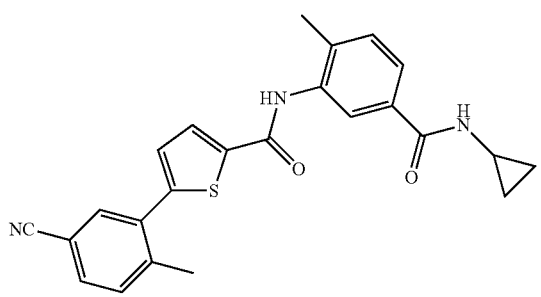

The title compound was prepared by coupling 5-(5-(cyclopropylcarbamoyl)-2-methylphenylcarbamoyl)thiophen-2-ylboronic acid (Example 210, Step A) with commercially available 2-bromo-4-cyanotoluene using the method described in Step B of Example 136 to afford a white solid after purification by reverse phase preparative HPLC (Example 213). HPLC Ret time=3.36 min. LCMS [M+H]+ 416.29.

Examples 214 and 215

Example 214

5-(5-Cyano-2-methylphenyl)-N-(5-(cyclopropylcarbamoyl)-2-methylphenyl)thiophene-2-carboxamide
and Example 215

5-(5-Carbamoyl-2-methylphenyl)-N-(5-(cyclopropylcarbamoyl)-2-methylphenyl)thiophene-2-carboxamide

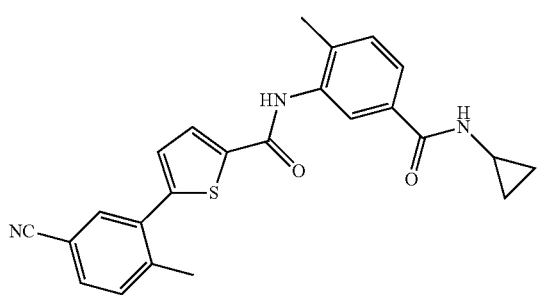 [SMILES: Cc1ccc(C(=O)NC2CC2)cc1NC(=O)c1ccc(-c2cc(C#N)ccc2C)s1]

major product

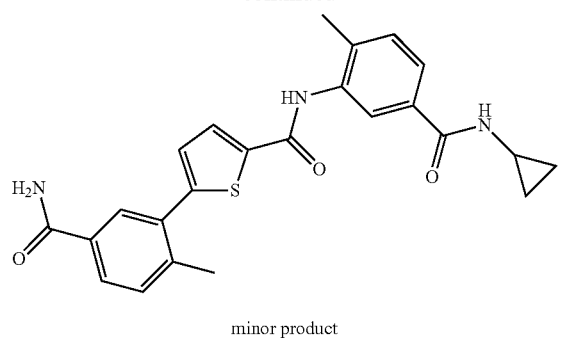

minor product

The title compounds were prepared by coupling 5-(5-(cyclopropylcarbamoyl)-2-methylphenylcarbamoyl)thiophen-2-ylboronic acid (Example 210, Step A) with commercially available 2-bromo-4-cyanotoluene using the method described in Step B of Example 136 to afford the title compounds as white solids after purification by reverse phase preparative HPLC. Major product: HPLC Ret time=3.36 min. LCMS [M+H]+ 416.29. Minor product: HPLC Ret time=2.90 min. LCMS [M+H]+ 434.37.

Examples 216 and 217

Example 216

5-(3-Cyano-5-fluorophenyl)-N-(5-(cyclopropylcarbamoyl)-2-methylphenyl)thiophene-2-carboxamide and Example 217

5-(3-Carbamoyl-5-fluorophenyl)-N-(5-(cyclopropylcarbamoyl)-2-methylphenyl)thiophene-2-carboxamide

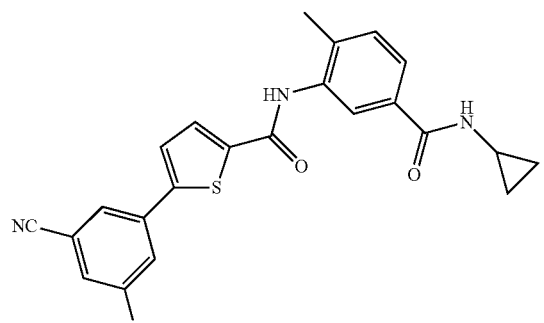

major product

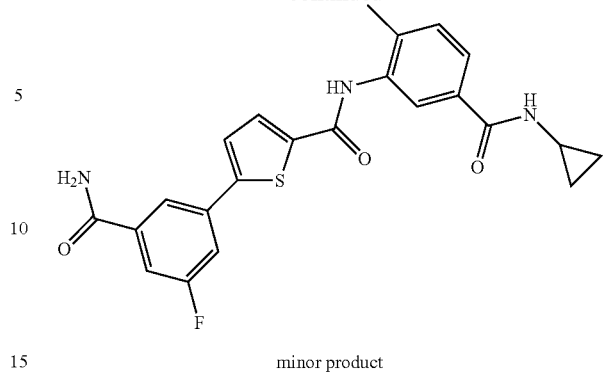

minor product

The title compounds were prepared by coupling 5-(5-(cyclopropylcarbamoyl)-2-methylphenylcarbamoyl)thiophen-2-ylboronic acid (Example 210, Step A) with commercially available 3-bromo-5-fluorobenzonitrile using the method described in Step B of Example 136 to afford the title compounds as white solids after purification by reverse phase preparative HPLC. Major product: HPLC Ret time=3.34 min. LCMS [M+H]+ 420.26. Minor product: HPLC Ret time=3.00 min. LCMS [M+H]+ 438.24.

Example 218

Ethyl 6-(5-(cyclopropylcarbamoyl)-2-methylphenylcarbamoyl)-1H-indole-1-carboxylate

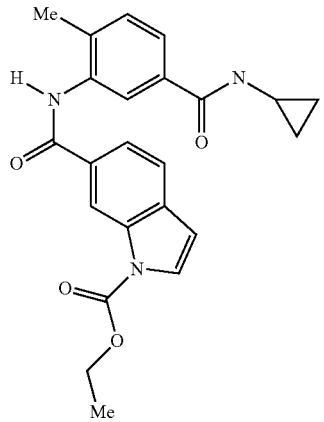 [SMILES: CCOC(=O)n1ccc2ccc(C(=O)Nc3cc(C(=O)NC4CC4)ccc3C)cc21]

To a solution of 3-amino-N-cyclopropyl-4-methylbenzamide (0.025 g, 0.11 mmol) in anhydrous DMF (0.5 mL), are sequentially added 1-(ethoxycarbonyl)-1H-indole-6-carboxylic acid (0.026 g, 0.11 mmol, prepared according to a similar procedure outlined for step A, Example 128 in WO 2002/014308) triethylamine (61 µL, 0.44 mmol) and BOP (0.098 g, 0.22 mmol) at room temperature. The reaction mixture was stirred at room temperature for 18 h, diluted with MeOH (0.5 mL) and subjected to reverse phase preparative HPLC (YMC S5 20×100 mm, 10 min. run, solvent A: 10% MeOH: 90% H$_2$O: 0.1% TFA, solvent B: 90% MeOH, 10% H$_2$O, 0.1% TFA). The desired fractions were collected, and concentrated using speedVac® Plus (SC250DDA) to yield the title compound (Example 218, 0.010 g). HPLC Ret. time (YMC S5 Combiscreen ODS; 4.6×50 mm (4 min. gradient); Solvent A=10% MeOH, 90% H$_2$O, 0.2% H$_3$PO$_4$; solvent B=90% MeOH, 10% H$_2$O, 0.2% H$_3$PO$_4$): 3.18 min. LCMS [M+H]+ 406.3.

Examples 219 to 222

Compounds listed in Table 10 were prepared using the method described for Example 218.

TABLE 10

| Example No. | Structure | Name | HPLC ret. Time, min. (column conditions)* | LCMS [M + H]+ |
|---|---|---|---|---|
| 219 | 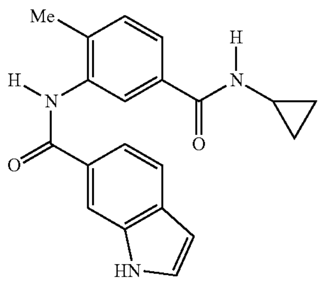 [SMILES: Cc1ccc(C(=O)NC2CC2)cc1NC(=O)c1ccc2cc[nH]c2c1] | N-(5-(cyclopropylcarbamoyl)-2-methylphenyl)-1H-indole-6-carboxamide | 2.64 | 334 |
| 220 | 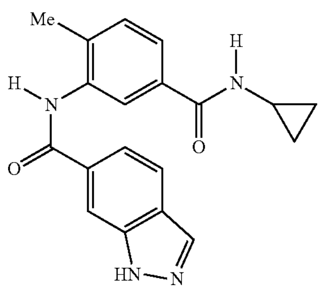 [SMILES: Cc1ccc(C(=O)NC2CC2)cc1NC(=O)c1ccc2cn[nH]c2c1] | N-(5-(cyclopropylcarbamoyl)-2-methylphenyl)-1H-indazole-6-carboxamide | 2.85 | 335 |
| 221 | 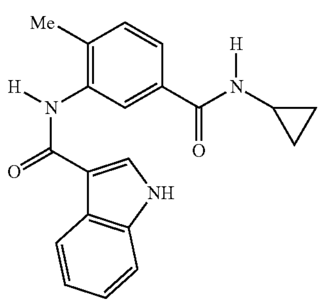 [SMILES: Cc1ccc(C(=O)NC2CC2)cc1NC(=O)c1c[nH]c2ccccc12] | N-(5-(cyclopropylcarbamoyl)-2-methylphenyl)-1H-indole-3-carboxamide | 2.60 | 334 |
| 222 | 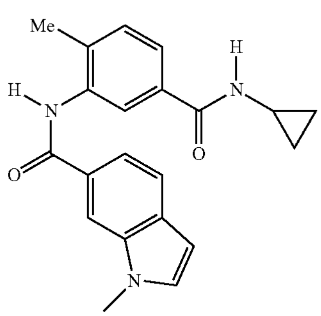 [SMILES: Cc1ccc(C(=O)NC2CC2)cc1NC(=O)c1ccc2ccn(C)c2c1] | N-(5-(cyclopropylcarbamoyl)-2-methylphenyl)-1-methyl-1H-indole-6-carboxamide | 2.74 | 347 |

*YMC S5 Combiscreen ODS ; 4.6 × 50 mm (4 min. gradient); Solvent A = 10% MeOH, 90% H$_2$O, 0.2% H$_3$PO$_4$; solvent B = 90% MeOH, 10% H$_2$O, 0.2% H$_3$PO$_4$).

Example 223

3-Cyano-N-(5-(cyclopropylcarbamoyl)-2-methylphenyl)-1-methyl-1H-indole-6-carboxamide

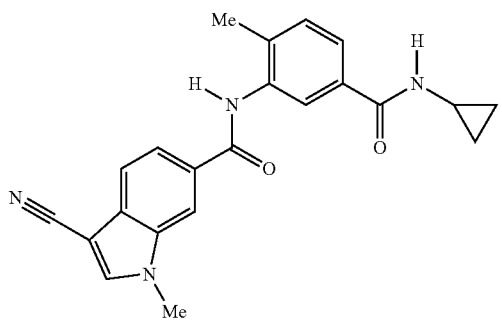 [SMILES: Cc1ccc(C(=O)NC2CC2)cc1NC(=O)c1ccc2c(C#N)cn(C)c2c1]

To N-(5-(cyclopropylcarbamoyl)-2-methylphenyl)-1-methyl-1H-indole-6-carboxamide (0.045 g, 0.129 mmol, example 97, table 5) in anhydrous acetonitrile (2 mL) was added chlorosulfonyl isocyanate (11 µL, 0.129 mmol) at room temperature. The reaction mixture was stirred at room temperature for 30 min. and DMF (11 µL, 0.141 mmol) is added. After another 30 min. at room temperature, the reaction mixture was quenched with methanol (2 mL), concentrated under reduced pressure and subjected to reverse phase preparative HPLC (YMC S5 20×100 mm, 10 min. run, solvent A: 10% MeOH: 90% H$_2$O: 0.1% TFA, solvent B: 90% MeOH, 10% H$_2$O, 0.1% TFA). The desired fractions were collected, and concentrated using speedVac® Plus (SC250DDA) to yield the title compound (Example 223, 0.005 g). HPLC retention time (YMC S5 Combiscreen ODS; 4.6×50 mm (4 min. gradient); Solvent A=10% MeOH, 90% H$_2$O, 0.2% H$_3$PO$_4$; solvent B=90% MeOH, 10% H$_2$O, 0.2% H$_3$PO$_4$): 2.6 min. LCMS [M+H]$^+$ 373.2.

Example 224

N-(5-(Cyclopropylcarbamoyl)-2-methylphenyl)-1-isopropyl-1H-indole-6-carboxamide

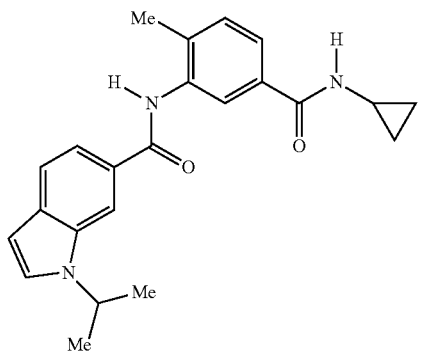 [SMILES: Cc1ccc(C(=O)NC2CC2)cc1NC(=O)c1ccc2ccn(C(C)C)c2c1]

To N-(5-(cyclopropylcarbamoyl)-2-methylphenyl)-1H-indole-6-carboxamide (0.05 g, 0.15 mmol, example 94, table 5) in DMF (0.5 mL) was added sodium hydride (60% dispersion, 0.030 g, 0.75 mmol) over a period of 3 min, at room temperature. After stirring at room temperature for 5 min. isopropyl bromide (21 µL, 0.225 mmol) is added and the contents stirred at room temperature for 1 h. The reaction mixture was quenched with 100 µL of methanol and subjected to reverse phase preparative HPLC (YMC S5 20×100 mm, 10 min. run, solvent A: 10% MeOH: 90% H$_2$O: 0.1% TFA, solvent B: 90% MeOH, 10% H$_2$O, 0.1% TFA). The desired fractions were collected, and concentrated using speedVac® Plus (SC250DDA) to yield the title compound (Example 224, 0.015 g). HPLC retention time (YMC S5 Combiscreen ODS; 4.6×50 mm (4 min. gradient); Solvent A=10% MeOH, 90% H$_2$O, 0.2% H$_3$PO$_4$; solvent B=90% MeOH, 10% H$_2$O, 0.2% H$_3$PO$_4$): 3.1 min. LCMS [M+H]$^+$ 376.

Example 225

N-(5-(Cyclopropylcarbamoyl)-2-methylphenyl)-1-(2-morpholinoethyl)-1H-indole-6-carboxamide

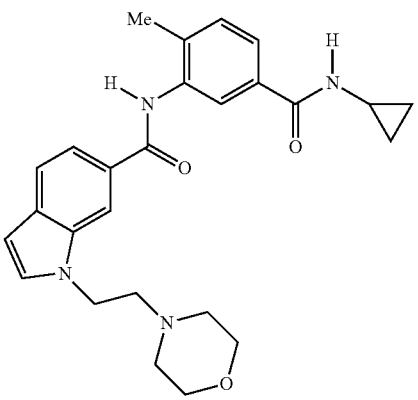 [SMILES: Cc1ccc(C(=O)NC2CC2)cc1NC(=O)c1ccc2ccn(CCN3CCOCC3)c2c1]

Step A 1-(2-Morpholinoethyl)-1H-indole-6-carboxylic acid

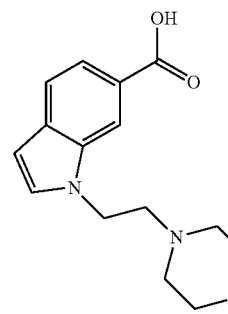

a

To methyl 1H-indole-6-carboxylate (0.5 g, 2.85 mmol) and 4-(2-chloroethyl)morpholine (0.585 g, 3.13 mmol) in anhydrous DMF (5 mL) was added sodium hydride (60% dispersion, 0.342 g, 8.55 mmol) at 0° C. The reaction mixture was stirred at room temperature for 3 min. and heated at 50° C. for 1.5 h. The reaction mixture was cooled to room temperature and quenched by the slow addition of water (2 mL). The residue was diluted with water (2 mL), methanol (1 mL) and subjected to reverse phase preparative HPLC (YMC S5 20×100 mm, 10 min. run, solvent A: 10% MeOH: 90% H$_2$O: 0.1% TFA, solvent B: 90% MeOH, 10% H$_2$O, 0.1% TFA). The desired fractions were collected, and concentrated using speedVac® Plus (SC250DDA) to yield compound a (0.075 g—TFA salt). HPLC retention time (Phenomex Luna 5u C18; 4.6×30 mm (2 min. gradient); Solvent A=10% MeOH, 90%

H₂O, 0.1% TFA; solvent B=90% MeOH, 10% H₂O, 0.1% TFA): 0.87 min. LCMS [M+H]⁺ 275.

Step B

N-(5-(Cyclopropylcarbamoyl)-2-methylphenyl)-1-(2-morpholinoethyl)-1H-indole-6-carboxamide The title compound was prepared from 1-(2-morpholinoethyl)-1H-indole-6-carboxylic acid a (0.07 g, 0.18 mmol) as described in Example 218 to afford Example 225 (0.007 g) as a TFA salt. HPLC retention time (YMC S5 Combiscreen ODS; 4.6×50 mm (4 min. gradient); Solvent A=10% MeOH, 90% H₂O, 0.2% H₃PO₄; solvent B=90% MeOH, 10% H₂O, 0.2% H₃PO₄): 1.89 min. LCMS [M+H]⁺ 447.14.

Test Data

The following data describes activity for the compounds listed. The data was obtained using the assays described above. The ratio of beta/alpha is also listed to show the selectivity with the higher numbers indicating greater alpha selectivity.

TABLE 11

| Example No. | p38 alpha IC50 (nM) | p38 beta IC50 (nM) | beta/alpha (alpha selectivity) |
|---|---|---|---|
| 222 | 0.035 | 21.9 | 625 |
| 221 | 0.005 | 2.7 | 540 |
| 225 | 0.087 | 39 | 448 |
| 224 | 0.034 | 14.9 | 438 |
| 210 | 0.012 | 5.2 | 433 |
| 223 | 0.03 | 12.7 | 423 |
| 204 | 0.039 | 14.8 | 379 |
| 160 | 0.012 | 2.8 | 233 |
| 169 | 0.007 | 1.8 | 257 |
| 153 | 0.014 | 3.2 | 228 |
| 196 | 0.082 | 18.5 | 225 |
| 181 | 0.005 | 1.2 | 240 |
| 159 | 0.016 | 3.2 | 200 |
| 146 | 0.062 | 15.4 | 248 |
| 137 | 0.002 | 0.27 | 135 |
| 151 | 0.005 | 0.83 | 166 |
| 130 | 0.041 | 6.8 | 166 |
| 148 | 0.003 | 0.48 | 160 |
| 185 | 0.008 | 1.3 | 162 |
| 149 | 0.013 | 1.8 | 138 |
| 182 | 0.008 | 0.942 | 118 |

What is claimed is:

1. A compound of Formula I

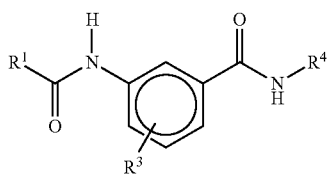

and enantiomers, diastereomers and pharmaceutically-acceptable salts thereof, wherein:

R¹ is selected from the group consisting of substituted cycloalkyls, substituted heterocyclos selected from piperidine and piperazine, and substituted heteroaryls selected from pyrrole, furan, imidazole, isothiazole, triazole, dihydropyrrolopyrrolone, indole, pyrrolotriazine, and thiazolopyrimidinone;

R³ is selected from the group consisting of hydrogen, C₁-C₄ alkyl and halogen; and R⁴ is selected from the group consisting of hydrogen, optionally substituted carboxyls, optionally substituted alkyls, optionally substituted alkoxys, optionally substituted cycloalkyls, optionally substituted aryls, optionally substituted heterocyclos and optionally substituted heteroaryls;

with the proviso that:

R⁴ is not optionally substituted pyrazolyl.

2. The compound according to claim 1 wherein R¹ is selected from the group consisting of substituted cyclopropyl and substituted heterocyclos selected from piperidine and piperazine.

3. The compound according to claim 1 wherein R¹ is selected from the group consisting of substituted heteroaryls selected from pyrrole, furan, imidazole, isothiazole, triazole, dihydropyrrolopyrrolone, indole, pyrrolotriazine, and thiazolopyrimidinone.

4. The compound according to claim 1 wherein R¹ is selected from the group consisting of substituted heteroaryls selected from pyrrole, furan, imidazole, isothiazole, triazole, dihydropyrrolopyrrolone, pyrrolotriazine, and thiazolopyrimidinone.

5. The compound according to claim 1 wherein R³ is H, Cl, F or CH₃.

6. The compound according to claim 5 wherein R³ is hydrogen or methyl.

7. The compound according to claim 1 wherein R⁴ is selected from the group consisting of C₁-C₅ alkyls, C₃-C₆ cycloalkyls, wherein the alkyls and cycloalkyls are optionally substituted with 1-4 members selected from the group consisting of C₁-C₅ alkyls and C₁-C₅ alkoxy groups.

8. The compound according to claim 7 wherein R⁴ is cyclopropyl.

9. The compound according to claim 1 wherein the substituted heteroaryls is indole.

10. The compound according to claim 1 which is at least 50 fold selective for p38α versus p38β.

11. A pharmaceutical composition comprising at least one compound according to claim 1 and a pharmaceutically-acceptable carrier or diluent.

12. The compound according to claim 2 selected from:

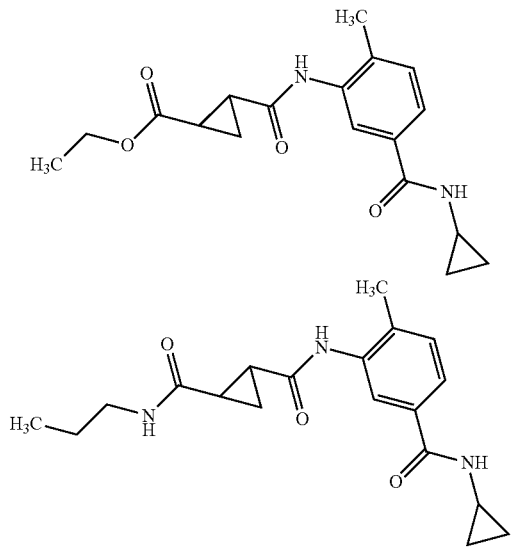

143
-continued
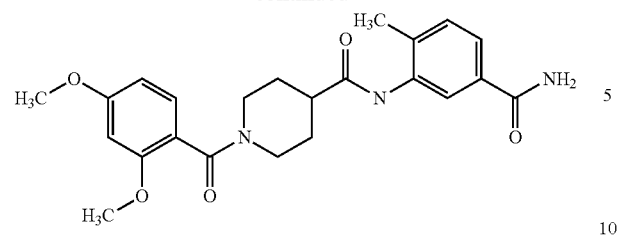
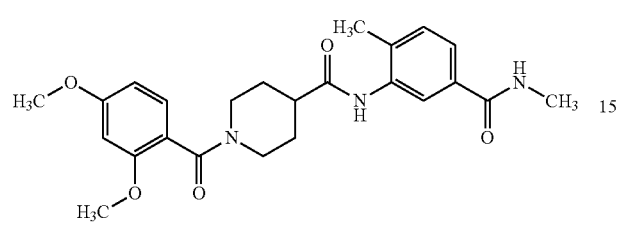
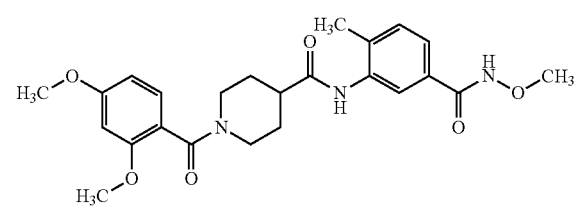
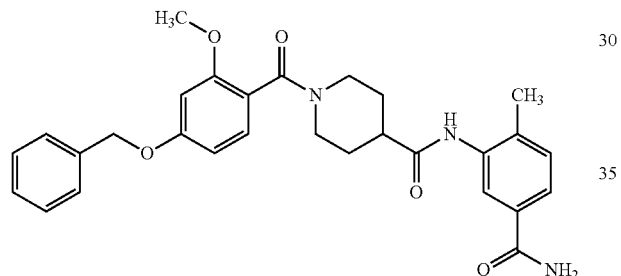
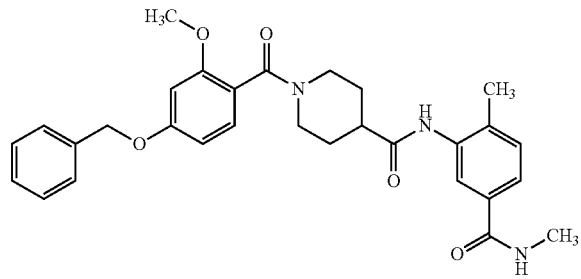
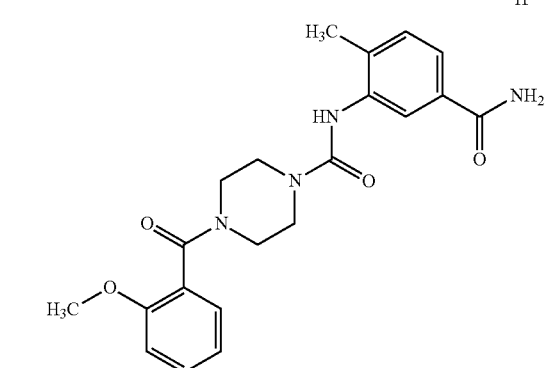
144
-continued
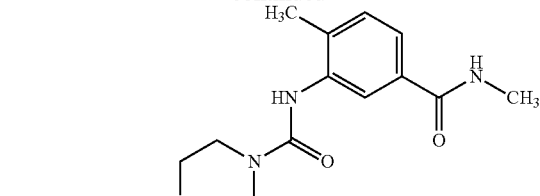
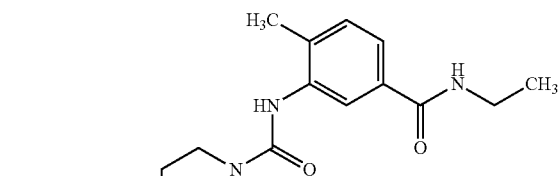
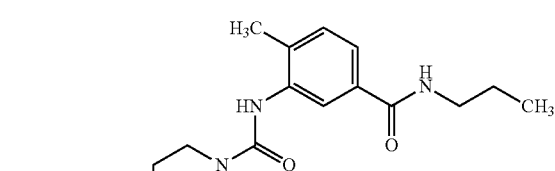

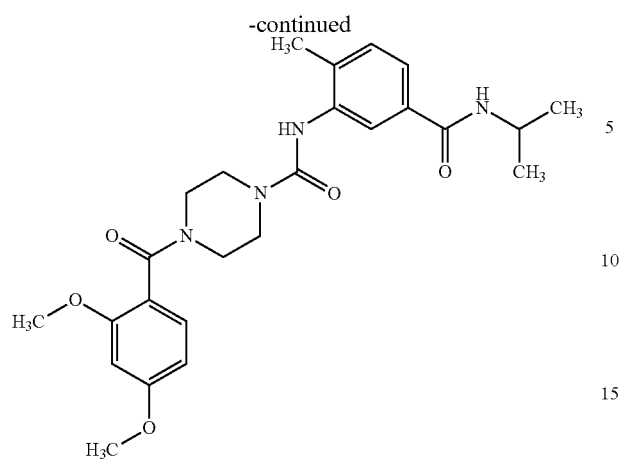
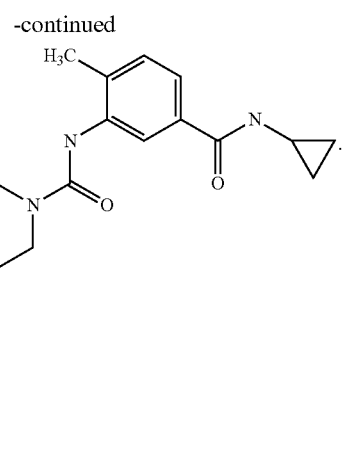
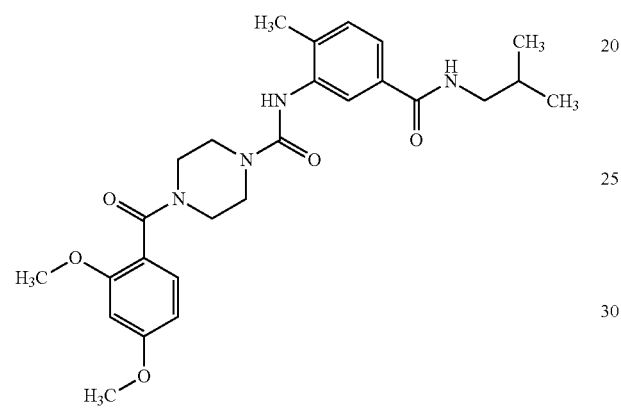
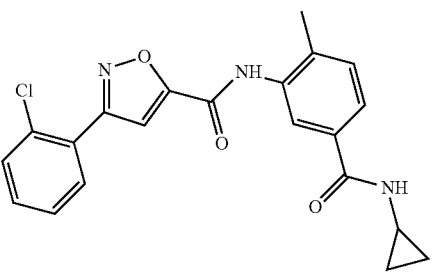
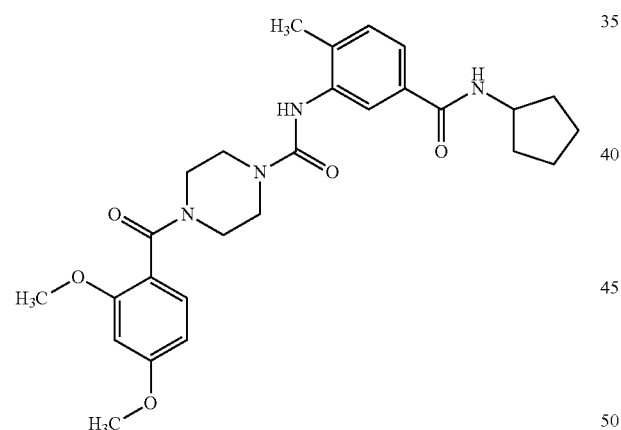
13. The compound according to claim 3 selected from:
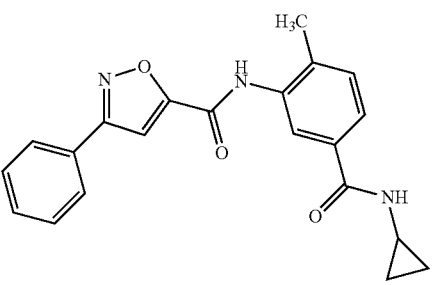
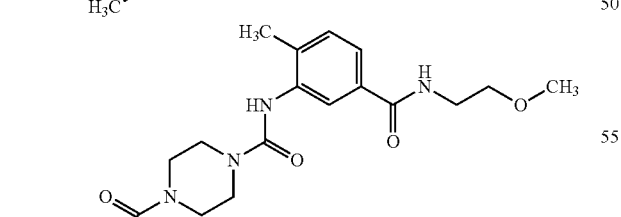
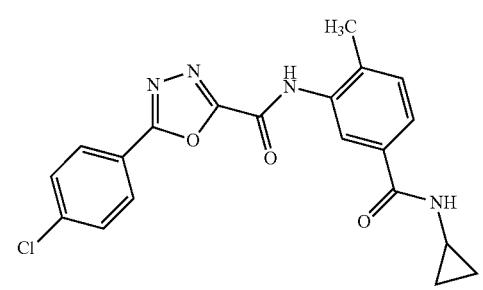
or
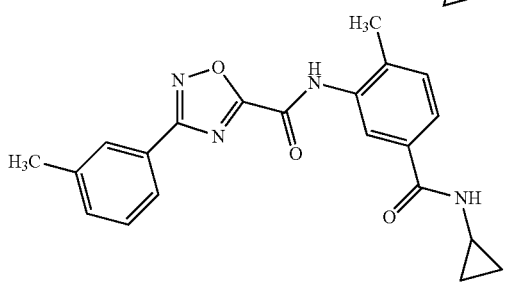

-continued
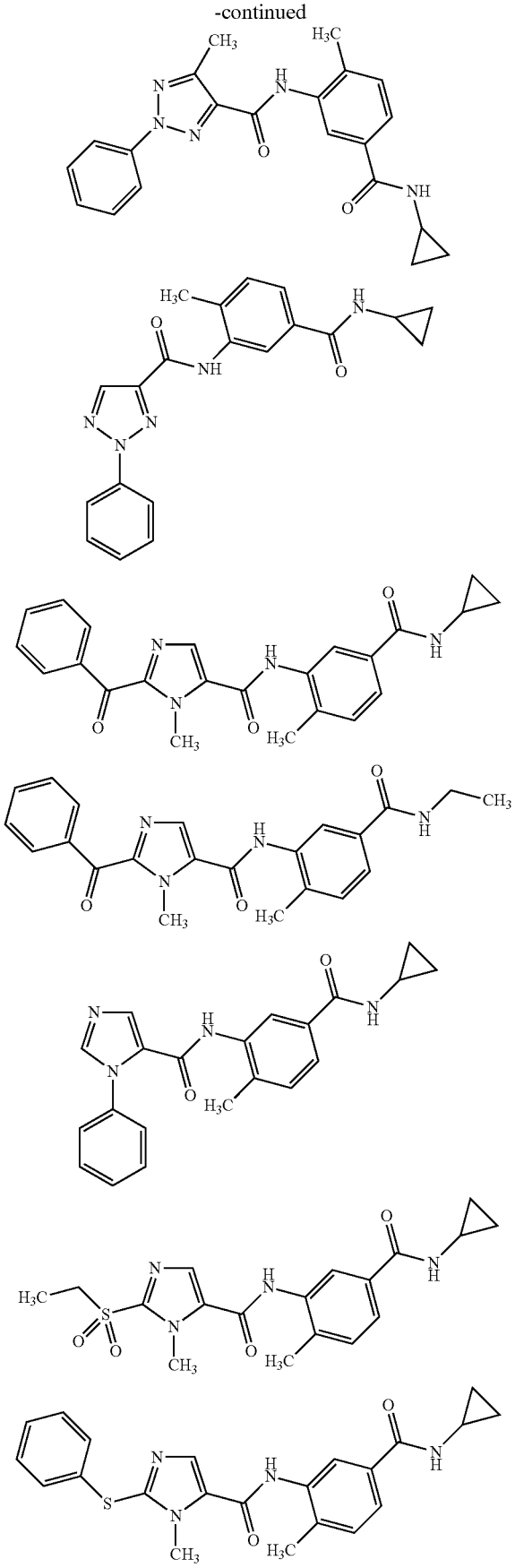
-continued
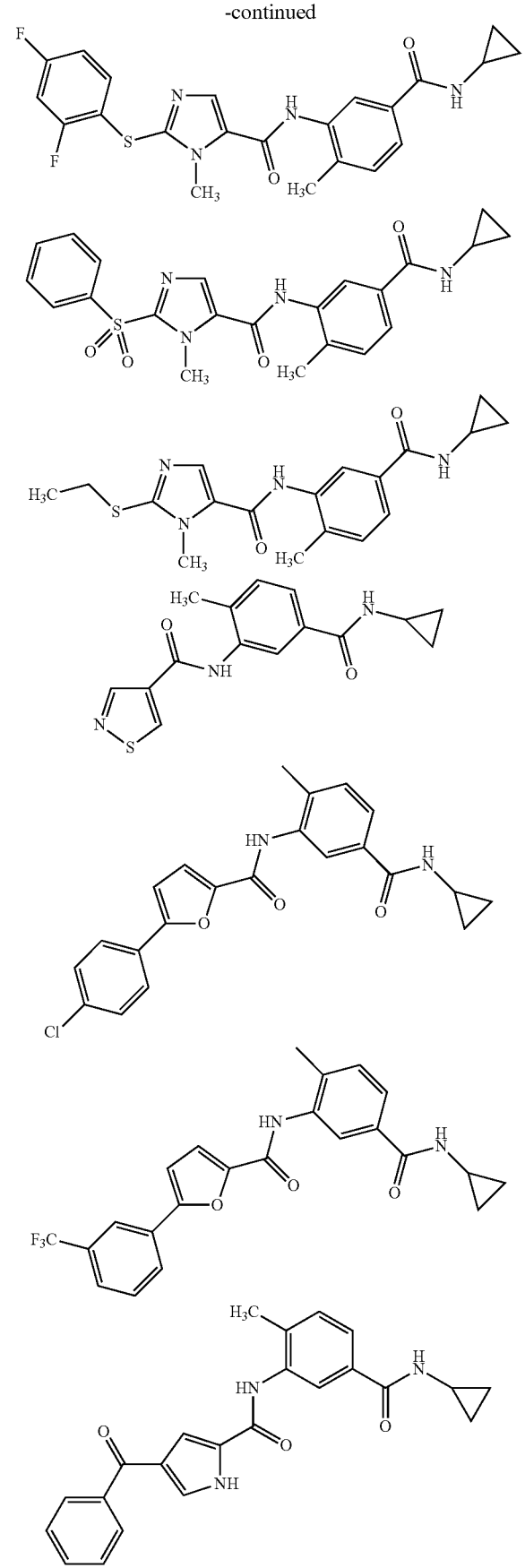

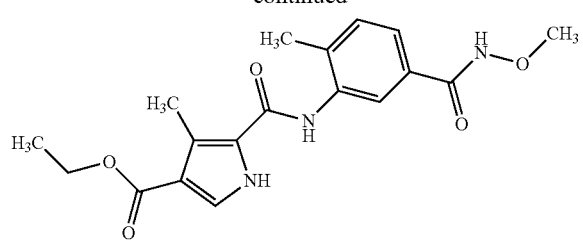
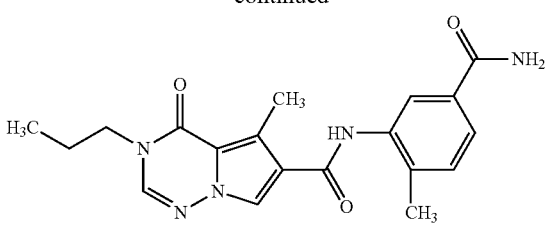
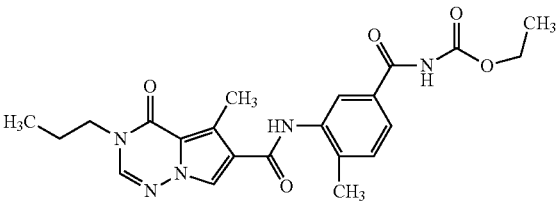
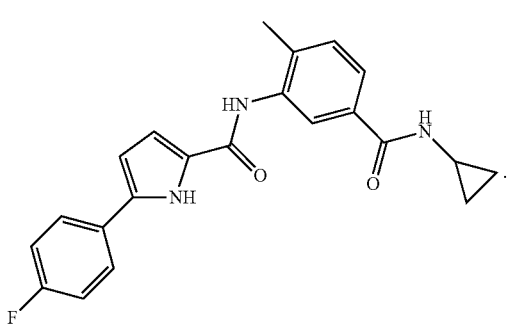
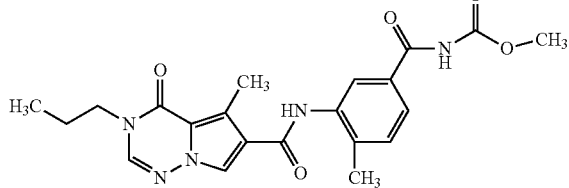
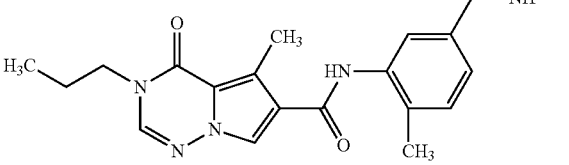
14. The compound according to claim 3 selected from:
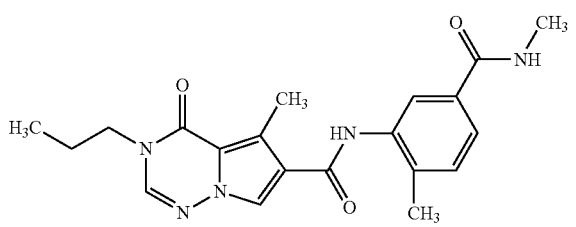
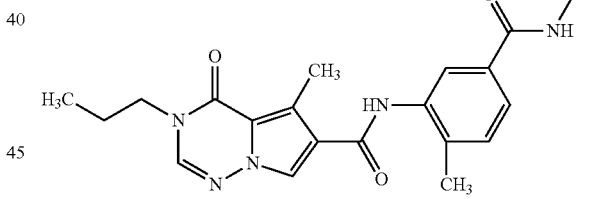
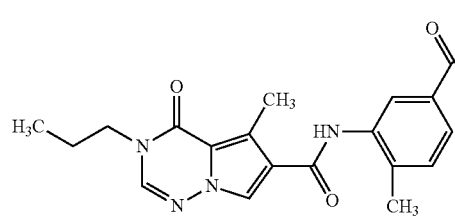
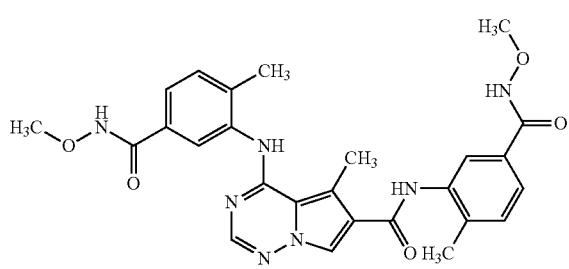
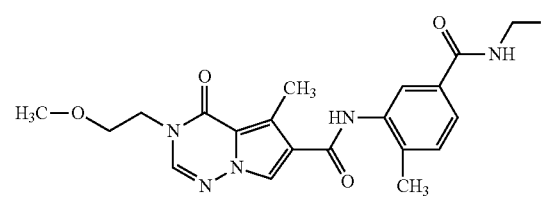
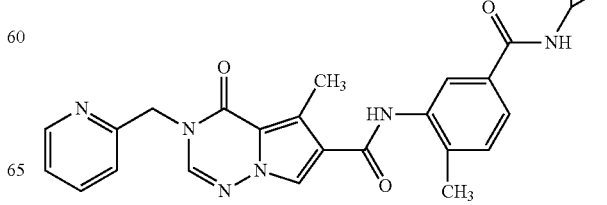

-continued
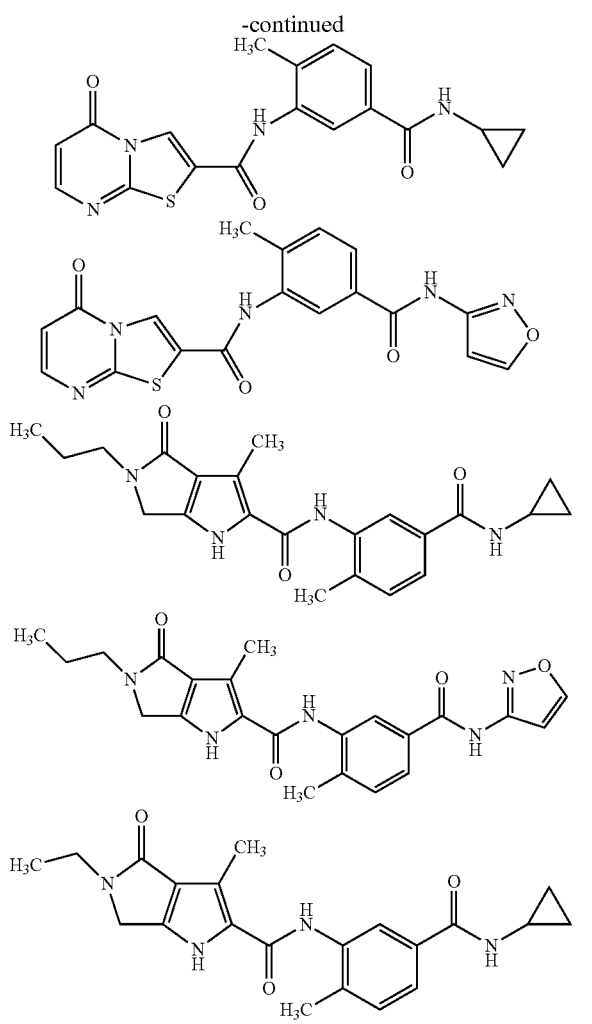
-continued
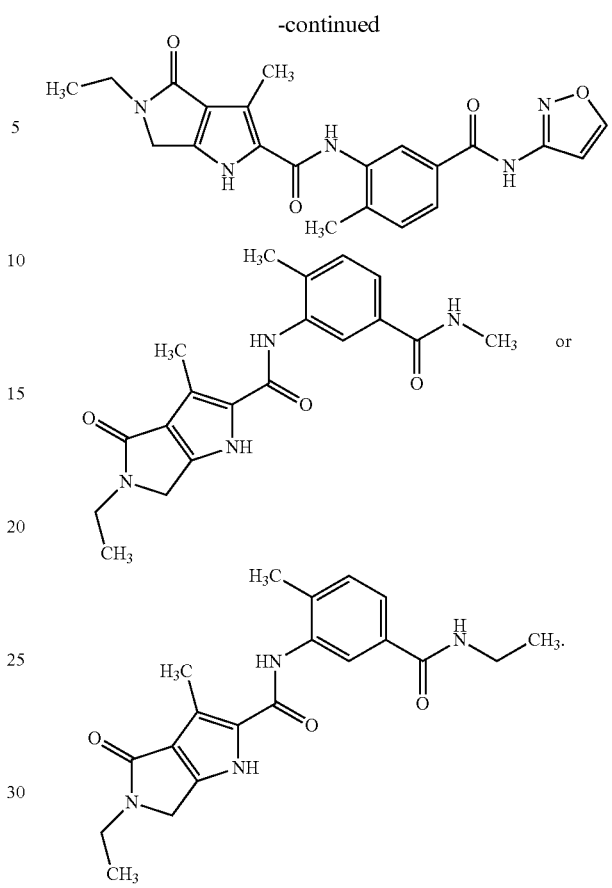
15. The compound according to claim 1 wherein $R^4$ is H, —CH$_3$, —CH$_2$CH$_3$, —CH$_2$CH$_2$CH$_3$, cyclopropyl, isoxazole, —C(O)$_2$CH$_3$, or —C(O)$_2$CH$_2$CH$_3$.
* * * * *